(12) United States Patent
Beach et al.

(10) Patent No.: US 7,736,314 B2
(45) Date of Patent: Jun. 15, 2010

(54) ULTRASONIC TECHNIQUE FOR ASSESSING WALL VIBRATIONS IN STENOSED BLOOD VESSELS

(75) Inventors: Kirk W. Beach, Seattle, WA (US); Yongmin Kim, Lake Forest Park, WA (US); Siddhartha Sikdar, Seattle, WA (US)

(73) Assignee: University of Washington, Seattle, WA (US)

( * ) Notice: Subject to any disclaimer, the term of this patent is extended or adjusted under 35 U.S.C. 154(b) by 1043 days.

(21) Appl. No.: 11/218,292

(22) Filed: Aug. 31, 2005

(65) Prior Publication Data

US 2006/0079782 A1  Apr. 13, 2006

Related U.S. Application Data

(60) Provisional application No. 60/606,162, filed on Aug. 31, 2004.

(51) Int. Cl.
*A61B 8/00* (2006.01)

(52) U.S. Cl. .................. 600/437; 73/584; 181/101; 367/87

(58) Field of Classification Search ......... 600/437–461; 604/19, 20; 73/603
See application file for complete search history.

(56) References Cited

U.S. PATENT DOCUMENTS

| | | | |
|---|---|---|---|
| 5,194,291 A | 3/1993 | D'Aoust et al. ............. 148/276 |
| 5,534,232 A | 7/1996 | Denes et al. ............ 422/186.26 |
| 5,638,823 A * | 6/1997 | Akay et al. ................. 600/528 |
| 5,824,277 A | 10/1998 | Campos et al. .......... 423/242.1 |
| 5,840,028 A * | 11/1998 | Chubachi et al. ............. 600/437 |
| 5,919,139 A | 7/1999 | Lin ............................. 600/443 |
| 5,935,339 A | 8/1999 | Henderson et al. ............. 134/1 |
| 6,036,650 A * | 3/2000 | Wu et al. ..................... 600/462 |
| 6,200,539 B1 | 3/2001 | Sherman et al. ........ 422/186.04 |
| 6,406,759 B1 | 6/2002 | Roth ........................... 427/562 |
| 6,706,892 B1 | 3/2004 | Ezrin et al. ................. 548/548 |
| 6,709,407 B2 * | 3/2004 | Fatemi ........................ 600/559 |
| 6,875,176 B2 | 4/2005 | Mourad et al. ............. 600/442 |
| 2004/0002654 A1 | 1/2004 | Davidson et al. ............ 600/454 |
| 2005/0065436 A1 | 3/2005 | Ho et al. ..................... 600/431 |
| 2005/0182319 A1* | 8/2005 | Glossop ...................... 600/424 |
| 2008/0045864 A1* | 2/2008 | Candy et al. ................... 601/2 |
| 2008/0200815 A1* | 8/2008 | Van Der Steen et al. .... 600/467 |

FOREIGN PATENT DOCUMENTS

WO    WO 02/069805    12/2002

\* cited by examiner

*Primary Examiner*—Brian Casler
*Assistant Examiner*—Nasir Shahrestani
(74) *Attorney, Agent, or Firm*—Ronald M. Anderson

(57) ABSTRACT

A real-time signal processing technique for ultrasonic imaging of tissue vibrations for localizing the source of a bruit in a 2D image with respect to the anatomy and/or for obtaining simultaneous information about vibrations and the underlying blood flow. The bruit can be quantitatively assessed using an ensemble of ultrasound echoes. Signal processing enables estimation of wall displacement and the display of time-resolved vibration spectrum. Vibrations are detected and color-coded according to their amplitude and frequency and overlaid on the B-mode and/or color-flow image in real time. Proposed vibration imaging algorithms use data acquired during conventional ultrasonic color-flow imaging and the clutter signal, normally suppressed in color-flow imaging, to detect and characterize tissue vibrations. Three vibration imaging algorithms based on parametric modeling of vibrations and other criteria distinguish between clutter, blood flow, and vibrations. The techniques are usable to detect, locate, image, and quantitatively grade stenoses in blood vessels.

6 Claims, 30 Drawing Sheets

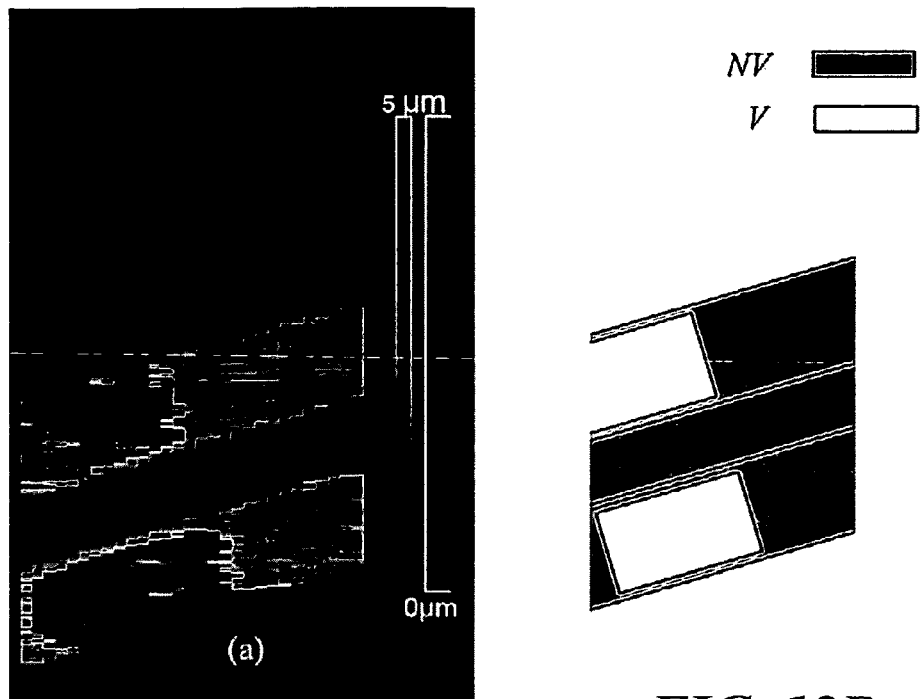
*FIG. 12A*
*FIG. 12B*
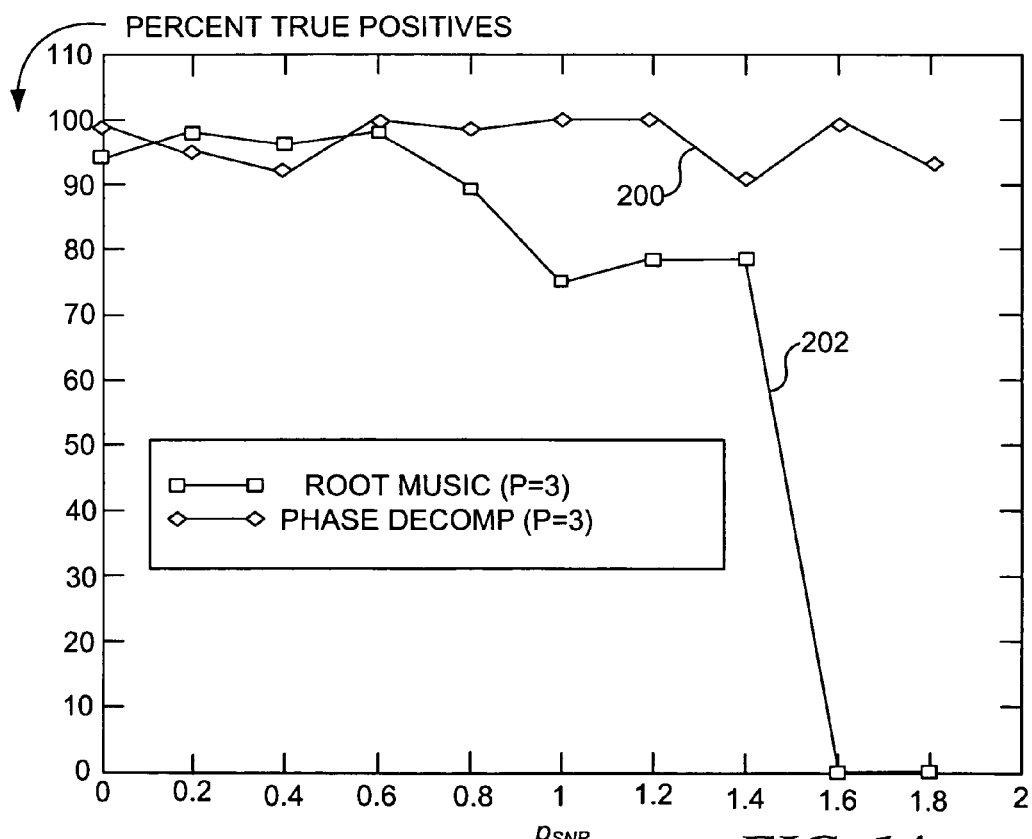
*FIG. 14*

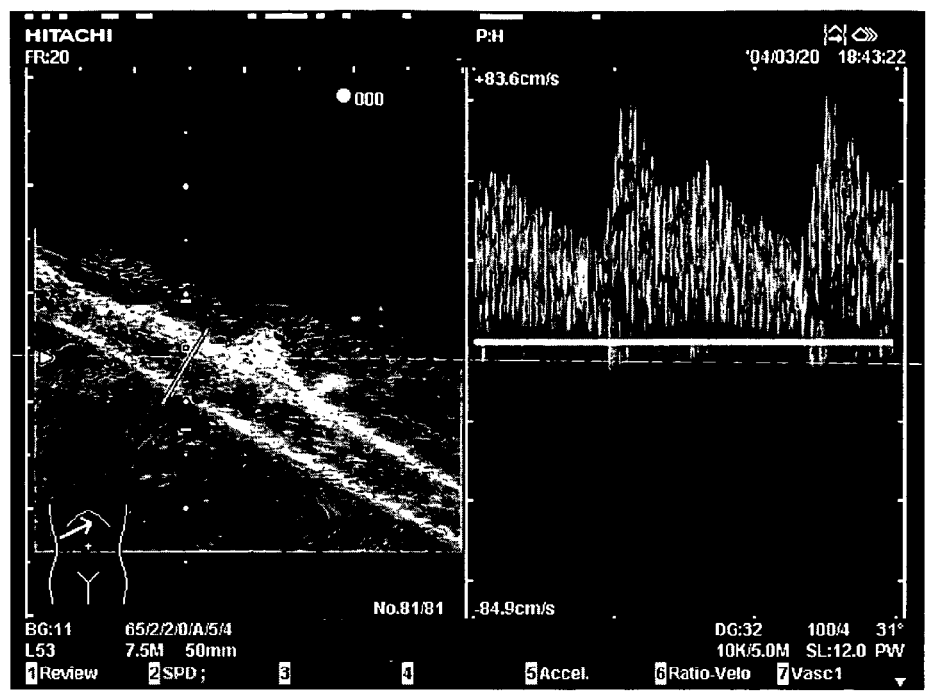
FIG. 19
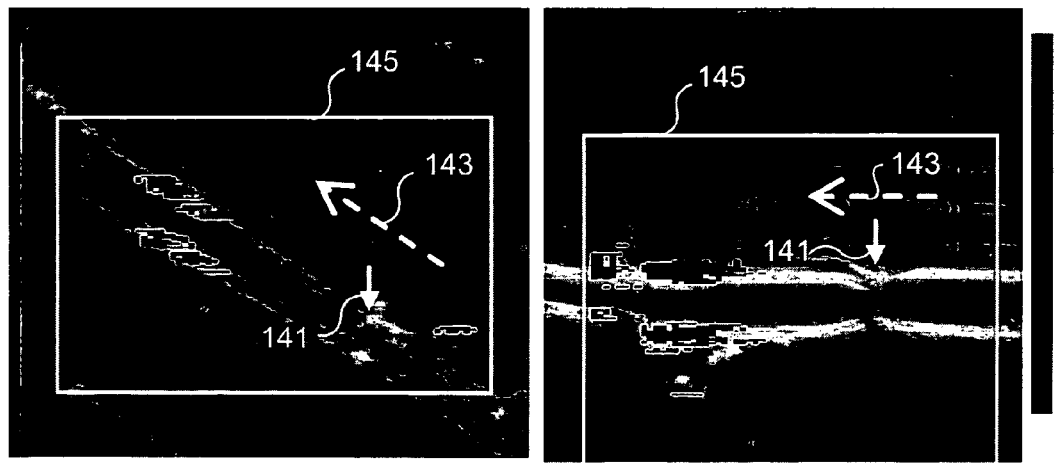
FIG. 20A  FIG. 20B

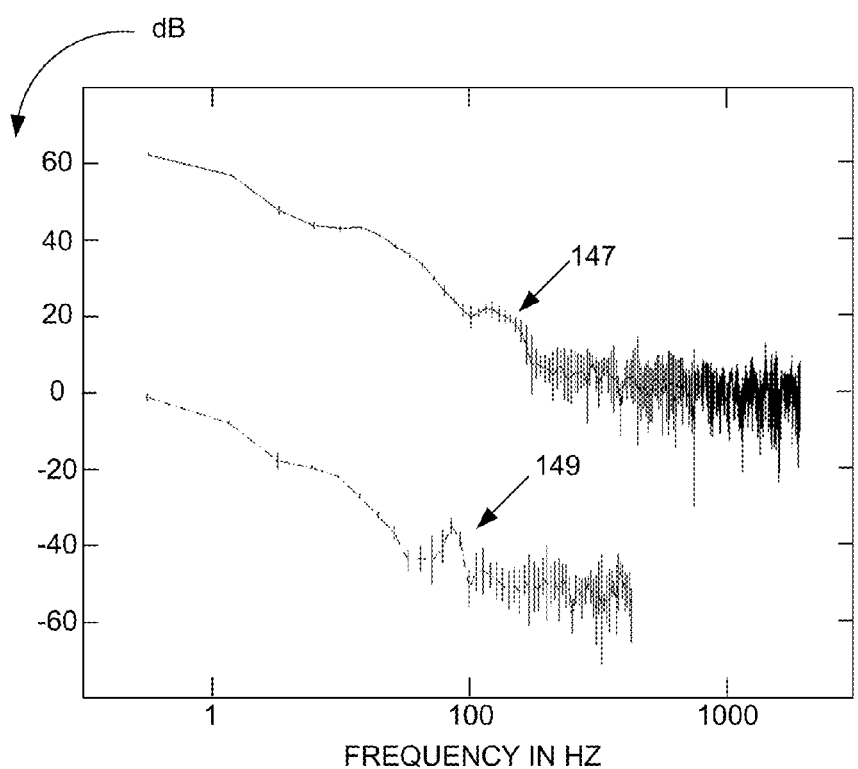
*FIG. 21*
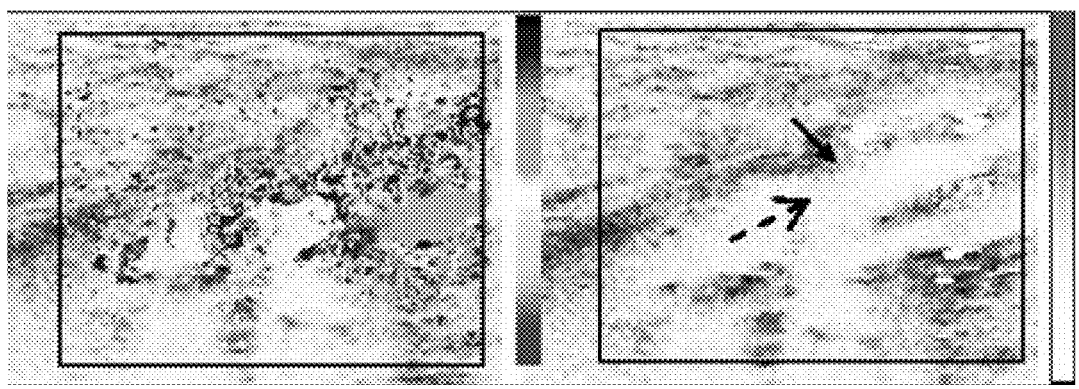
*FIG. 22A*  *FIG. 22B*

ULTRASONIC TECHNIQUE FOR ASSESSING WALL VIBRATIONS IN STENOSED BLOOD VESSELS

RELATED APPLICATIONS

This application is based on a prior provisional application Ser. No. 60/606,162, filed on Aug. 31, 2004, and a prior copending international application, Serial No. PCT/US2004/32427, filed on Oct. 1, 2004 (designating the United States), the benefits of the filing dates of which are hereby claimed under 35 U.S.C. §119(e) and 35 U.S.C. §120, and under 35 U.S.C. §365.

GOVERNMENT RIGHTS

This invention was made with U.S. Government support under grant No. N00014-01-G-0460 awarded by the U.S. Office of Naval Research (ONR). The U.S. Government has certain rights in the invention.

BACKGROUND

For more than two centuries, arterial stenoses have been associated with sounds known as bruits that are audible using a stethoscope. Auscultation (passive listening using a stethoscope) is routinely used to qualitatively assess the loudness and pitch of bruits and murmurs in many vascular diseases, such as renovascular hypertension, coronary artery disease, peripheral artery disease and internal bleeding.

It has now been established that vascular sounds associated with stenoses, aneurysms, arteriovenous fistulae and pseudoaneurysms are produced by the forces exerted on vessel walls by eddies produced when blood flows from a high-pressure region to a low-pressure region through a narrow orifice. The luminal area is reduced by a stenosis; therefore the flow velocity in the throat of the stenosis is increased. This local increase in the flow velocity creates a post-stenotic jet, if the post-stenotic expanse region is not sufficiently streamlined to prevent flow separation (i.e., the stenosis is not a "venturi tube"). Regions of high fluid shear are produced due to the difference in velocity across the boundary of the jet. These shear forces produces eddies in the flow, which in turn produce a resistance to the laminar fluid flow. The presence of eddies cause fluctuations in the flow velocity and pressure in the post-stenotic region, which cause a corresponding motion in the vessel walls. The energy produced by the pressure drop across the stenosis is therefore dissipated through these mechanical vibrations of the vessel wall as well as minor heating of the blood. The local vibrations in the vessel wall and surrounding tissue manifest either as audible "bruits" and "murmurs" or palpable "thrills" when they reach the skin surface. The elasticity of the artery walls also introduces a capacitance into the circuits. The post-stenotic capacitance causes the pressure distal to the stenosis to rise during systole. For less severe stenosis, the pressure drop across the stenosis is significant only during the peak systolic pressure phase, thus the bruit lasts only during the systolic phase. However, for more severe stenoses, the pressure drop distal to the stenosis is low, thus a significant pressure gradient exists across the stenosis even during the diastolic phase causing the bruit to extend into the early diastolic phase.

The power spectrum of the vibration exhibits a frequency peak called the "break frequency" that is directly related to the diameter of the orifice and the local flow velocity through the Strouhal number. In other words, the break frequency is inversely proportional to the residual lumen diameter at the stenosis. Phonoangiography and phonocardiography were developed to quantify the spectral content of bruits and murmurs recorded with a sensitive microphone, and carotid phonoangiography has been successfully used to estimate the degree of carotid artery stenosis in multiple clinical trials. However, auscultation and phonoangiography lack sensitivity and specificity because they are limited to diagnosing high-intensity vibrations that reach the skin surface, and the origin of the vibrations cannot be clearly resolved. Currently, there is no diagnostic tool to quantitatively image the vibrations associated with bruits at their origin. Therefore, although tissue vibrations have been shown to be important in diagnosis, their clinical use is currently limited. It would be desirable to provide noninvasive techniques for analyzing bruits and wall vibrations associated with stenosed blood vessels that are not limited to analyzing vibrations that reach the skin surface.

Advances in duplex and color-flow ultrasound in the last two decades have had a significant clinical impact on vascular diagnosis, with the simultaneous availability of anatomy and flow images in real time. Ultrasonic tissue Doppler imaging (TDI) has been used for assessment of abnormal wall motion in the cardiac wall as well as in arteries. In conventional color-flow ultrasound images, tissue vibrations from abnormal blood flow produce characteristic speckled artifacts in the surrounding tissue. These artifacts indicate tissue vibrations and are useful for recognizing stenoses. However, they are difficult to interpret and are not quantitative.

With the introduction of duplex ultrasound, criteria for non-invasive assessment of stenosis severity were developed based upon flow velocity. Although these criteria have been quite useful, such techniques do not analyze the turbulence information present in the wall vibration spectra. It would be desirable to provide non-invasive ultrasound based techniques for evaluating stenosis severity that factor in wall vibrations, as well as flow velocity, to achieve enhanced diagnostic tools.

Accordingly, it would be desirable to develop new tissue vibration detection and imaging modes for ultrasound instruments in which vibrations produced by stenosed blood vessels can be detected and color-coded according to their amplitude and frequency and overlaid on a B-mode and/or a color-flow image in real time. The tissue vibration-imaging mode might then be used for locating the origin of the vibration more precisely, relative to the patient's anatomy and/or for obtaining simultaneous information about vibrations and the underlying stenosis.

SUMMARY

The concepts disclosed herein were developed to detect, localize and quantify arterial stenoses by imaging tissue vibrations associated with such stenoses. Sounds caused by these vibrations (bruits and murmurs) are sometimes audible using a stethoscope, or palpable at the skin surface, and are indicative of various physiological conditions, including internal bleeding and arterial stenoses. The techniques disclosed herein employ algorithms that process an ensemble of received ultrasound echoes for detecting tissue vibrations, imaging tissue vibrations in a relatively large region of interest, and quantifying the hemodynamic properties of the stenosis based on the measured properties of the tissue vibrations. The algorithms disclosed herein have been implemented in a programmable ultrasound system to study the usefulness of tissue vibrations in real-time localization of stenoses in peripheral arteries and coronary arteries in humans.

In general, the vibration imaging algorithms described herein use an ensemble of 2D ultrasound data acquired during conventional ultrasonic imaging and the clutter signal (which is normally suppressed in conventional color-flow imaging) associated with such data, to detect and characterize tissue vibrations. Various signal processing algorithms have been developed that are suitable for this purpose, including three primary algorithms, based on parametric modeling of vibrations and the criteria to distinguish between clutter, blood flow, and vibrations. A first primary algorithm is based on phase decomposition, a second primary algorithm is based on using an estimation of complex exponentials in noise, and a third primary algorithm is based on autoregressive modeling.

Another set of algorithms utilize a larger ensemble of received ultrasound echoes (typically 64-512) from a small region of interest (e.g., a Doppler range gate) near the site of the stenosis to confirm the presence of tissue vibrations, and to measure the properties of the tissue vibrations with improved accuracy. Various signal processing algorithms have been developed that are suitable for this purpose, including a two-dimensional (2D) Fourier transform utilizing both the slow time variations in the received ultrasound echoes as a result of motion as well as variation in the motion of tissue at neighboring locations along the direction of the ultrasound beam. A first algorithm for identifying vibrations is based on the 2D Fourier transform of the quadrature-demodulated received echo and utilizes the Radon transform to identify spectral peaks corresponding to vibrations. A second algorithm for identifying vibrations utilizes a multi-frequency average to identify spectral peaks corresponding to vibrations, and suppress other sources of noise. A method for localizing and grading arterial stenoses using such algorithms is further disclosed herein.

Also disclosed herein is a new tissue vibration imaging mode for ultrasound instruments in which soft-tissue vibrations produced due to impact of blood flow eddies are detected and color-coded according to their amplitude and frequency, and overlaid on the B-mode and/or color-flow image in real time. The tissue vibration imaging mode can be used for locating the origin of vibration more precisely relative to the anatomy, and/or for obtaining simultaneous information about vibrations and the underlying blood flow.

Real-time tissue vibration imaging has been implemented at frame rates, for example, of 10 frames/second, on an ultrasound system with a software-programmable signal and image processing back-end. The preliminary results confirm that vibrations produced as a result of arterial stenoses can be detected and imaged using such techniques. The vibration amplitude is expected to be the largest near a site downstream of the stenosis, and this fact can be used to localize a stenosis quickly and non-invasively. The strong backscattered ultrasonic echoes from tissue vibrations can improve detection of stenoses that are otherwise hard to detect using Doppler blood velocity-based methods due to weak scattering from blood.

Potentially, this new tissue vibration imaging technology could be useful in a variety of devices and clinical settings. For example, a low-cost portable screening device with tissue vibration detection functionality could be beneficially employed by general practitioners for diagnosing and/or screening patients with coronary and peripheral artery disease, or by paramedics and trauma centers to evaluate patients with chest pain. In addition, a tissue vibration imaging mode on high-end ultrasound systems can augment duplex ultrasound for enhanced diagnostic capability, which could be beneficially employed by imaging centers, cardiology clinics, and hospitals for diagnosing stenoses in patients. The detected tissue vibrations indicative of a stenosis could be presented as an audible signal in a manner recognizable to a person trained to listen to bruits using a stethoscope or as a palpable signal recognizable to a person trained to detect palpable thrills.

One aspect of the concepts disclosed herein is directed to a method for detecting and localizing arterial stenoses using an ensemble of 2D ultrasound data by detecting and characterizing tissue vibrations caused by blood flow eddies downstream of a stenosis. The method includes the step of processing an ensemble of 2D ultrasound data to produce a tissue motion spectrum signal of a site being imaged. The tissue motion spectrum signal is then processed to produce a tissue vibration signal, from which any contribution to the tissue motion from a source other than vibrations at the stenosis has been substantially minimized. A vibration image is displayed using the tissue vibration signal and indicates a location of the stenosis at the site.

One approach for processing the ensemble of 2D ultrasound data comprises the steps of estimating a correlation matrix from the ultrasound data, and carrying out an eigen decomposition of the correlation matrix to identify a signal subspace and a noise subspace. A frequency of the dominant vibration components in the signal subspace and the noise subspace is then estimated, and based upon that estimate, a vibration amplitude estimate and a vibration frequency estimate are determined. At least one of the vibration amplitude estimate and the vibration frequency estimate comprises the tissue vibration signal.

A second approach for processing the ensemble of 2D ultrasound data for imaging vibrations associated with stenoses includes the step of computing the reflection coefficients of an autoregressive model of an ensemble of received ultrasound echoes. Linear prediction filter coefficients are computed from the reflection coefficients. A power spectrum is estimated, and the peaks in the power spectrum are detected. Based upon the estimate of the power spectrum and the peaks, a vibration amplitude estimate and a vibration frequency estimate are determined. At least one of the vibration amplitude estimate and the vibration frequency estimate again comprises the tissue vibration signal.

In yet another approach for processing the ensemble of 2D ultrasound data, a mean clutter velocity is estimated from the ultrasound data using autocorrelation. The ensemble of 2D ultrasound data is down-mixed with the mean clutter velocity, producing a down-mixed signal. A phase of the down-mixed signal and a mean phase of the down-mixed signal are determined, and the mean phase is subtracted from the phase of the down-mixed signal, producing a residual phase. The residual phase is then decomposed into its dominant components. By applying energy and frequency thresholds, any contribution to the tissue vibration due to noise and blood flow are substantially suppressed, yielding an estimate of vibration amplitude and vibration frequency of tissue at a site.

The step of decomposing the residual phase preferably comprises the steps of estimating a correlation matrix from the residual phase, and performing an eigen decomposition of the correlation matrix to determine the dominant components.

The step of filtering preferably comprises the step of filtering out clutter and noise at frequencies that are substantially lower than an expected frequency range of tissue vibrations corresponding to a stenosis at the site, and also preferably includes the step of filtering out noise that is at frequencies, which are substantially higher than an expected frequency range of tissue vibrations corresponding to the stenosis at the site. This step also encompasses differentiating between blood flow and tissue vibrations, by utilizing the statistical properties of the signals.

In addition, the method can include the step of confirming that vibrations displayed in the vibration image correspond to a stenosis at the site by placing a Doppler sample volume at a location of the tissue vibration determined from the tissue vibration image. In this step, the tissue vibration spectrum determined from relatively larger ensembles (typically, ensembles including 64-512 pulses) can be employed to confirm the tissue vibration detected from relatively smaller ensembles (typically, ensembles including 6-16 pulses) of 2D ultrasound data.

The step of displaying the vibration image preferably comprises the step of displaying at least one of a vibration amplitude image and a vibration frequency image of the site. Because of its efficiency, the method can include the step of displaying the vibration image in connection with an underlying anatomy of the site (i.e., the B-mode grayscale image), substantially in real time.

Another aspect of the present invention is directed to apparatus for detecting and localizing arterial stenoses using an ensemble of ultrasound data. The apparatus includes an ultrasound transducer for transmitting ultrasound pulses toward the internal site and receiving ultrasound data from scatterers at the internal site, including tissue that is vibrating due to a stenosis. In one embodiment, a front-end system controls the ultrasound pulses produced by the ultrasound transducer and demodulates the echoes received by the ultrasound transducer, producing a signal having both in-phase and quadrature components. The apparatus also includes a back-end system to receive the signal from the front-end system and a tissue vibration processor. The front and back-end systems can optionally be combined into a single unit, or one or more parts of these systems can be operating remotely from other parts of the systems. The tissue vibration processor processes the ultrasound signal to estimate tissue vibrations caused by a stenosis, producing a tissue vibration signal. In one embodiment, the tissue vibration signal is converted to an image signal by the back-end system. A display is coupled to the back-end system to receive the image signal, to display a tissue vibration image in which a stenosis at the internal site is indicated. Optionally, the display could be remote from the tissue vibration detection and identification apparatus. For example, the display can be physically located in a hospital, while the tissue vibration detection and identification apparatus is physically located at another location, such as in an ambulance carrying a patient on which the apparatus is being used. Also, instead of a visible display, the result of tissue vibration detection and identification can be presented as an audible or a palpable output indicating tissue vibrations. The tissue vibration signal can also be interpreted by an automated algorithm to indicate a stenosis, and the result of the automated interpretation can be presented as an electronic readout. Generally, the functions performed by the apparatus are consistent with the steps of the method described above.

This Summary has been provided to introduce a few concepts in a simplified form that are further described in detail below in the Description. However, this Summary is not intended to identify key or essential features of the claimed subject matter, nor is it intended to be used as an aid in determining the scope of the claimed subject matter.

DRAWINGS

Various aspects and attendant advantages of one or more exemplary embodiments and modifications thereto will become more readily appreciated as the same becomes better understood by reference to the following detailed description, when taken in conjunction with the accompanying drawings, wherein.

Figures 5A, 5B:
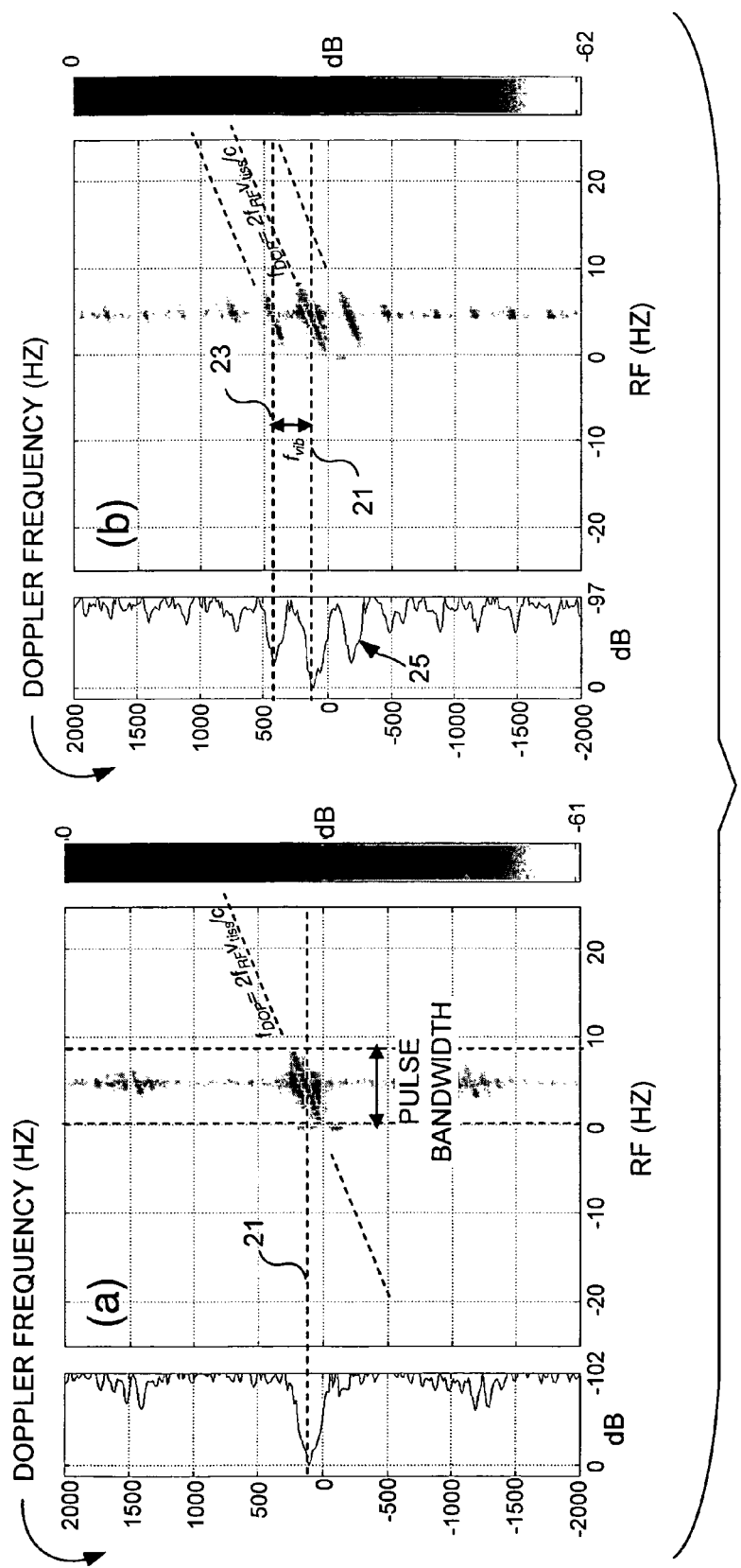
Figures 6A, 6B:
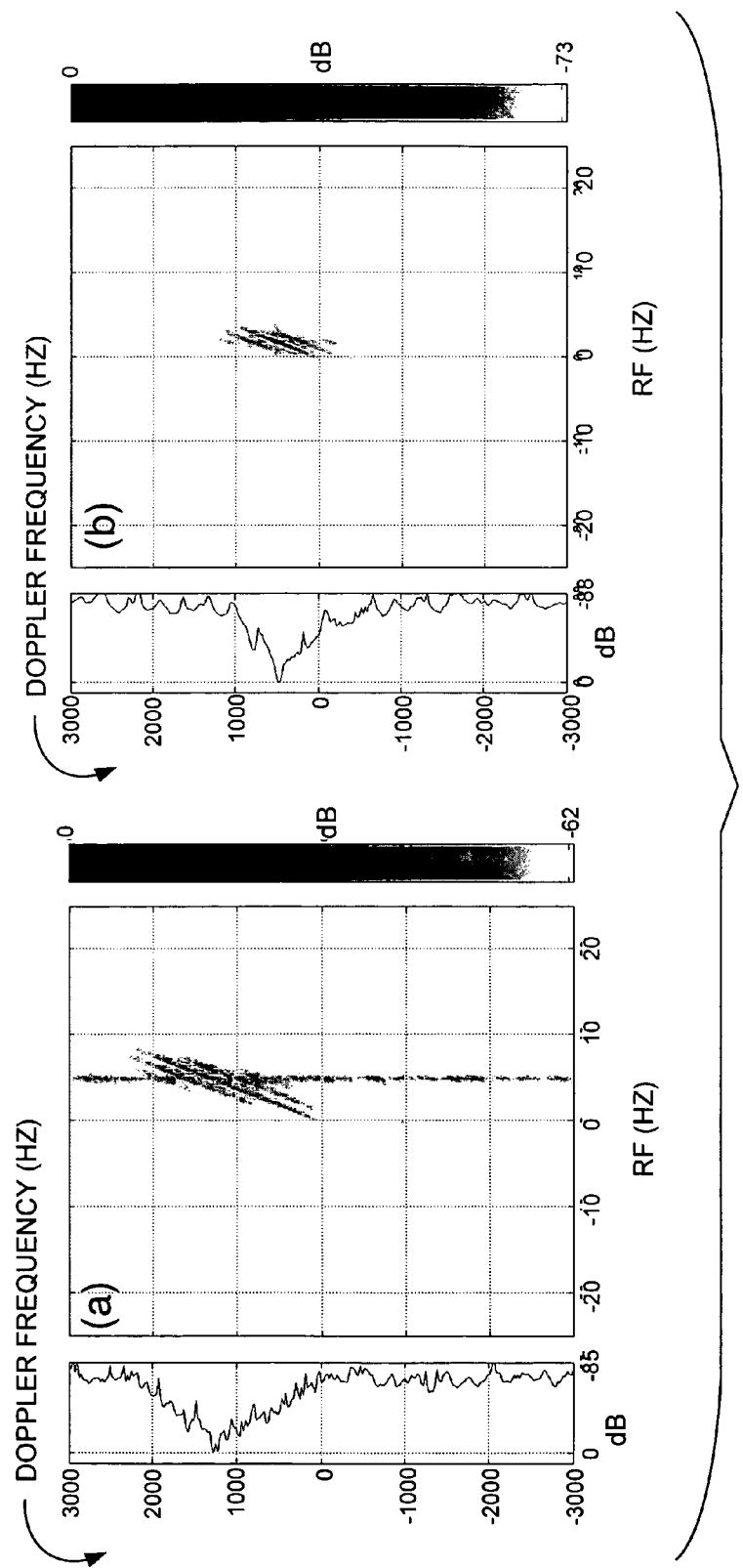
Figures 7A, 7B:
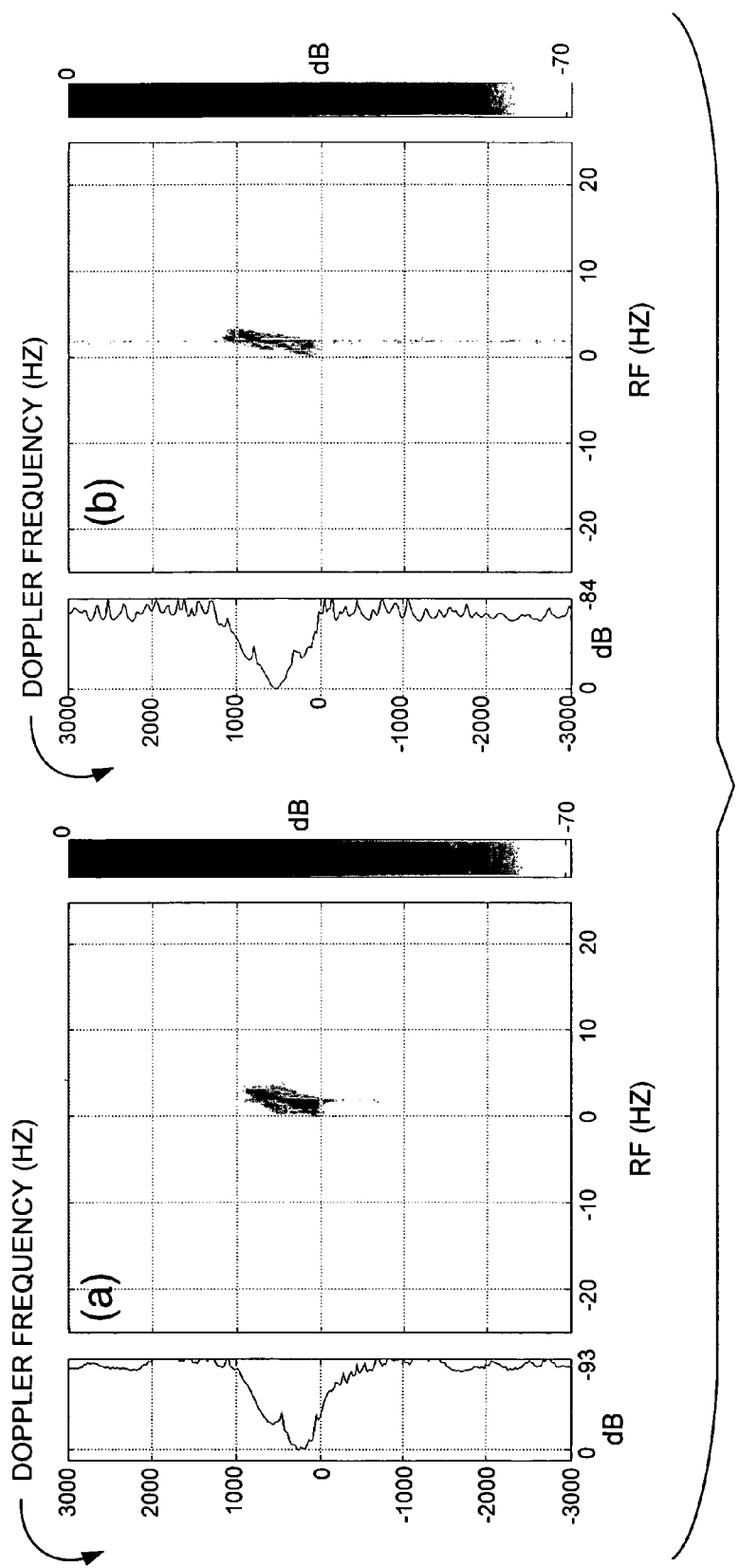
Figures 8A, 8B:
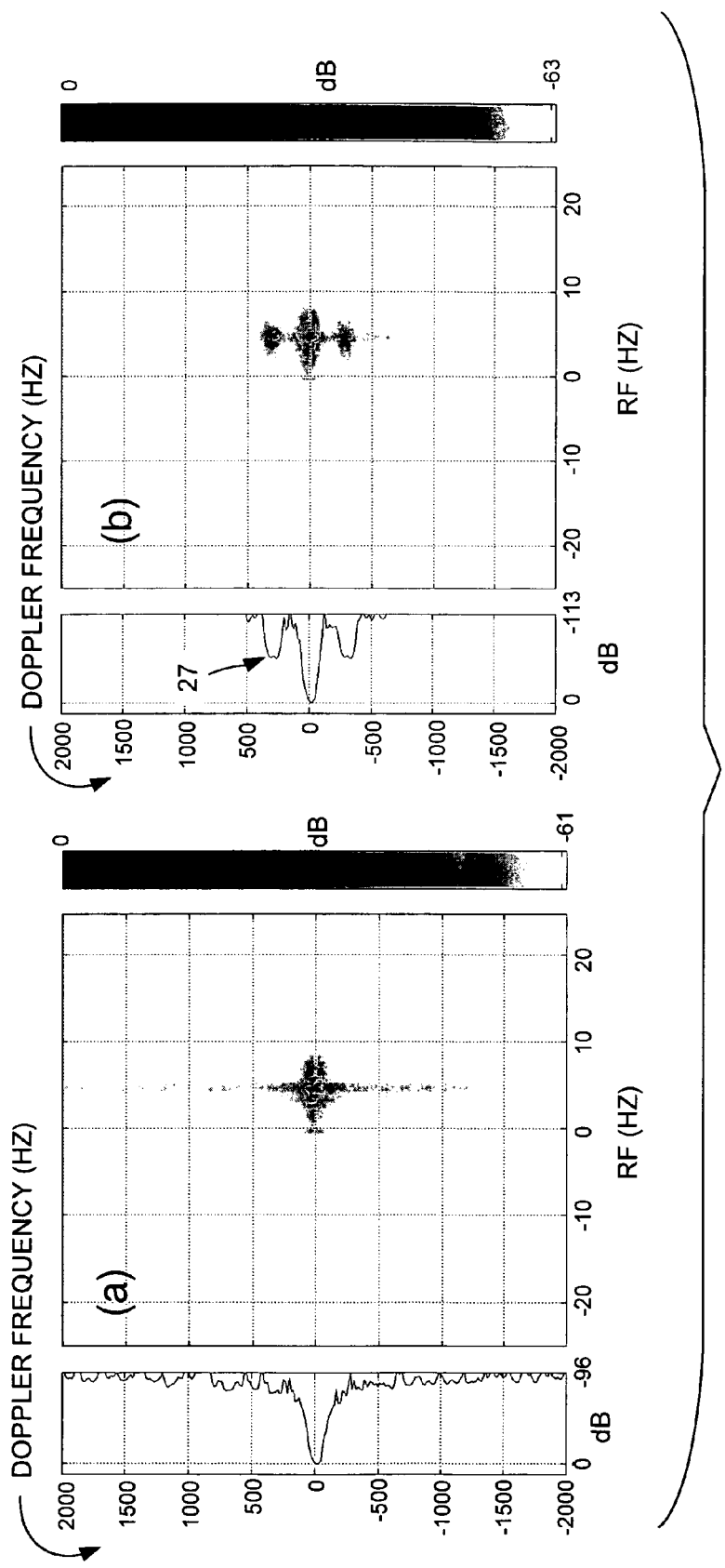
Figure 9A:
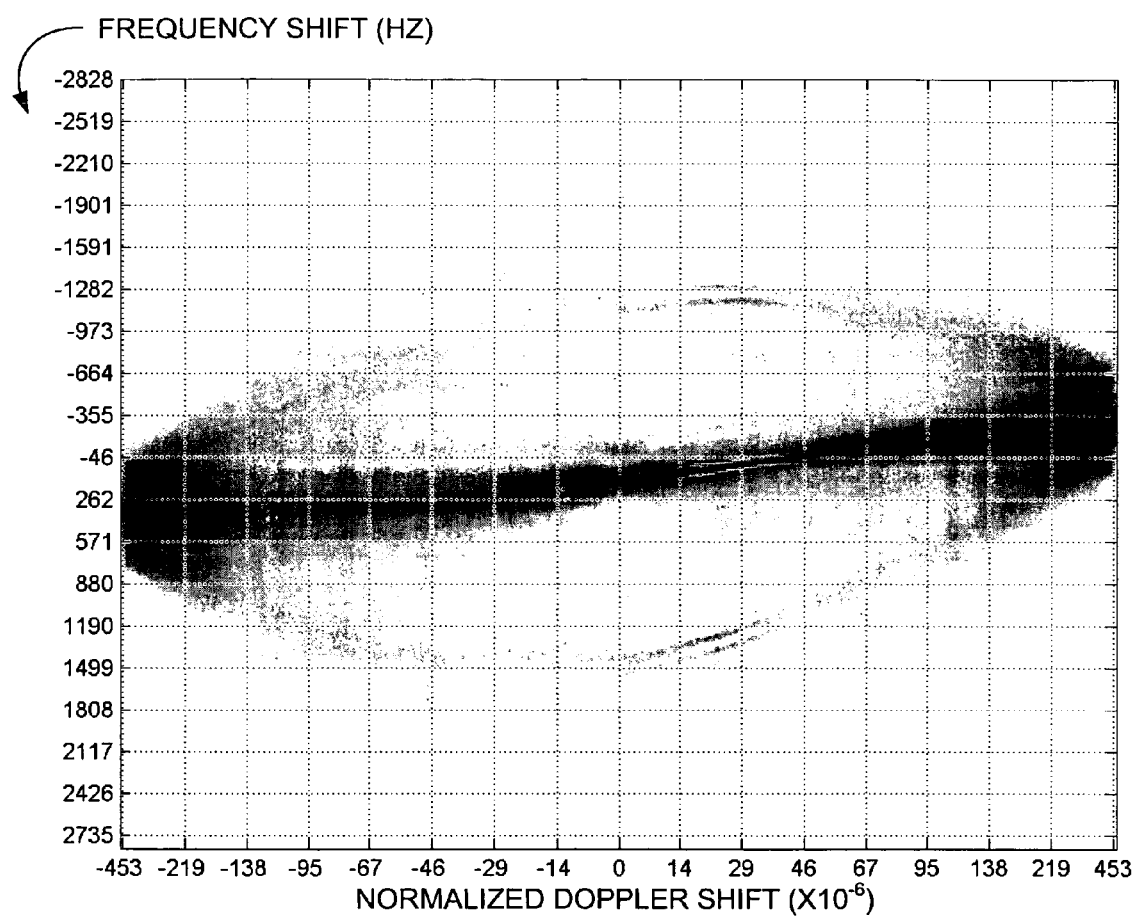
Figure 9B:
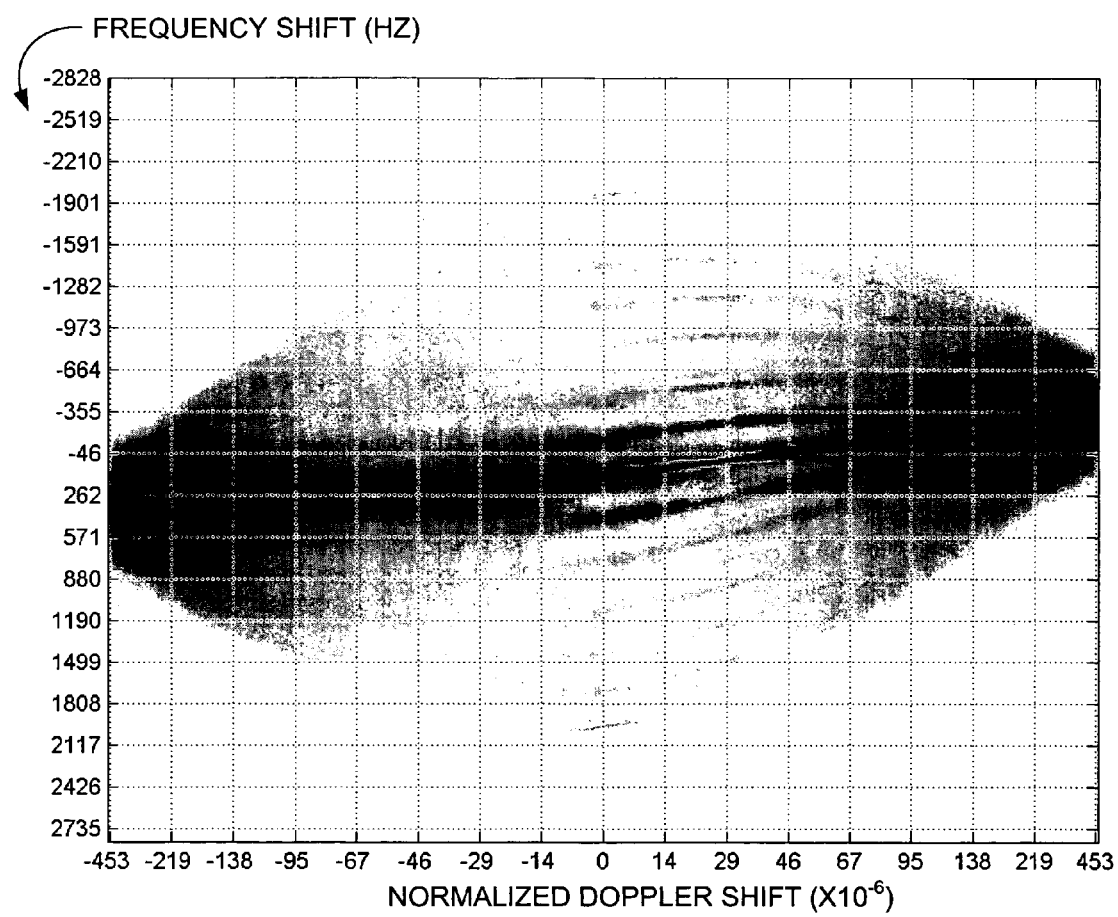
Figure 9C:
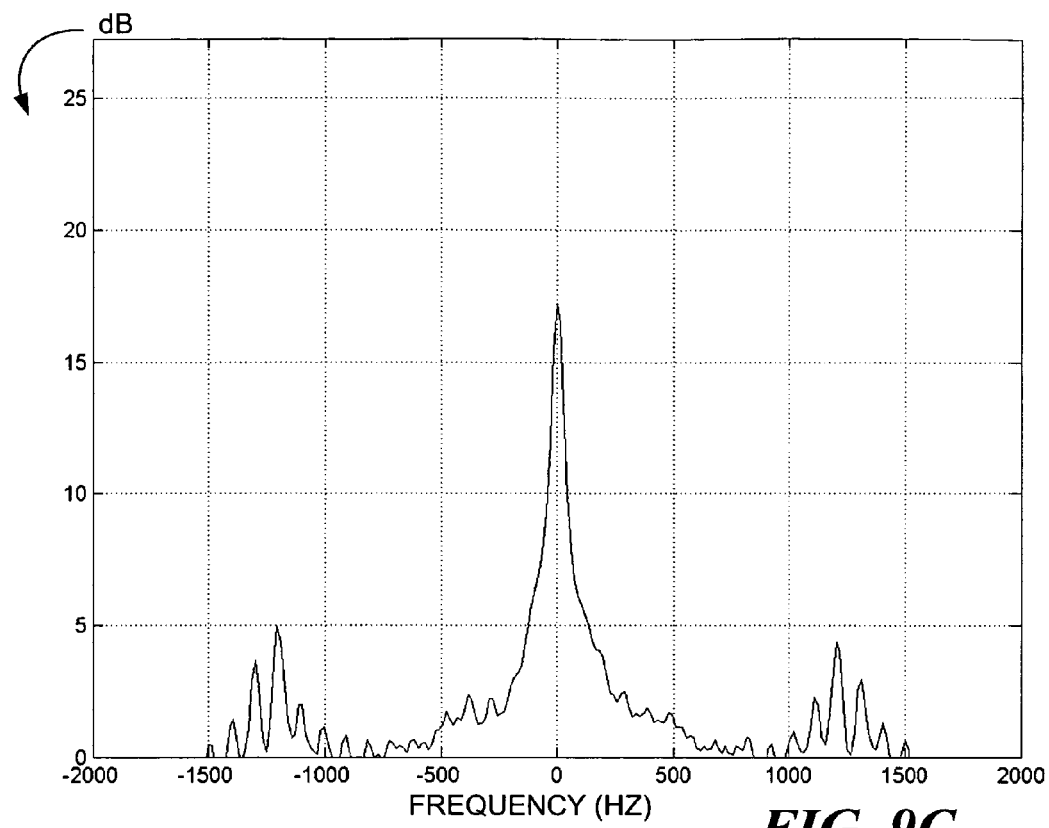
Figure 9D:
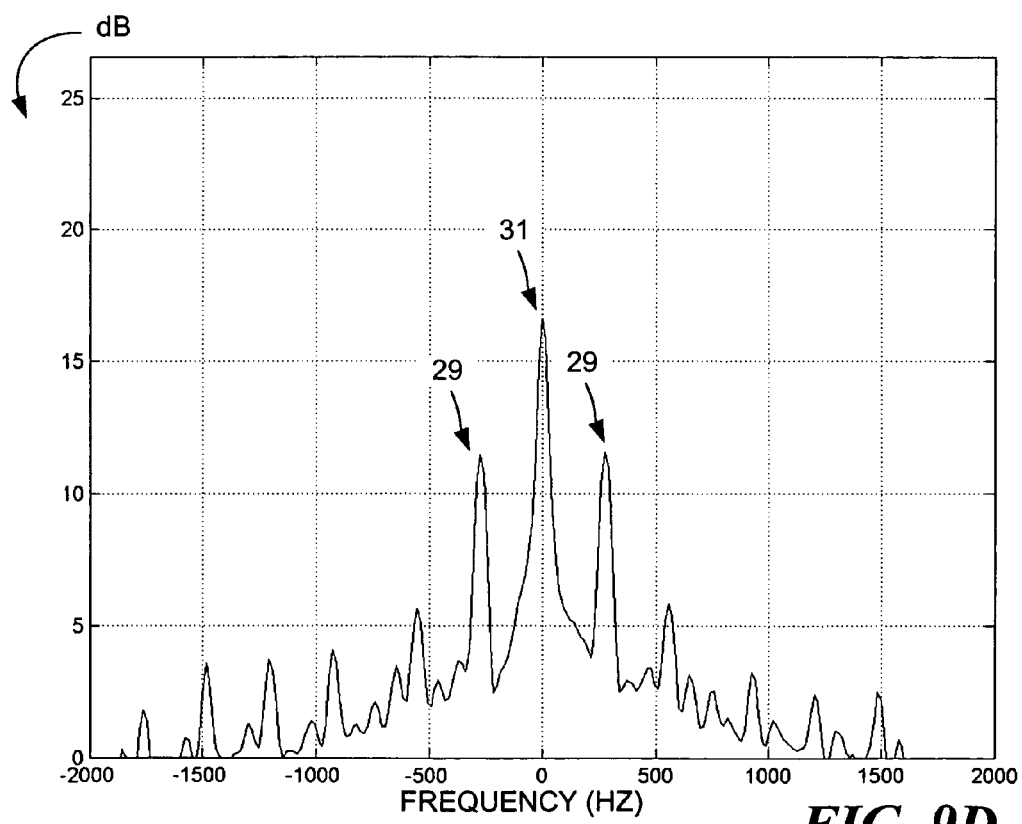
Figure 10A:
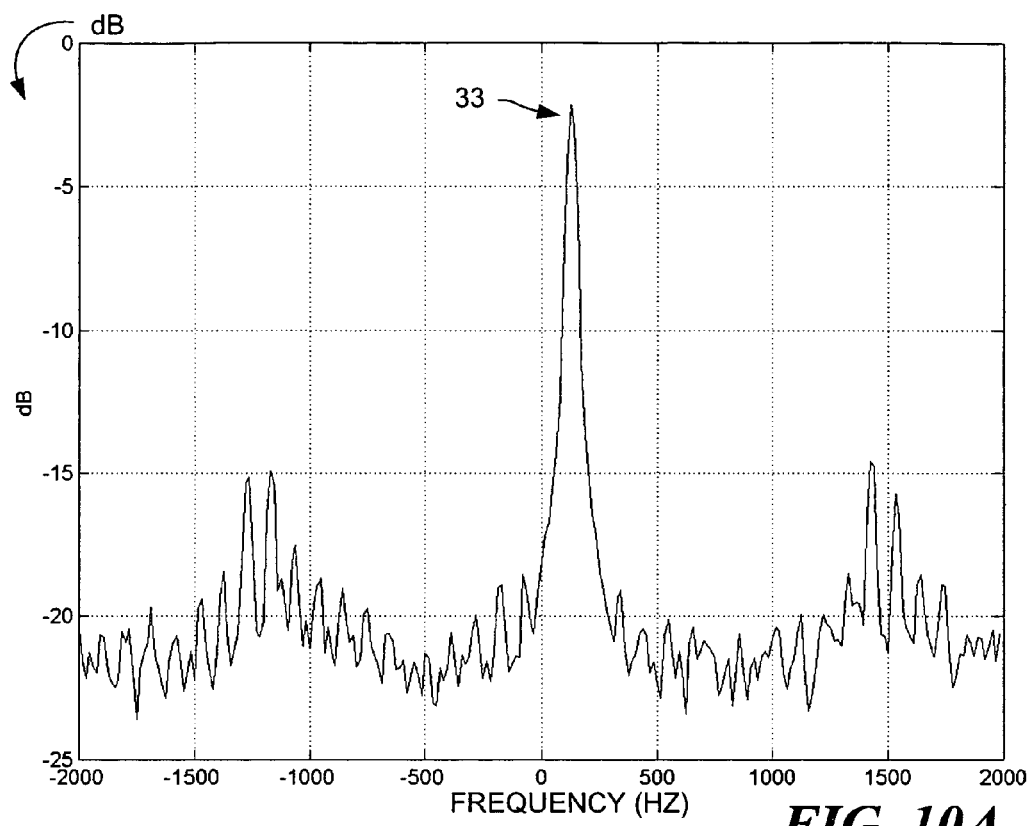
Figure 10B:
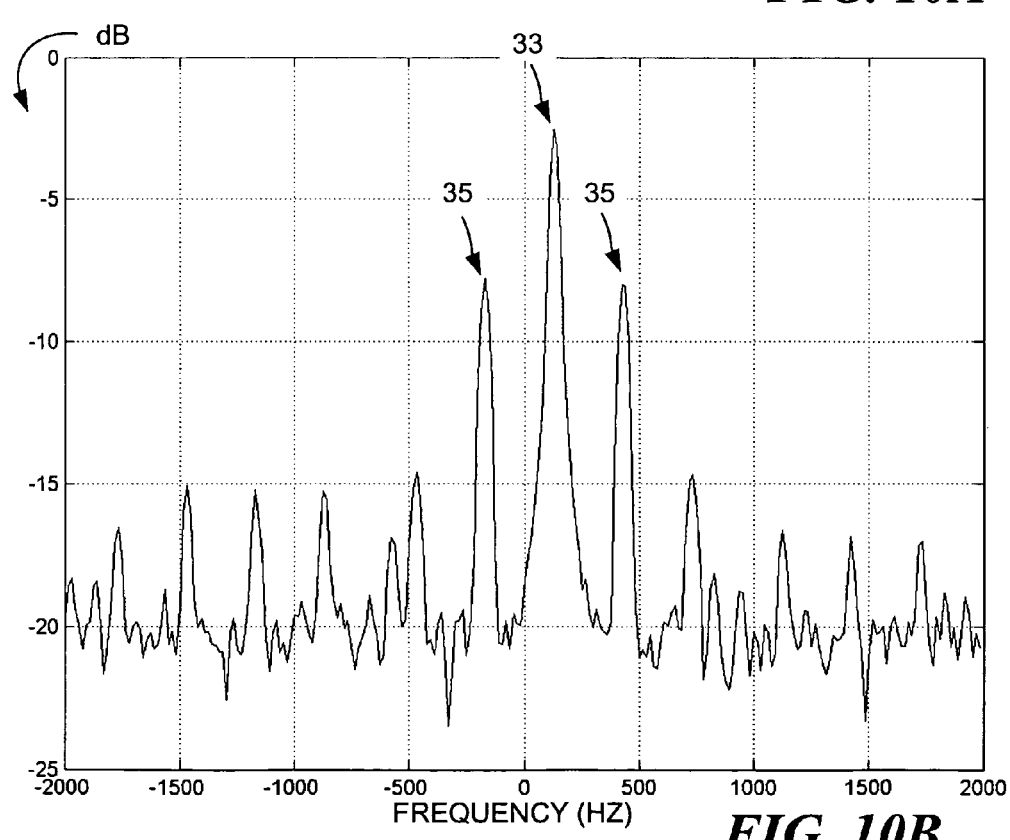
Figure 11A:
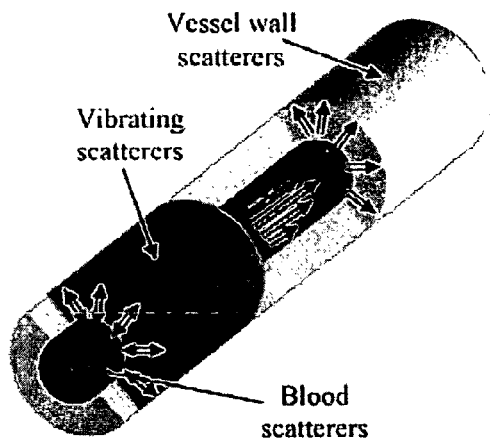
Figure 11B:
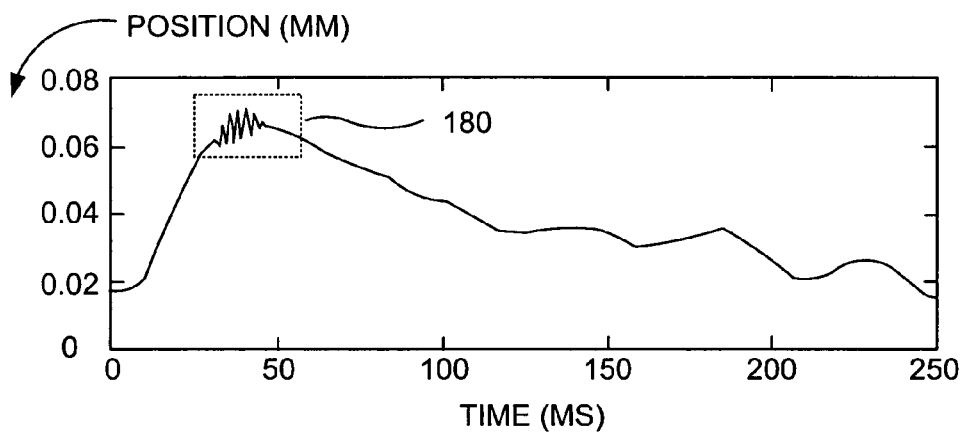
Figure 11C:
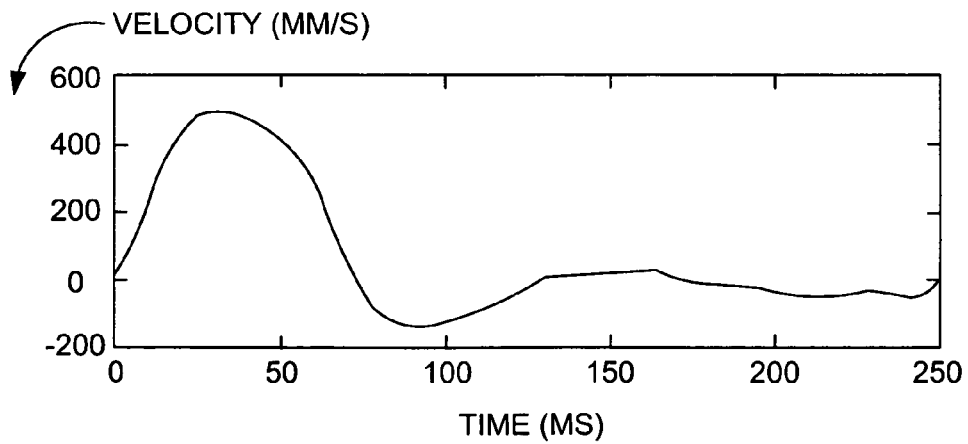
Figure 13C:
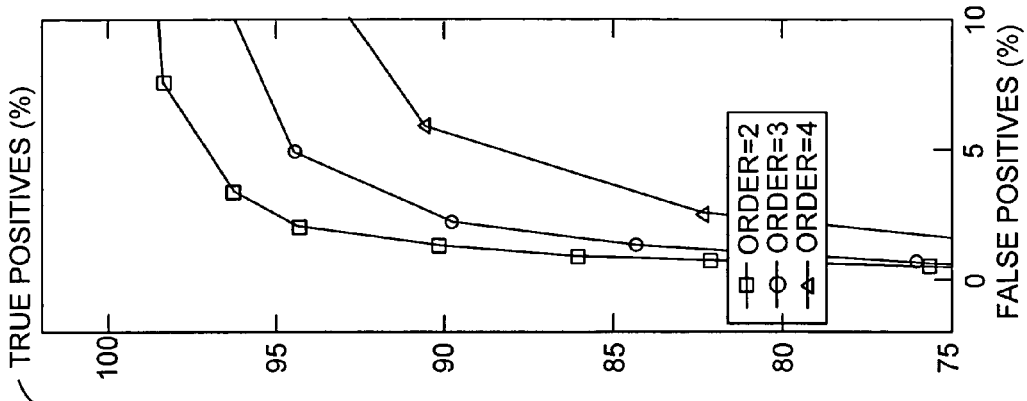
Figure 13B:
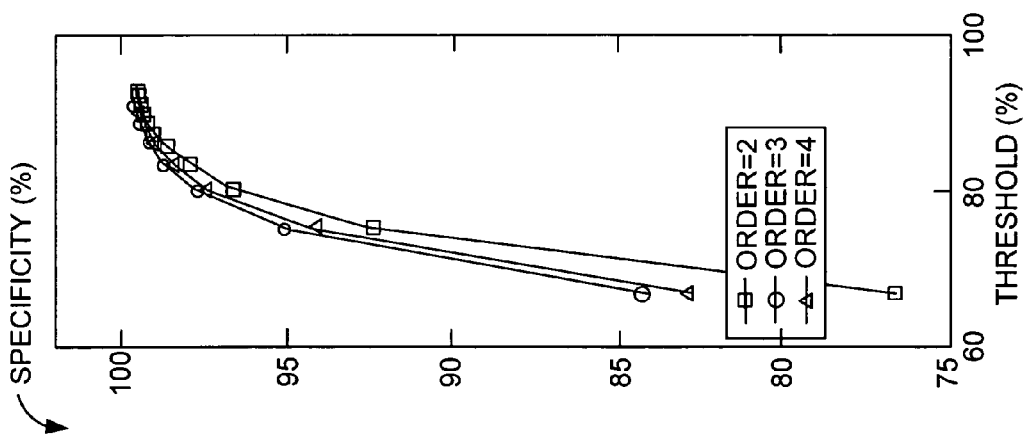
Figure 13A:
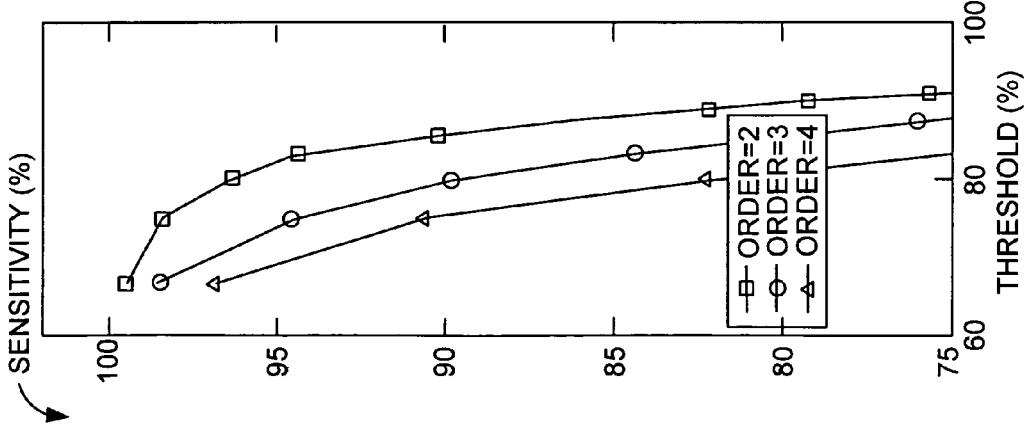
Figure 13F:
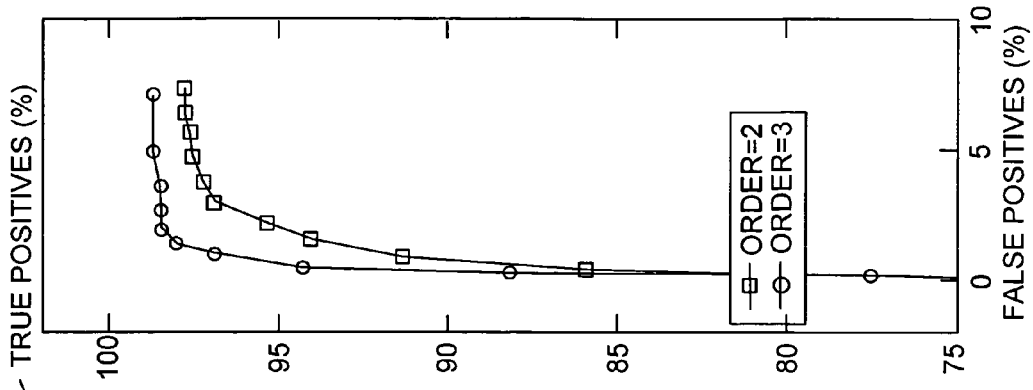
Figure 13E:
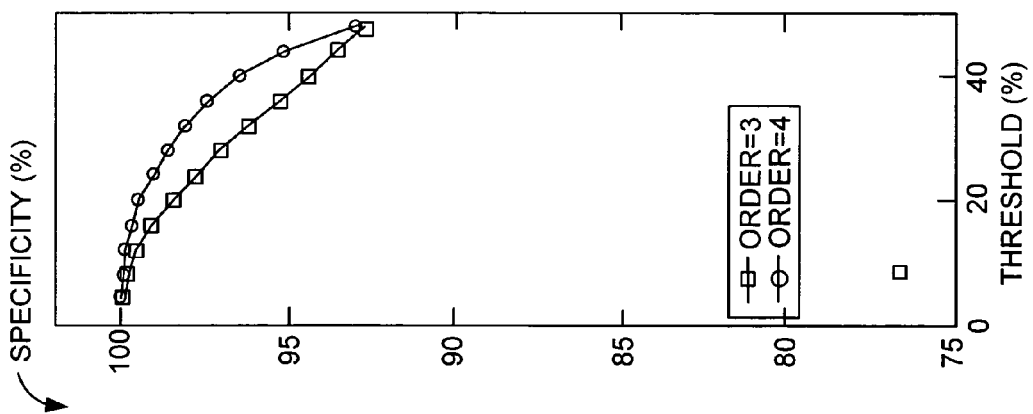
Figure 13D:
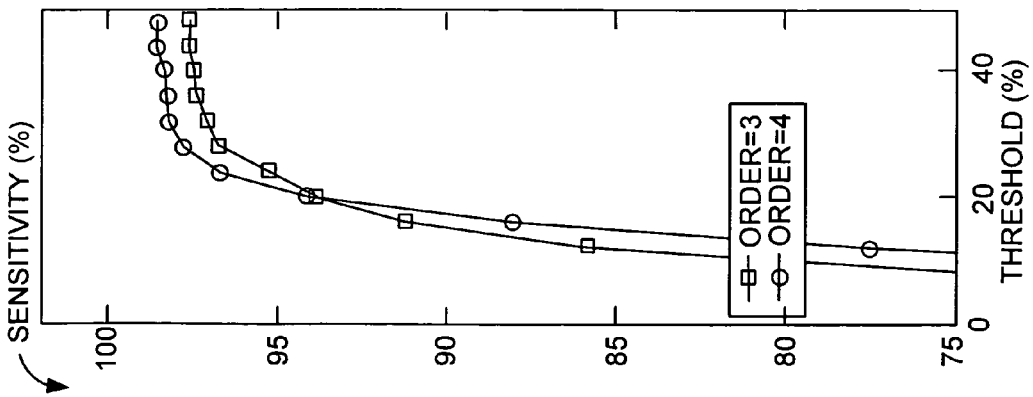
Figure 15:
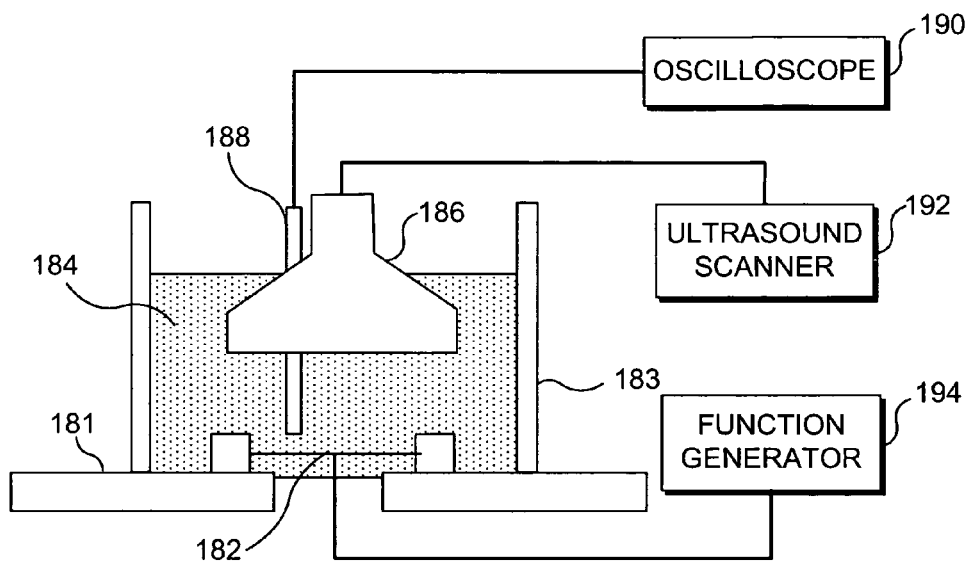
Figure 16A:
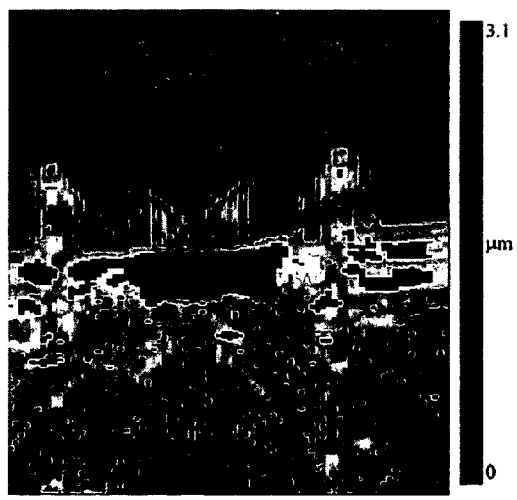
Figure 16B:
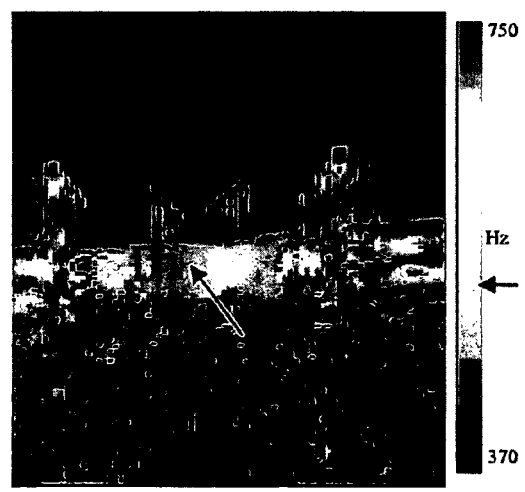
Figure 16C:
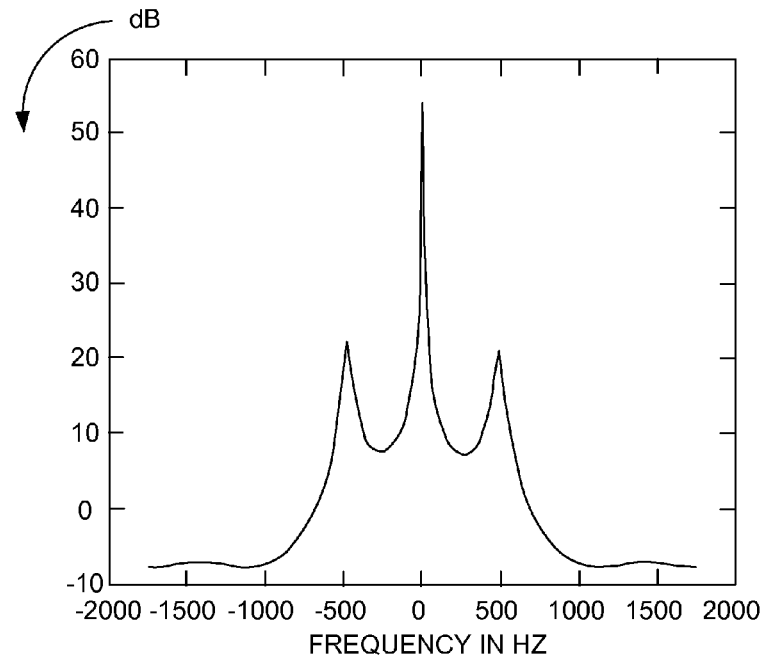
Figure 17A:
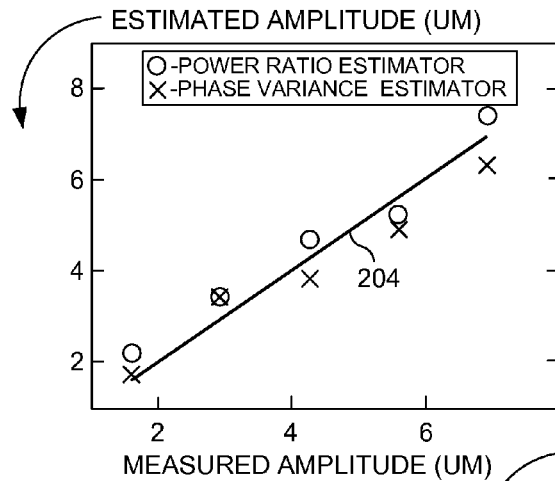
Figure 17B:
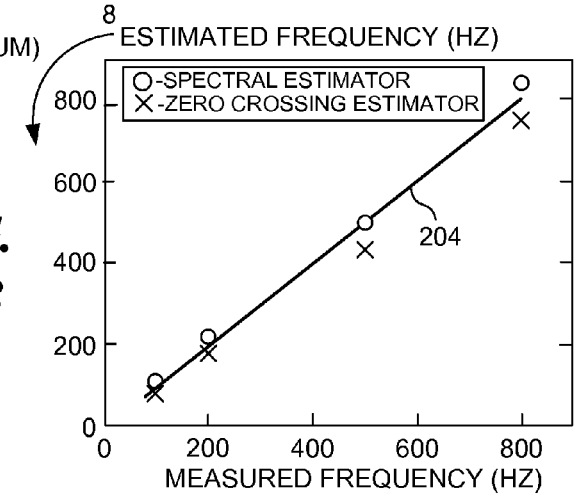
Figure 17C:
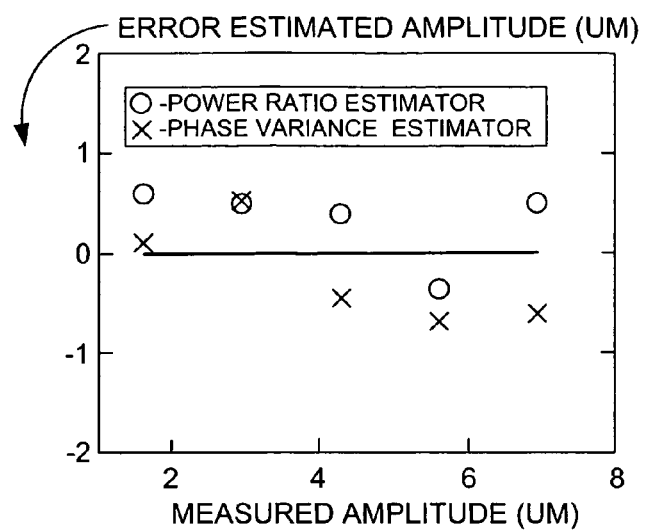
Figure 17D:
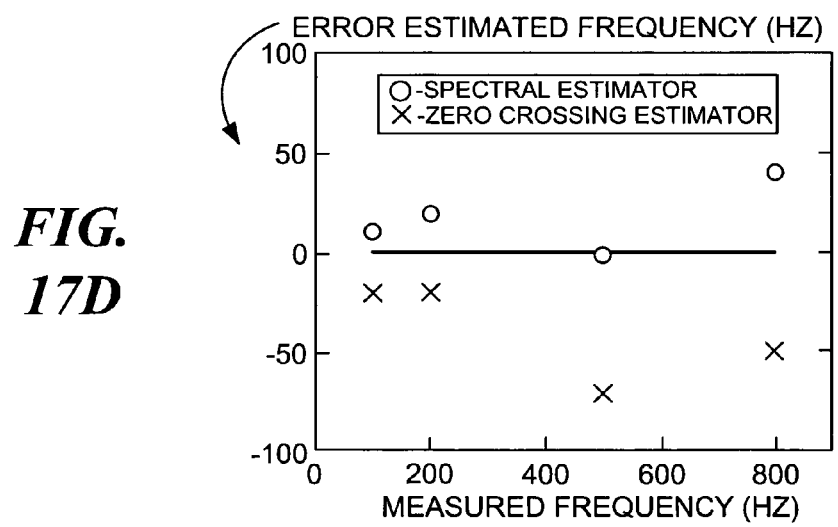
Figure 18:
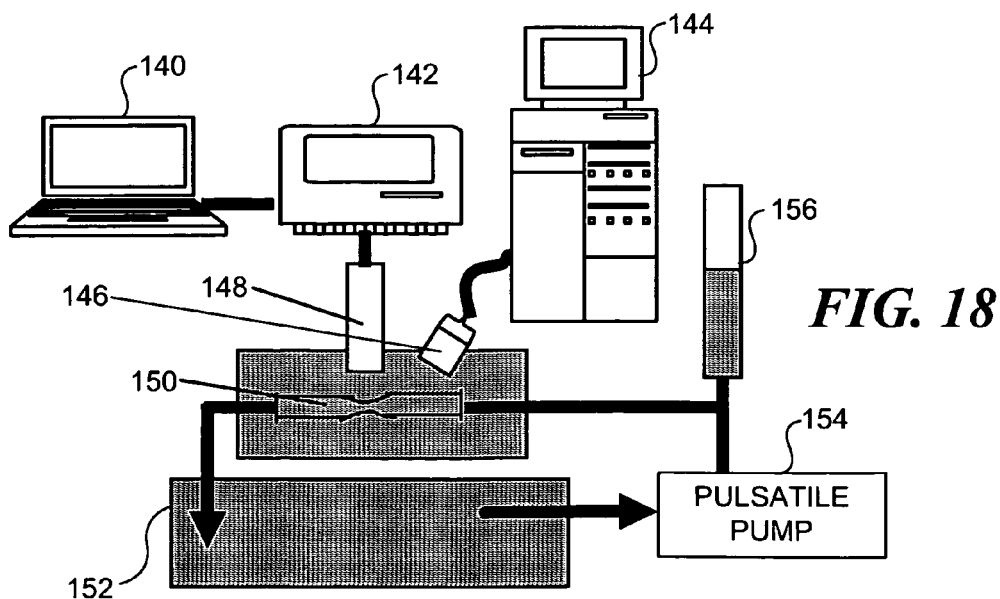
Figures 23A, 23B, 23C:
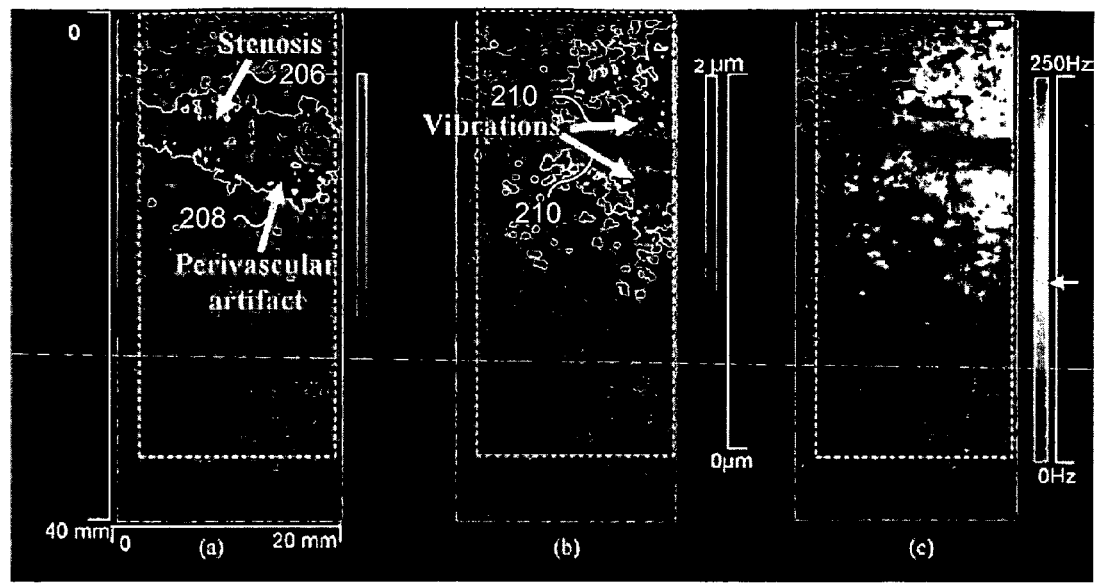
Figure 24A:
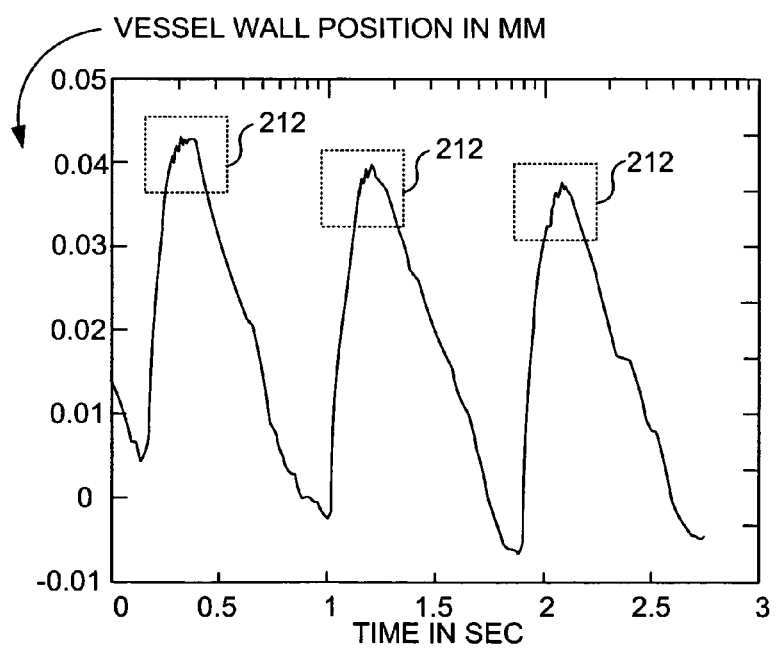
Figure 24B:
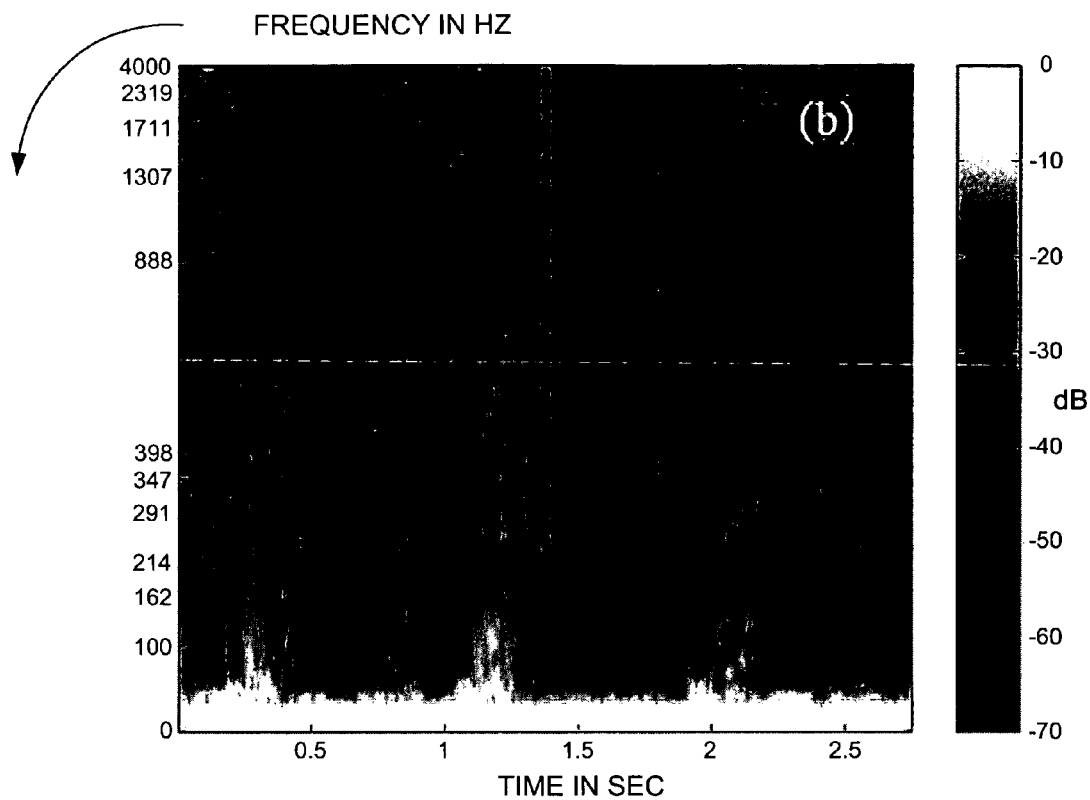
Figure 24C:
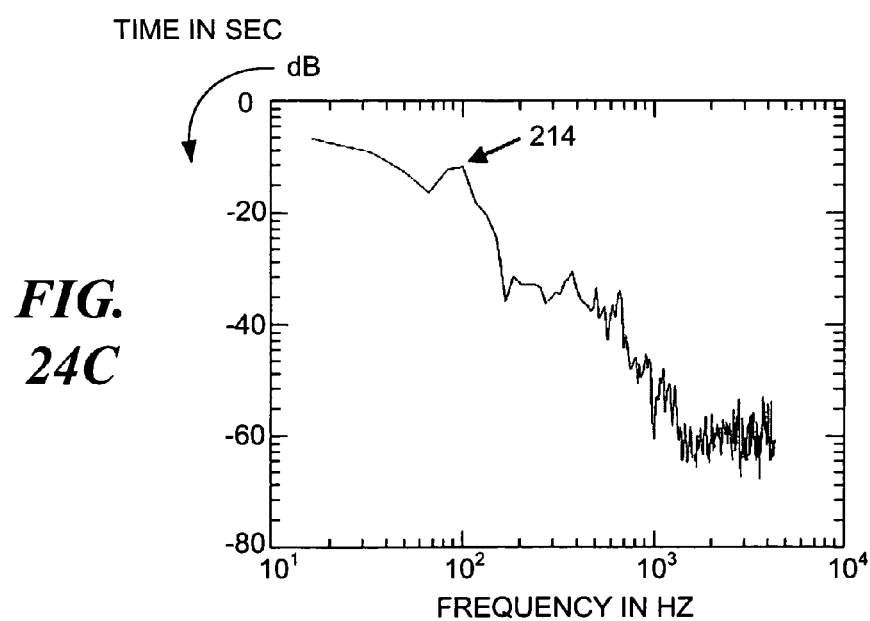
Figure 24D:
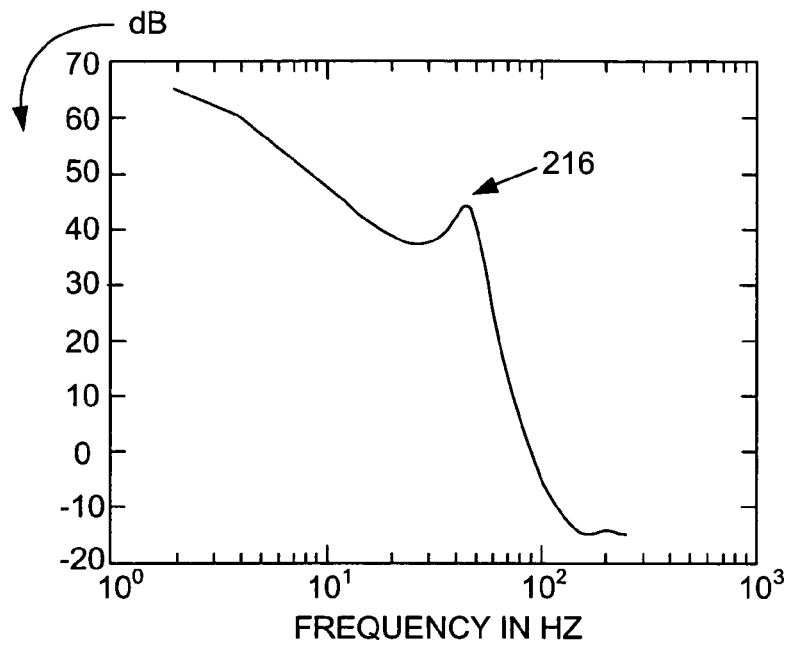
Figure 25A:
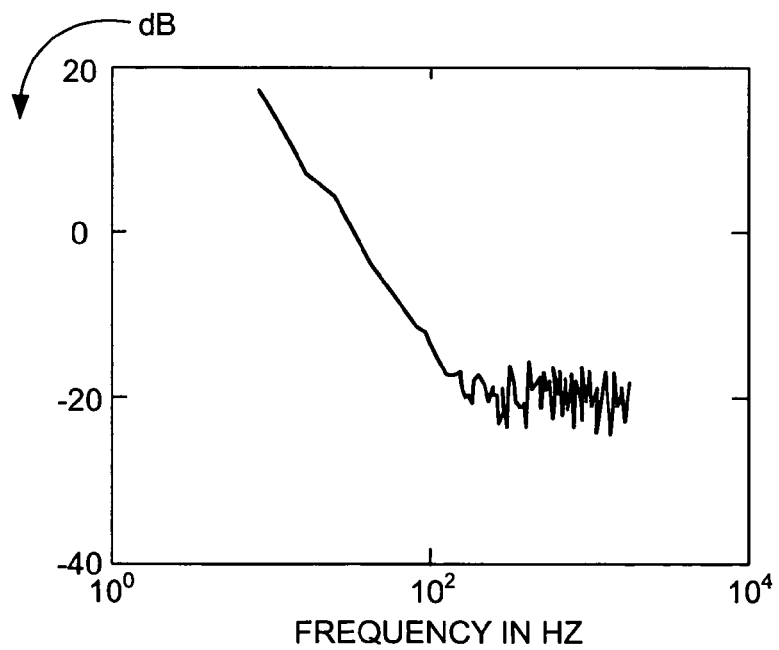
Figure 25B:
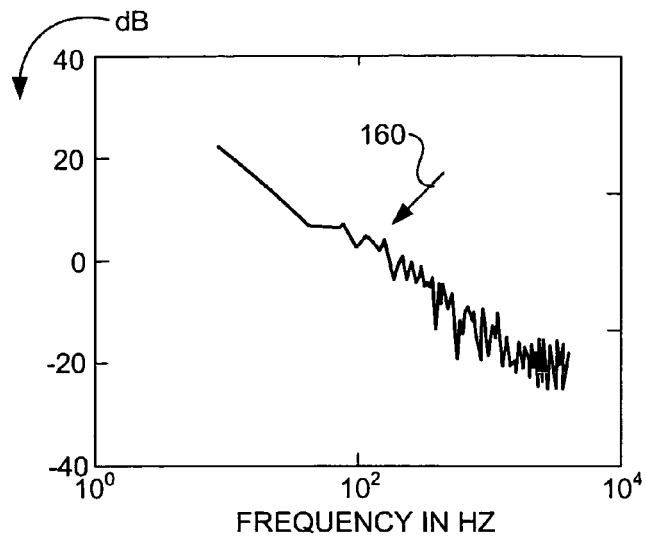
Figure 25C:
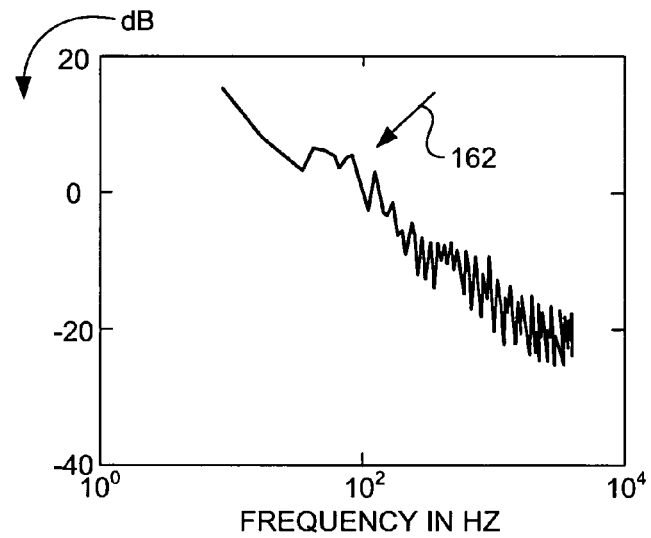
Figure 25D:
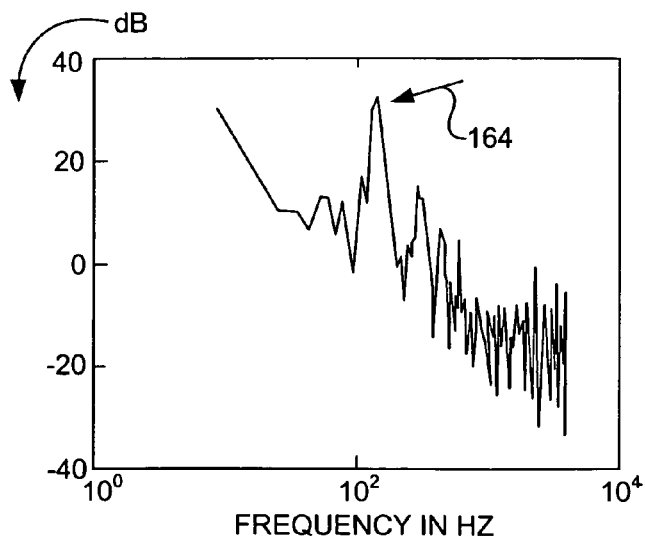
Figures 26A, 26B:
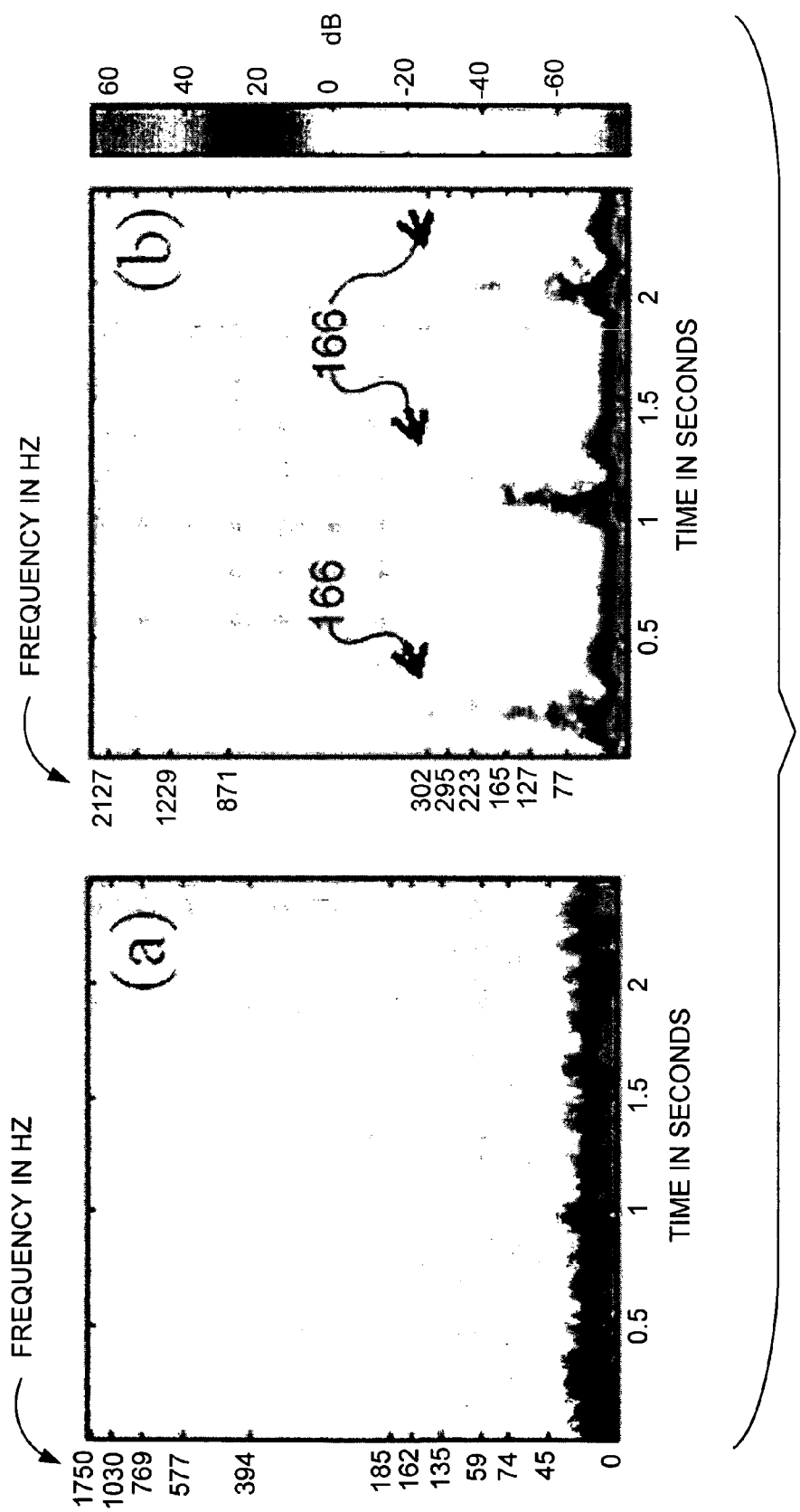
Figures 26C, 26D:
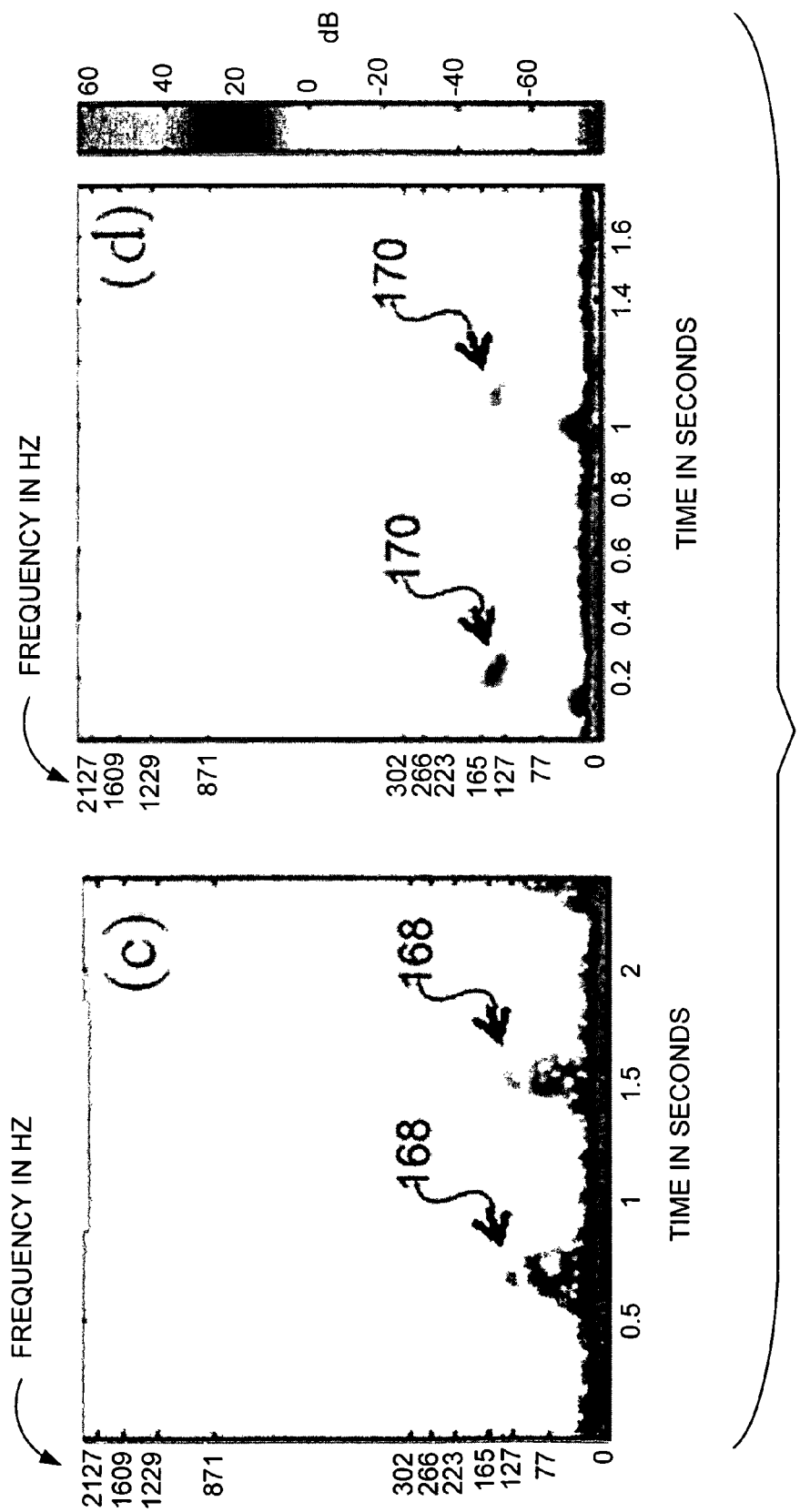
Figures 27A, 27B:
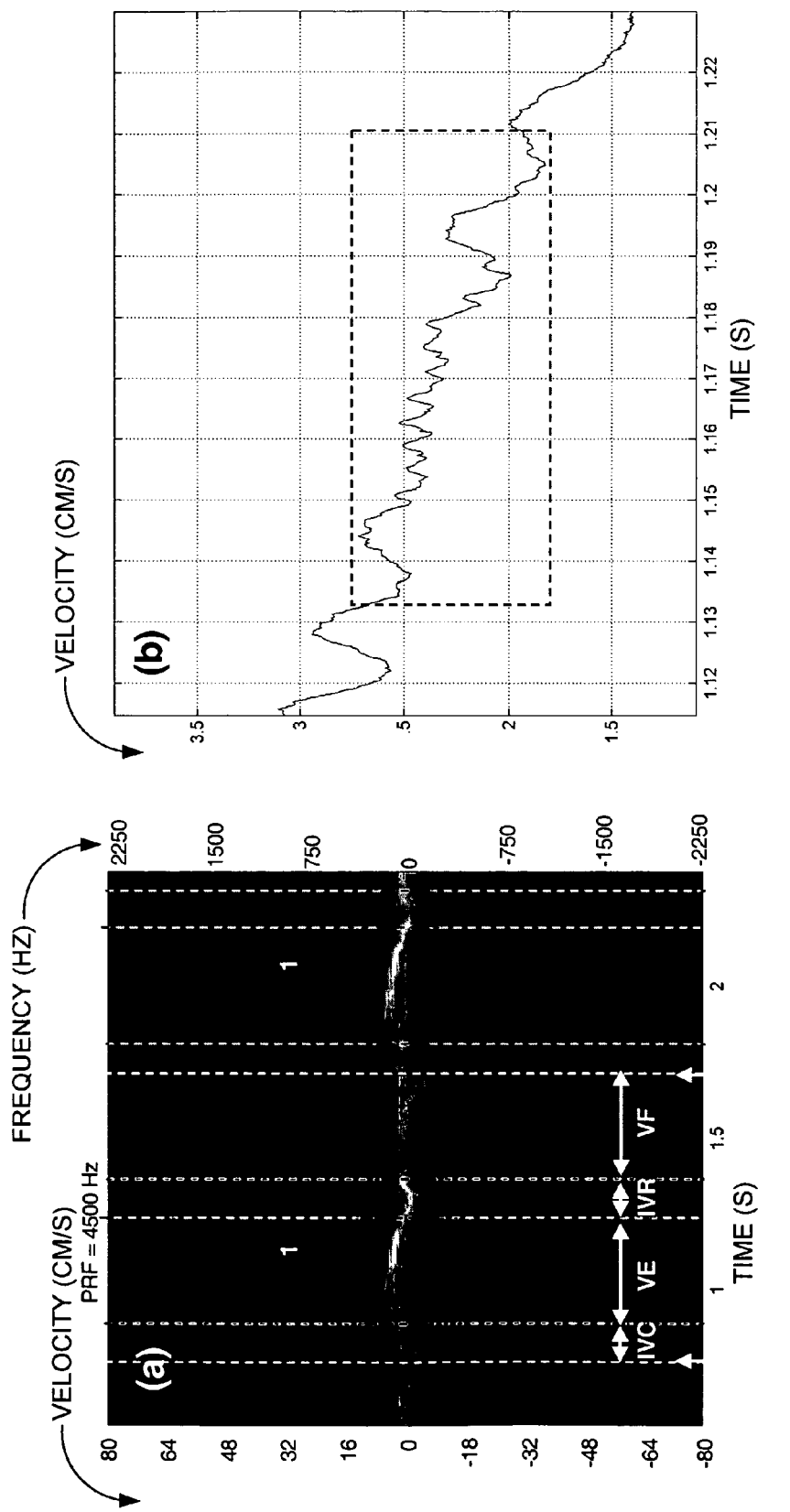
Figures 28A, 28B:
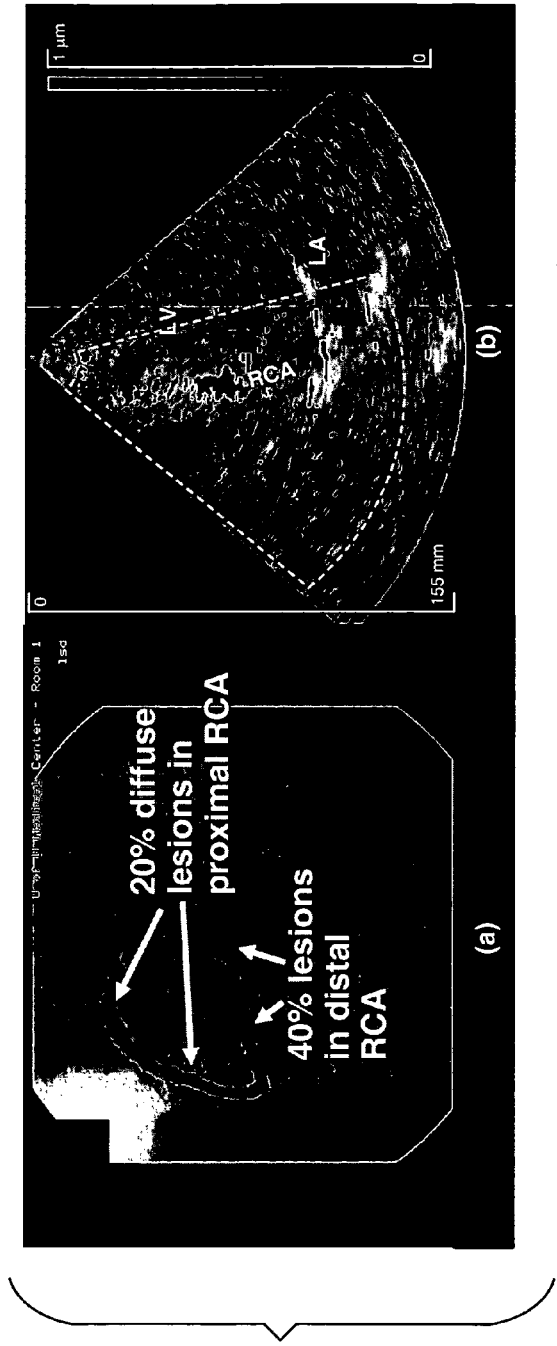
Figures 29A, 29B:
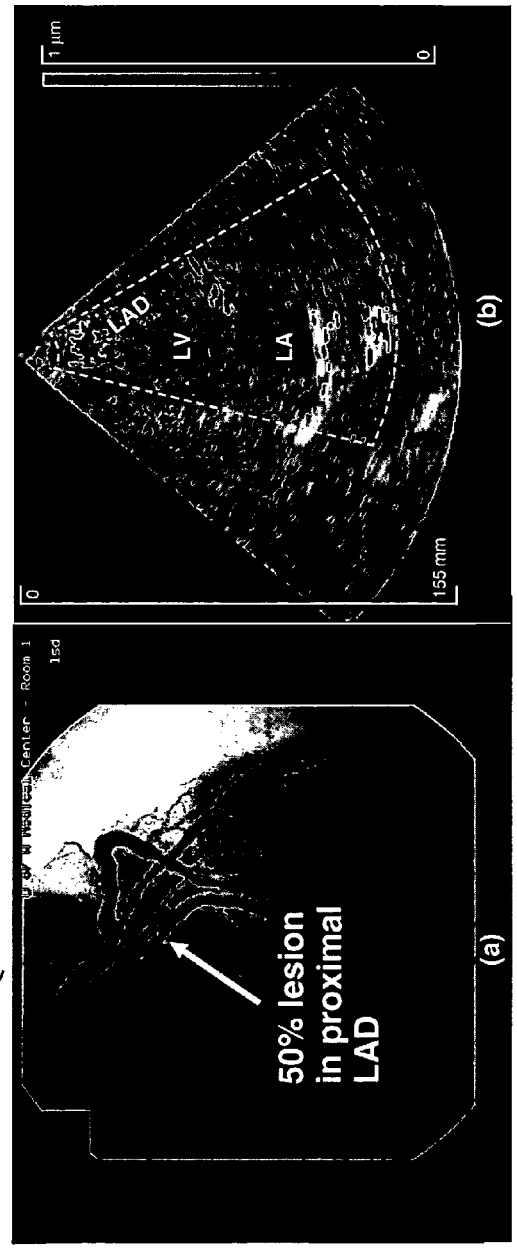

FIG. 5A graphically illustrates both a 2D Fast Fourier Transform (FFT) spectrum and a conventional Doppler spectrum of simulated received ultrasound echoes when scatterers responsible for the echoes are moving with constant velocity of 20 nm/s, the scatterer motion being along the axis of the ultrasound beam, with the Doppler spectrum being disposed to the left of the vertical axis, and the 2D FFT spectrum being disposed on the right of the vertical axis;

FIG. 5B graphically illustrates both a 2D FFT spectrum and a conventional Doppler spectrum of simulated received ultrasound echoes when scatterers responsible for the echoes are moving with a constant velocity of 20 mm/s along the axis of the ultrasound beam, and are also vibrating with a frequency of 300 Hz and an amplitude of 5 µm, with the Doppler spectrum being disposed to the left of the vertical axis, and the 2D FFT spectrum being disposed on the right of the vertical axis;

FIG. 6A graphically illustrates both a 2D FFT spectrum and a conventional Doppler spectrum of received ultrasound echoes (where the center frequency of the transmitted ultrasound signal is 5 MHz) when scatterers responsible for the echoes are moving with a constant velocity of 200 mm/s along the axis of the ultrasound beam, and also vibrating with a frequency 300 Hz and an amplitude of 5 µm, with the Doppler spectrum being disposed to the left of the vertical axis, and the 2D FFT spectrum being disposed on the right of the vertical axis;

FIG. 6B graphically illustrates both a 2D FFT spectrum and a conventional Doppler spectrum of received ultrasound echoes (where the center frequency of the transmitted ultrasound signal is 2 MHz) when scatterers responsible for the echoes are moving with a constant velocity of 200 mm/s, and also vibrating with a frequency of 300 Hz and an amplitude of 5 µm, with the Doppler spectrum being disposed to the left of the vertical axis, and the 2D FFT spectrum being disposed on the right of the vertical axis;

FIG. 7A graphically illustrates both a 2D FFT spectrum and a conventional Doppler spectrum of simulated received ultrasound echoes from a group of scatterers accelerating from 10 mm/s to 30 mm/s, with an acceleration of 5 m/s$^2$, with the Doppler spectrum being disposed to the left of the vertical axis, and the 2D FFT spectrum being disposed on the right of the vertical axis;

FIG. 7B graphically illustrates both a 2D FFT spectrum and a conventional Doppler spectrum of simulated received ultrasound echoes from a group of scatterers accelerating from 10 mm/s to 30 mm/s, with an acceleration of 5 m/s$^2$, when the scatterers are also vibrating with a frequency of 300 Hz and an amplitude of 5 µm, with the Doppler spectrum being disposed to the left of the vertical axis, and the 2D FFT spectrum being disposed on the right of the vertical axis;

FIG. 8A graphically illustrates both a 2D FFT spectrum and a conventional Doppler spectrum of simulated received ultrasound echoes when scatterers responsible for the echoes are moving with a constant velocity of 20 mm/s, the scatterer motion being perpendicular to the axis of the ultrasound beam, with the Doppler spectrum being disposed to the left of the vertical axis, and the 2D FFT spectrum being disposed on the right of the vertical axis;

FIG. 8B graphically illustrates both a 2D FFT spectrum and a conventional Doppler spectrum of simulated received ultrasound echoes when scatterers responsible for the echoes are moving with a constant velocity of 20 mm/s, the scatterer motion being perpendicular to the axis of the ultrasound beam, where the scatterers are also vibrating with a frequency of 300 Hz and an amplitude of 5 μm with the Doppler spectrum being disposed to the left of the vertical axis, and the 2D FFT spectrum being disposed on the right of the vertical axis;

FIG. 9A graphically illustrates a Radon transform of the 2D FFT spectrum of FIG. 5A;

FIG. 9B graphically illustrates a Radon transform of the 2D FFT spectrum of FIG. 5B;

FIG. 9C graphically illustrates a spectral estimate computed from the Radon transform of FIG. 9A;

FIG. 9D graphically illustrates a Doppler spectral estimate computed from the Radon transform of FIG. 9B;

FIG. 10A graphically illustrates a multifrequency spectral estimate computed from the 2D FFT spectrum of FIG. 5A;

FIG. 10B graphically illustrates a multifrequency spectral estimate computed from the 2D FFT spectrum of FIG. 5B;

FIG. 11A schematically illustrates a 3-D simulation model of scatterer distributions used to validate the use of ultrasound to image vibrations associated with a stenosis, as described herein;

FIG. 11B graphically illustrates modeled clutter motion with vibrations indicated by a boxed-in region;

FIG. 11C graphically illustrates a modeled blood flow profile;

FIG. 12A is a vibration amplitude image of a simulation model used to validate the vibration imaging techniques disclosed herein;

FIG. 12B schematically illustrates masks used for computing the sensitivity and specificity of vibration detection;

FIG. 13A graphically illustrates sensitivity versus threshold curves for phase-decomposition-based vibration detection;

FIG. 13B graphically illustrates specificity versus threshold curves for phase-decomposition-based vibration detection;

FIG. 13C graphically illustrates receiver-operating characteristic curves for phase-decomposition-based vibration detection;

FIG. 13D graphically illustrates sensitivity versus threshold curves for root-MUSIC-based vibration detection;

FIG. 13E graphically illustrates specificity versus threshold curves for root-MUSIC-based vibration detection;

FIG. 13F graphically illustrates exemplary receiver-operating characteristic curves for root-MUSIC-based vibration detection;

FIG. 14 graphically illustrates the robustness of sensitivity to increasing vibration bandwidth for the phase-decomposition and root-MUSIC algorithms disclosed herein;

FIG. 15 schematically illustrates an experimental setup in which an ultrasound probe is used to image the vibration of a plate, such a setup having been used to generate empirical evidence in support of using ultrasound to image tissue vibrations, as disclosed herein;

FIG. 16A is a B-mode ultrasound image of the vibration phantom of FIG. 15, overlaid with vibration amplitude;

FIG. 16B is a B-mode ultrasound image of the vibration phantom of FIG. 15, overlaid with vibration frequency;

FIG. 16C graphically illustrates a MUSIC pseudo-spectrum of I-Q ensemble data extracted from a portion of the ultrasound image of FIG. 16B;

FIG. 17A graphically illustrates a vibration amplitude of the plate from the experimental setup of FIG. 15 obtained using both ultrasound and an optical fiber micrometer;

FIG. 17B graphically illustrates a vibration frequency of the plate from the experimental setup of FIG. 15 obtained using both ultrasound and an optical fiber micrometer;

FIG. 17C graphically illustrates the differences between the vibration amplitude of the plate from the experimental setup of FIG. 15 obtained using both ultrasound and an optical fiber micrometer;

FIG. 17D graphically illustrates the differences between the vibration frequency of the plate from the experimental setup of FIG. 15 obtained using both ultrasound and an optical fiber micrometer;

FIG. 18 schematically illustrates an experimental setup in which an ultrasound probe is used to image a stenosis in an ex vivo artery, such a setup having been used to generate empirical evidence in support of using ultrasound to image tissue vibrations associated with a stenosis, as disclosed herein;

FIG. 19 is an image of the flow in the ex vivo artery of FIG. 18;

FIGS. 20A and 20B are respectively vibration amplitude images of an ex vivo artery obtained using the experimental setup of FIG. 18, with FIG. 20A representing a simulated stenosis of 30%, and FIG. 20B representing a simulated stenosis of 42%;

FIG. 21 graphically depicts vibration spectra from a stenosis simulated using the experimental setup of FIG. 18, the vibration spectra being generated using both pulsed-wave Doppler ultrasound and a fiber optic micrometer;

FIG. 22A is a Color-Doppler image from a stenosed vein graft in a human subject;

FIG. 22B is a vibration amplitude image of the stenosed vein graft of FIG. 9A;

FIG. 23A is a color power ultrasound image of a stenosed femoral vein graft including perivascular artifacts;

FIG. 23B is a vibration amplitude image of the stenosed femoral vein graft of FIG. 23A;

FIG. 23C is a vibration frequency image of the stenosed femoral vein graft of FIG. 23A;

FIG. 24A graphically illustrates instantaneous vessel wall position estimated using phase decomposition of pulsed wave Doppler data from a stenosed femoral vein graft;

FIG. 24B is a motion periodogram of the signal used to generate FIG. 24A;

FIG. 24C graphically illustrates a cross-sectional profile of the spectrum of FIG. 24B at a particular point in time;

FIG. 24D graphically illustrates a motion pseudo-spectrum computed using the MUSIC algorithm for 10 ensembles of color-flow ultrasound data at the same location;

FIG. 25A graphically illustrates an arterial wall displacement spectra of a normal femoral artery obtained in vivo using the techniques disclosed herein;

FIG. 25B graphically illustrates an arterial wall displacement spectra of a stenosed femoral bypass vein graft obtained in vivo using the techniques disclosed herein;

FIG. 25C graphically illustrates an arterial wall displacement spectra of a different stenosis present in the same patient as the stenosis represented in FIG. 25B;

FIG. 25D graphically illustrates an arterial wall displacement spectra of a stenosis present in another patient;

FIG. 26A graphically illustrates a time-varying wall vibration spectra of a normal artery obtained using the techniques disclosed herein;

FIGS. 26B-D graphically illustrate time-varying wall vibration spectra of stenosed blood vessels obtained using the techniques disclosed herein;

FIG. 27A is a Doppler spectrum computed using a 2D FFT method from an ultrasound image of the myocardium of a patient who has coronary artery disease, symmetric double-sided peaks being indicative of vibrations observed in the late ventricular ejection phase;

FIG. 27B graphically illustrates a time course of a wall velocity during ventricular ejection, a boxed-in region indicating high-frequency vibrations that appear to include harmonic components;

FIG. 28A is an angiographic image of a patient who has coronary artery disease, acquired in the left anterior oblique projection with caudal angulation;

FIG. 28B is a vibration amplitude image overlaid on an apical two-chamber view of the patient of FIG. 28A;

FIG. 29A is an angiographic image of a patient who has coronary artery disease, acquired in right anterior oblique projection with cranial angulation; and FIG. 29B is a vibration amplitude image overlaid on the apical two-chamber view of the patient of FIG. 29A.

DESCRIPTION

Figures and Disclosed Embodiments are not Limiting

Exemplary embodiments are illustrated in referenced Figures of the drawings. It is intended that the embodiments and Figures disclosed herein are to be considered illustrative rather than restrictive.

Tissue Vibration Imaging System

Figure 1:
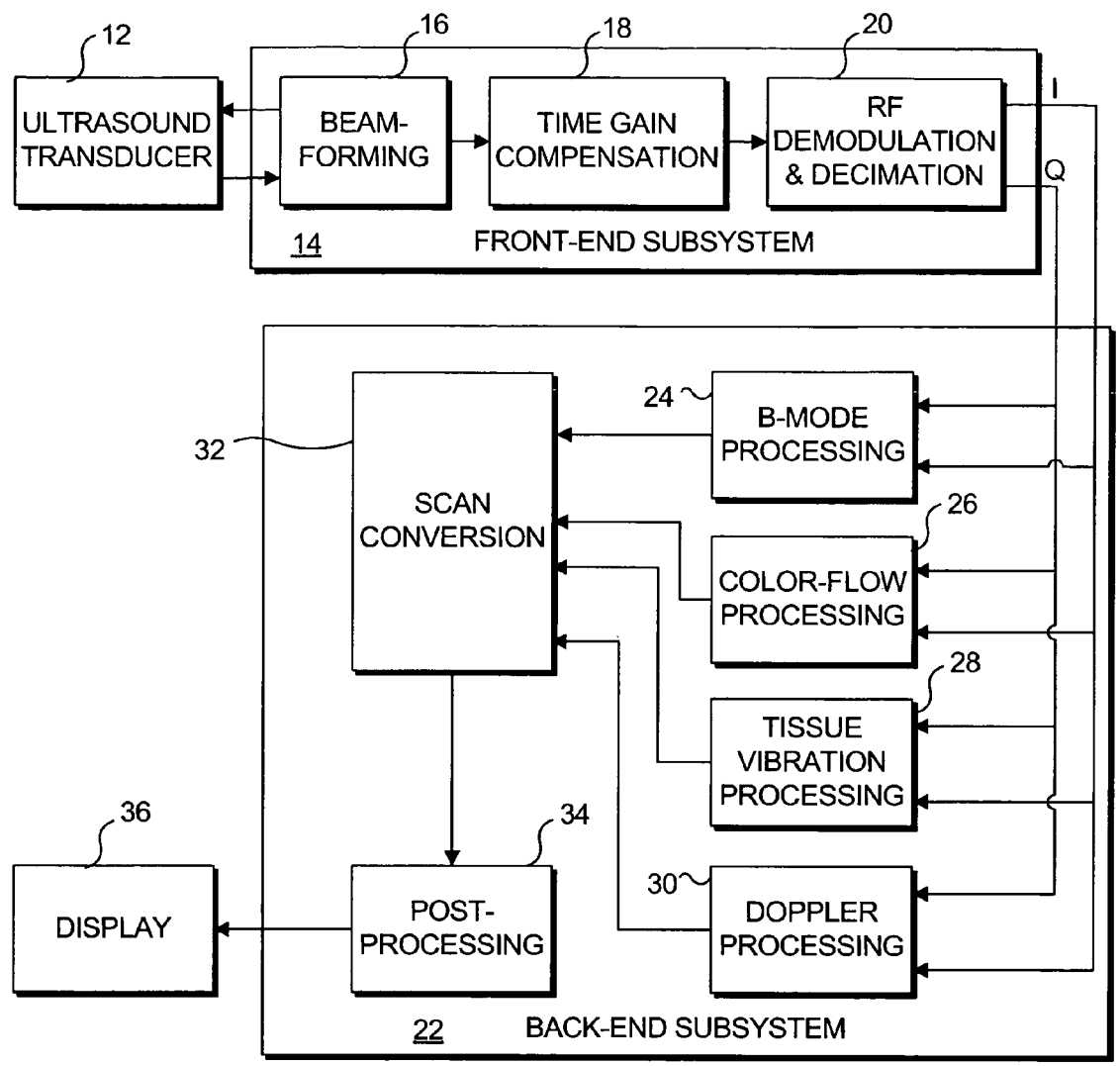
FIG. 1 is a functional block diagram of an exemplary ultrasound system that is suitable for carrying out tissue vibration imaging.

FIG. 1 is a block diagram illustrating an ultrasound system 10, which is generally similar to a conventional ultrasound system, but which has been modified to include tissue vibration imaging and is thus usable in practicing the concepts disclosed herein. Ultrasound system 10 includes an ultrasound transducer 12 that transmits a signal, which is modulated with a carrier frequency, typically 1 MHz-15 MHz, using multiple cycles (i.e., 2-20 cycles). The transmitted signal is reflected by scatterers (not shown) along the beam path and is received after a time delay, the duration of which depends upon the distance of the scatter from the transducer. In an acquisition stage, the acoustic echoes received from the tissue are converted to electrical signals by the transducer, and these signals are digitized by analog-to-digital converters (not separately shown). A front-end subsystem 14 includes a beam former 16 that performs dynamic focusing, apodization, and steering of both transmitted and received ultrasonic waveforms. Also included in front-end system 14 are a time-gain-compensation (TGC) circuit 18 that amplifies signals with a variable gain that is proportional to the depth within tissue, and a radio frequency (RF) demodulator and decimator 20 that digitally removes the high frequency carrier by quadrature demodulation and decimation, providing both in-phase (I) and quadrature (Q) samples, which may be represented as a complex quantity, $I(t)+jQ(t)$. The acquired quadrature ensemble (or color-flow) data are then processed in a back-end subsystem 22, depending on the one (or more) ultrasound mode(s) that is/are selected, e.g., B-mode, color-flow mode, tissue vibration mode, and Doppler mode.

For producing anatomic images of tissue, the signal of interest is the envelope of $I(t)+jQ(t)$. A B-mode processor 24 computes the magnitude of the echo, $B_\alpha(t)=\sqrt{I^2(t)+Q^2(t)}$ and compresses the dynamic range to make it suitable for display as a grayscale image on a monitor. The time delay introduced by the scatterers is reflected in the phase of the complex quantity $I(t)+jQ(t)$. Thus, the phase of the complex received signal provides an estimate of the instantaneous position of the scatterer. By monitoring the change of phase over time, the displacement and velocity of the scatterer can be estimated. In color-flow imaging, multiple pulses (commonly from 6 to 16 pulses) are transmitted and received along each scan line at a rate known as the pulse repetition frequency (PRF). A collection of received temporal samples from each spatial location is thus called an "ensemble." A color-flow processor 26 estimates the blood flow velocity from the ensemble of data by estimating the phase difference between the adjacent temporal samples, typically using an autocorrelation algorithm. A 2D image is created by acquiring multiple samples from different spatial locations. In Doppler mode, which is implemented with a Doppler processor 30, scanning is performed along a single scan line, and a spectrum of the blood velocity from a single spatial location is estimated from a substantially larger ensemble of data (typically, data from 64-512 pulses). Before displaying the processed image frame on a raster monitor or display 36, scan conversion is performed by a scan converter circuit 32, which converts the acquired ultrasound data from polar coordinates to the Cartesian coordinates used by the raster display. Post processing may optionally be applied by a post-processing circuit 34, to improve the quality of the displayed image, as well as to combine the anatomy and flow images on the display.

A tissue vibration processor 28 that is used to process the ultrasound data in one exemplary embodiment is shown in FIG. 1. The quadrature data ensembles are input to the tissue vibration processor. However, instead of estimating blood flow velocity from these data, the tissue vibration processor estimates the instantaneous displacement of the scattering tissue from the phase of the complex received signal. This tissue motion is referred to as clutter in conventional color-flow imaging and is suppressed using clutter filters. Typically, cardiac pulsation, respiration and transducer motion each can contribute to an observed displacement or motion of tissue. Such motion is at a low frequency of a few Hertz or less. When a stenosis is present, the tissue surrounding the stenosis vibrates locally with a frequency ranging from a few tens of Hertz to more than 1000 Hertz. By analyzing the frequencies of the different components of tissue motion, vibrations caused by stenosed blood vessels may be distinguished from clutter caused by other sources of movement. The tissue vibration processor performs this analysis by decomposing the tissue motion into the dominant motion components and identifying any motion components that appear to be at a frequency higher than that of cardiac pulsation.

It is contemplated that tissue vibration processor 28 can be implemented as an additional fixed-function circuit board or an application specific integrated circuit (ASIC) for use in conventional ultrasound machines. Optionally, the tissue vibration processor can be combined with color-flow processor 26, since both process the same data ensemble. A standalone tissue vibration imaging device can be implemented with front-end subsystem 14, B-mode processor 24, tissue vibration processor 28, and scan converter 32. Those of ordinary skill in the art will appreciate that the tissue vibration processor can be implemented in software/hardware using one or more digital signal processors (DSPs) or alternatively, in an ASIC, or even on a conventional general purpose processor chip that accesses machine language instructions stored in a memory accessed by the processor to carry out the processing steps of the tissue vibration processor.

The computational power of ultrasound machines has increased significantly in recent years, benefiting from advances in processor technology. Thus, the additional computational burden arising from executing the tissue vibration imaging algorithms discussed below can be reasonably supported in modem ultrasound machines. Previously, a programmable ultrasound signal and image processing system suitable for use as the tissue vibration processor were developed that use a new generation of high-performance multimedia processors to support all of the conventional processing modes, such as B, M, color-flow, and Doppler in software (Sikdar S, Shamdasani V, Gong L, Managuli R, Hayashi T, Mitake T, Kim Y. "*A single mediaprocessor-based programmable ultrasound system,*" *IEEE Trans Inf. Tech. Biomed* 2003; 7:64-70), and subsequently, this system was shown to be useful in implementing tissue vibration processing disclosed herein. The main strength of a programmable system is the ease of developing new modes and applications such as tissue vibration imaging without the need for hardware modifications that might be required of conventional ultrasound machines. Integrated tissue vibration imaging using the software-programmable ultrasound system has thus been effectively and beneficially used for real-time visualization of vibrations in 2D ultrasound scans.

Algorithms for Tissue Vibration Imaging

In conventional color-flow imaging, the velocity of blood flow is estimated by computing the average phase difference between multiple ultrasound echoes (typically 6-16 pulses) that are received from a sample volume. Echoes backscattered from moving tissue tend to have a significantly higher signal strength (typically 40 dB-60 dB higher), compared to the weak scattering from blood, and also have lower velocities. This high amplitude and low frequency tissue signal is commonly referred to as clutter and tends to bias the estimated blood flow velocity. Thus, clutter is suppressed using appropriate filters in conventional color flow imaging. The main components of clutter are cardiac pulsation, respiration, and transducer movement. When blood flow eddies are present, any local tissue vibrations, e.g., those caused by the blood flow eddies in stenosed blood vessels, will also be part of this clutter and would normally be suppressed in conventional ultrasound processing systems.

In accord with the concepts disclosed herein, the tissue vibrations are separated from the remaining clutter and flow signals. In achieving this function, it was recognized that the tissue vibrations and clutter produce statistically independent signals that have different frequency content. While clutter due to cardiac pulsation and breathing typically occurs at 1 Hz or less, tissue vibrations typically occur at 50 Hz or more. Other noise sources are at substantially higher frequencies. Scattering from tissue is typically more coherent compared to the scattering from blood, because the tissue scatterers are more tightly bound together and tend to move as a group. Thus, compared to the clutter from other sources and tissue vibration signals, the blood flow signal typically has a much greater frequency bandwidth. Due to its weak signal strength and greater bandwidth, blood flow signals may be considered as noise compared to the stronger and more coherent tissue vibration signals for purposes of this approach. Therefore, tissue vibrations can be distinguished from clutter and blood flow based on spectral analysis. Spectral analysis of the phase of the received ultrasound echo can be used to separate the components of the scatterer motion, ignoring the scattered signal strength, whereas spectral analysis of the complex ultrasound echo considers both the signal strength and the motion components.

Due to the limited number of temporal ultrasound samples (6-16 pulses) preferably used in implementing the present concepts, conventional clutter filtering and spectral estimation techniques lack sufficient resolution to discriminate between the tissue vibrations and normal clutter from such a short temporal record. Therefore, high-resolution spectral estimation techniques were developed to carry out this function.

With respect to imaging vibrations associated with stenosed blood vessels, two high-resolution spectral estimation techniques were identified as suitable for this purpose, including eigen decomposition-based spectral estimation, which models the signal as an optimum set of orthogonal components, and autoregressive spectral estimation, which models the signal as the output of an autoregressive linear prediction filter driven by white Gaussian noise. Accordingly, three signal processing algorithms were developed for isolating tissue vibrations associated with stenoses (two based on eigen decomposition and one based on autoregression). The first algorithm is based on an eigen decomposition-based spectral analysis of the phase of the received ultrasound echo; the second algorithm is based on an eigen decomposition-based spectral analysis of the complex ultrasound echo; and, the third algorithm is based on an autoregressive spectral analysis of the complex ultrasound echo. Since eigen decomposition is a computationally-intensive operation, an approximate eigen decomposition utilizing iterative QR factorization is used as a computationally-efficient algorithm.

Signal Model Developed to Image Vibrations Associated with Stenosed Blood Vessels To model the received signal from vibrating tissue, the tissue being imaged is approximated with S point scatterers having uniform motion and randomly distributed at locations $(\vec{r}_s = [r_s]\hat{e}_r + [\psi_s]\hat{e}_\psi + [\phi_s]\hat{e}_\phi)$, $s=1 \ldots S$, in a sample volume where $(\hat{e}_r, \hat{e}_\psi, \hat{e}_\phi)$ denote the unit direction vectors in spherical coordinates. The instantaneous position of the scatterers, $v(\vec{r}, t)$, is given by:

$$v(\vec{r}, t) = \sum_s \delta(\vec{r} - \vec{r}_s(t)) \quad (1)$$

$$\vec{r}_s(t) = [r_s - d_r(t)]\hat{e}_r + [\psi_s - d_\psi]\hat{e}_\psi + [\phi_s - d_\phi]\hat{e}_\phi$$

where $(d_r(t), d_\psi(t), d_\phi(t))$ denote the displacement as a function of time. If the scattering from the sample volume is uniform with $\alpha$ as the average scattering coefficient, then the scattering function of the sample volume is $\alpha v(\vec{r}, t)$. The complex received signal from the sample volume, $y(\tau, t)$, can then be modeled as a convolution of the pulse echo spatial impulse response, $h_{pe}(\vec{r}, \tau)$, of a single point scatterer, the temporal response of the transducer, $x(\tau)$, and the scattering function, $\alpha v(\vec{r}, t)$.

$$y(\tau, t) = h_{pe}(\vec{r}, \tau) *_\tau x(\tau) *_r \alpha v(\vec{r}, t) + n(\tau, t) \quad (2)$$

$$x(\tau) = x_0(\tau) e^{j2\pi f_0 \tau}$$

where the time indices $r$ and $t$ refer to "fast" time and "slow" time, respectively, $f_0$ is the center frequency of the transducer, and $n(\tau,t)$ is white thermal noise. Combining Eqs. (1) and (2) results in:

$$y(\tau, t) = \alpha \sum_s h_{pe}\left(\vec{r}_s, (t), \tau - \frac{2(r_s - d_r(t))}{c}\right) \quad (3)$$

$$x_0\left(\tau - \frac{2(r_s - d_r(t))}{c}\right) e^{j2\pi f_0 \left(\tau - \frac{2(r_s - d_r(t))}{c}\right)} + n(\tau, t)$$

where c is the speed of sound and $$\frac{2(r_s - d_r(t))}{c}$$

is the two-way pulse propagation time between the transducer and each point scatterer. The scatterer displacement for vibrations is small compared to the spatial size of the pulse echo spatial impulse response and the envelope of the transducer response. Thus, the "slow" time variations in the first two terms may be neglected and Eq. (3) can be simplified to:

$$y(\tau, t) = \left\{ \alpha \sum_s h_{pe}\left(\vec{r}_s, \tau - \frac{2r_s}{c}\right) x_0\left(\tau - \frac{2r_s}{c}\right) e^{j2\pi f_0\left(\tau - \frac{2r_s}{c}\right)} \right\} e^{j2\pi f_0 \frac{2d_r(t)}{c}} + n(\tau, t) \quad (4)$$

$$= A(\tau) e^{j2\pi f_0 \frac{2d_r(t)}{c}} + n(\tau, t)$$

where $A(\tau)$ is the complex amplitude of the scattered signal. It is apparent that the complex received signal is phase modulated with the instantaneous radial displacement.

If the scatterers in the sample volume are all vibrating radially in a simple harmonic fashion with peak displacement $\alpha_0$ and at a frequency $f_{vib}$, the tissue displacement due to cardiac pulsation, breathing, and other tissue movement (i.e., clutter or noise) relative to the transducer is $d_{tiss}(t)$. This motion will hereinafter be referred to as the "clutter motion." Then, the combined displacement can be considered to be a superposition, as follows:

$$d_r(t) = d_{tiss}(t) + \alpha_0 \sin(2\pi f_{vib} t) \quad (5)$$

An ensemble of ultrasound pulses is transmitted in the same direction at a rate known as the pulse repetition frequency (PRF). Then, the complex received signal from the $m^{th}$ pulse transmission, $y(\tau, m)$, is:

$$y(\tau, m) = A(\tau) e^{j2\pi f_0\left(\frac{2d_{tiss}(mT_{PRF})}{c} + \frac{2a_0 \sin(2\pi m T_{PRF} f_{vib})}{c}\right)} + n(\tau, m) \quad (6)$$

where $T_{PRF}$ is the pulse repetition interval. The Fourier transform of the phase-modulated complex received signal is a Bessel series:

$$Y(\tau, f) = A(\tau)\left\{\Im\left(e^{j2\pi f_0 \frac{2d_{tiss}(mT_{PRF})}{c}}\right) *_f \Im\left(e^{j2\pi f_0 \frac{2a_0 \sin(2\pi m T_{PRF} f_{vib})}{c}}\right)\right\} + N(\tau, f) \quad (7)$$

$$= A(\tau)\left\{c(f) *_f \sum_{n=-\infty}^{n=\infty} j^n J_n(\beta)\delta(f - 2\pi n T_{PRF} f_{vib})\right\} + N(\tau, f)$$

$$= A(\tau) \sum_{n=-\infty}^{n=\infty} j^n J_n(\beta) c(f - 2\pi n T_{PRF} f_{vib}) + N(\tau, f)$$

where $J_i$ are Bessel functions of the first kind, $$\beta = \frac{4\pi f_0 a_0}{c},$$

$\delta$ is the Dirac delta function, and $c(f)$ is the spectrum of the clutter motion (the clutter spectrum), and $N(\tau, f)$ is the noise spectrum.

Figure 2:
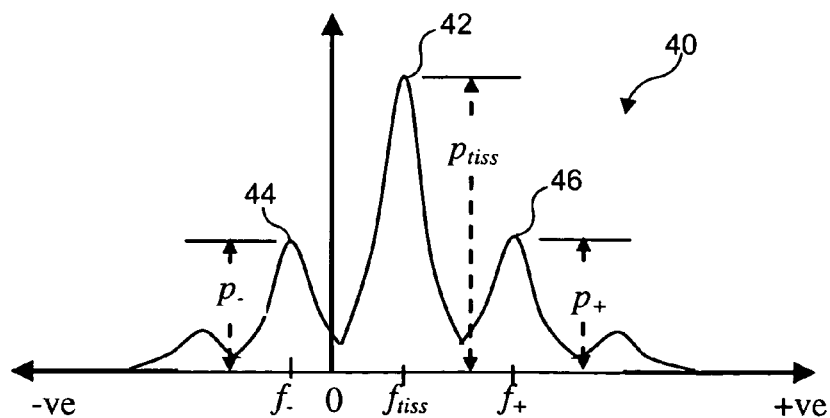
FIG. 2 is a graph of an expected Doppler spectrum (i.e., frequency vs. power) from a vibrating sample volume.

FIG. 2 illustrates a typical power spectrum 40 of the ultrasound signal when a tissue vibration is present. The spectrum includes multiple copies of the clutter spectrum separated by the vibration frequency, as indicated by Eq. (8), which is presented below. A low frequency peak 42 at $f_{tiss}$ corresponds to the clutter spectrum, while symmetric peaks $f_-$ and $f_+$ indicated respectively by reference numbers 44 and 46 correspond to vibration, and $p_{tiss}$, $p_+$, and $p_-$, are the corresponding peak powers. The frequency peaks at $f_+$ and $f_-$ are referred to herein as a "matching pair." For small-amplitude vibrations, higher-order terms can be ignored; thus, most of the spectral energy will be present in the three frequency peaks, $f_-$, $f_{tiss}$, and $f_+$, respectively. Since $$\left|\frac{J_1(\beta)}{J_0(\beta)}\right| \approx \frac{\beta}{2},$$

the ratio of the power in the frequency peaks can provide an estimate of the vibration amplitude. Therefore, the vibration frequency and amplitude may be estimated from the power spectrum as follows:

$$\hat{f}_{vib}^{power} = \left|\frac{f_+ - f_-}{2}\right|; \quad (8)$$

$$\hat{a}_{vib}^{power} = \frac{c}{4\pi f_0} \sqrt{\frac{p_+ + p_-}{2p_{tiss}}}$$

These estimators are referred to herein as the "spectral frequency estimator" and the "power ratio amplitude estimator," respectively. Alternatively, the vibration frequency and amplitude may be estimated from the residual phase $\{\phi(k)\}_{k=1}^{\epsilon}$ of the ultrasound signal after suppressing the effects of clutter motion. A coarse computationally-efficient estimate of the frequency of the dominant components, $\hat{f}_{vib}$, can be obtained by counting the zero crossings, $N_{zero}$, in the residual phase. This estimate can be further refined by interpolating the residual phase to compute the mean period of oscillation. The vibration amplitude may be estimated by the variance of the residual phase. These estimators are defined as follows:

$$\hat{f}_{vib}^{phase} = \left|\frac{f_+ - f_-}{2}\right|; \quad (9)$$

$$\hat{a}_{vib}^{phase} = \frac{c}{4\pi f_0} \text{var}(\phi(k))$$

and are respectively referred to herein as the "zero-crossing frequency estimator" and the "phase variance amplitude estimator."

For real-time tissue vibration imaging, only a short ensemble of ultrasound data (typically, 6-16 pulses or echoes)

from each sample volume in a region of interest may be available for processing. Conventional color-flow imaging systems utilize clutter filtering to suppress the clutter, while retaining the blood flow. However, due to the small number of temporal samples, the conventional clutter filtering-based approach, or a Fourier-based approach lacks sufficient resolution to discriminate between the tissue vibrations, blood flow, and clutter. A parametric approach that utilizes the characteristics of the vibration signal appears better suited to make this distinction. Three parametric approaches may be taken, based on the model of the ultrasound signal in Eqs. (6) and (7), including: (a) estimation of a pair of complex exponentials in noise; (b) autoregressive modeling; and, (c) decomposition of the phase of the ultrasound signal. In the following section, exemplary vibration detection algorithms based on these three parametric approaches are described in greater detail. One method of producing the complex ultrasound signal in Eq. (4) is a quadrature demodulation of the received ultrasound signal. An alternative method is to compute the time delays producing the phase variations in Eq. (4) by processing the received RF ultrasound data using a cross correlation technique.

Vibration Imaging Using Estimation of Complex Exponentials in Noise

Using the inverse Fourier transform of the Bessel expansion in Eq. (7), Eq. (6) is expanded, as follows:

$$y(\tau, m) = A(\tau)\left\{e^{j2\pi f_0 \frac{2d_{tiss}(mT_{PRF})}{c}}\right\}\left\{\sum_{n=-\infty}^{n=\infty} J_n(\beta)e^{j2\pi n f_{vib}T_{PRF}+jn\pi}\right\} + n(\tau, m) \quad (10)$$

$$= A(\tau)e^{j2\pi f_0 \frac{2d_{tiss}(mT_{PRF})}{c}}\left\{\sum_{n=0}^{n=\infty} J_n(\beta)[e^{j2\pi n f_{vib}T_{PRF}} - e^{-j2\pi n f_{vib}T_{PRF}}]\right\} + n(\tau, m)$$

Thus, the ultrasound signal can be modeled as a sum of complex exponentials embedded in noise. As can be seen from the expression enclosed by square brackets in Eq. (10), vibrations correspond to matching pairs of complex exponentials. In contrast, the complex exponentials corresponding to clutter motion will typically not have such matching pairs of frequencies. The frequencies ($f_{tiss}$, $f_+$, $f_-$) may be estimated using the root-MUSIC and ESPRIT algorithms (disclosed by P. Stoica and R. Moses in "Introduction to Spectral Analysis," Upper Saddle River, N.J.: Prentice-Hall, 1997). Vibrations may then be detected using a matching peak criterion $|f_+ + f_- - 2 f_{tiss}| < F_{threshold}$, and the vibration amplitude and frequency can be estimated using Eq (9), which is set forth above. The steps of the algorithm are described in more detail below, in regard to FIG. 3A. Based on this criterion, vibrations can be detected and distinguished from clutter motion. Any blood flow signals may be considered as part of the noise spectrum.

Figure 3A:
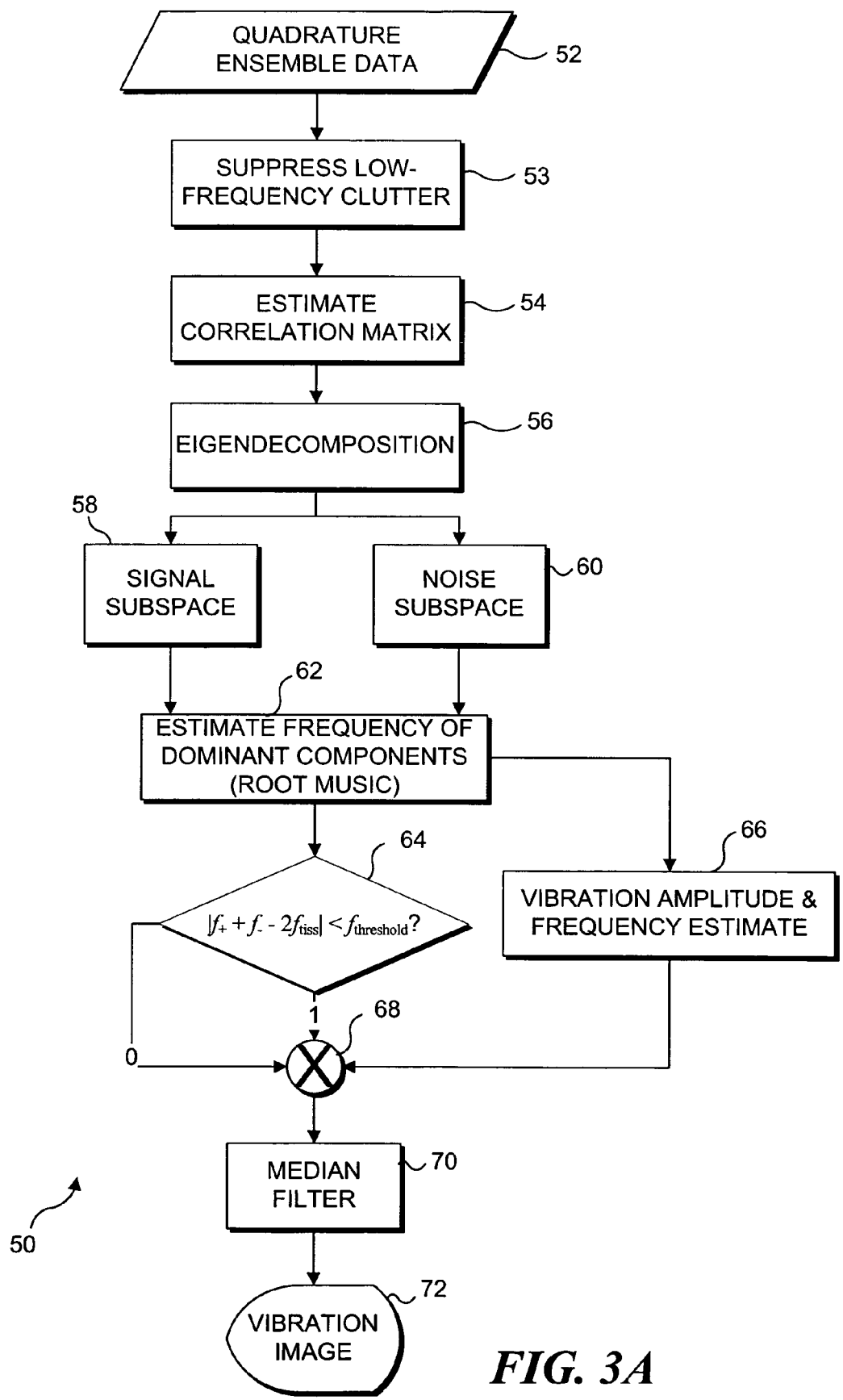
FIG. 3A is a flow chart showing the logical steps of an exemplary subspace-based algorithm for creating a vibrating tissue image in which a stenosis is evident.

FIG. 3A illustrates a flow chart 50 that shows the logical steps involved in a first algorithm for estimating the tissue vibrations based upon a pair of complex exponentials in clutter or noise, which are normally excluded from color-flow processing. The procedure begins with a quadrature-demodulated ensemble of 2D ultrasound data 52.

In a step 53, low frequency clutter due to cardiac pulsation, pulsatile blood vessel wall motion, and respiration is suppressed. In one embodiment, this step may include down mixing with the mean clutter velocity estimated using the autocorrelation method. In another embodiment, the low frequency motion may be suppressed by filtering. In yet another embodiment, the motion of the surrounding tissue may be used to form an estimate of the low frequency tissue motion by analyzing the principal motion components.

In a step 54, a correlation matrix is estimated from the color-flow data. In a step 56, the correlation matrix is employed to carry out an eigen decomposition, producing a signal subspace 58 and a noise subspace 60. Using the signal subspace and the noise subspace, the frequency of the dominant components is estimated in a step 62, by employing the root-MUSIC and ESPRIT algorithms, as noted above. A decision step 64 then determines if each dominant component is double-sided, while a step 66 estimates the vibration amplitude and frequency of each dominant component using Eq. (8). If a dominant component is not double-sided (i.e., is not a potential tissue vibration component), decision step 64 returns a "zero," while if the dominant component is double-sided, the decision step returns a one. A multiplier 68 then multiplies the output of decision step 64 by the vibration amplitude and frequency estimate for the dominant component, yielding a null if the dominant component is not a tissue vibration component, and otherwise returning the estimate of vibration amplitude and frequency of the dominant component. A median filter 70 then filters isolated falsely-detected vibrations and other undesired noise from the results, so that the remaining vibration image indicating a stenosis site is displayed in a step 72.

Vibration Imaging Using an Autoregressive Signal Model.

The ultrasound signal from vibrations can be modeled as the output of a $p^{th}$-order autoregressive linear prediction filter with white Gaussian noise having a variance $\sigma^2$, as the input, as follows:

$$y(\tau, m) = \sum_{k=1}^{p} a_{m-k}(\tau)y(\tau, m-k) + n(\tau, m) \quad (11)$$

The linear prediction coefficients, $\alpha_k(\tau)$, can be computed using either a least-squares minimization of the prediction errors or using the computationally-efficient Burg algorithm, as explained by Stoica and Moses in the above-referenced paper. A high-resolution spectral estimate can then be obtained from this autoregressive model as follows:

$$\|Y(\tau, f)\| = \frac{\sigma^2}{\left|1 + \sum_{j=1}^{p} a_k(\tau)e^{-j2\pi k f}\right|^2} \quad (12)$$

From Eq. (8), the presence of symmetric matching pairs of frequency peaks in the power spectrum around the clutter motion peak may be detected as a vibration. As before, any flow signals may be regarded as noise. For ultrasound signals from vibrations, the power spectrum in Eq. (13) will have frequency peaks ($f_{tiss}$, $f_+$, and $f_-$) at the local minima of the polynomial $$A(\tau, f) = \left|1 + \sum_{j=1}^{p} a_k(\tau)e^{-j2\pi kf}\right|.$$

Vibrations can be detected using a matching peak criterion $|f_+ + f_- - 2f_{tiss}| < F_{threshold}$, and the vibration amplitude and frequency can be estimated using Eq. (9). The steps of this algorithm are described in more detail below, in connection with FIG. 3B.

Figure 3B:
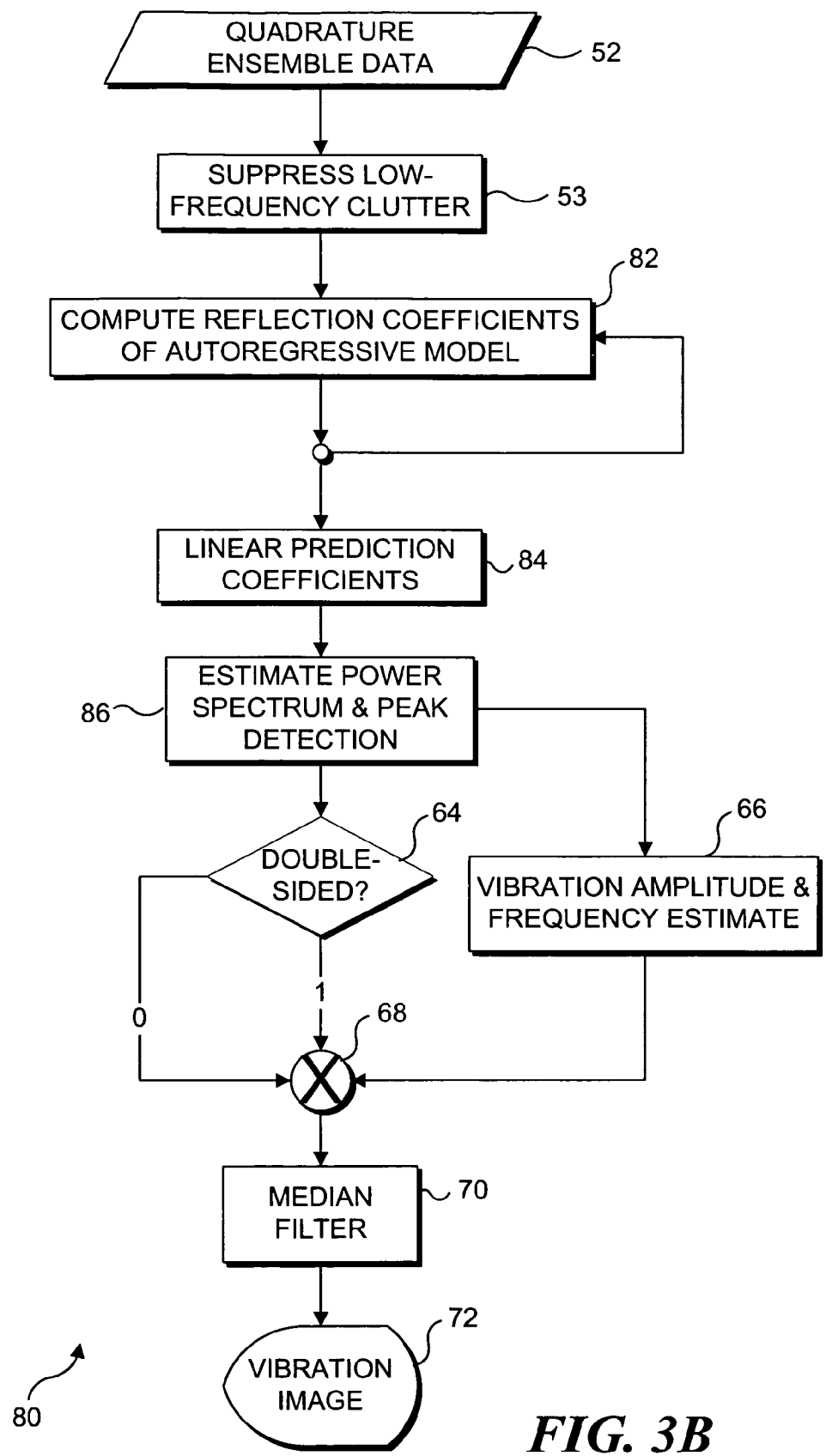
FIG. 3B is a flow chart showing the logical steps of an alternative exemplary algorithm that uses autoregression for creating a vibrating tissue image in which a stenosis is evident.

As shown in a flow chart 80 in FIG. 3B, the second alternative algorithm also begins with quadrature-demodulated ensemble data set 52. Again, in step 53, low frequency clutter due to cardiac pulsation, pulsatile blood vessel wall motion, and respiration is suppressed. In one embodiment, this step may include down mixing with the mean clutter velocity estimated using the autocorrelation method. In another embodiment, the low frequency motion may be suppressed by filtering. In yet another embodiment, the motion of the surrounding tissue may be used to form an estimate of the low frequency tissue motion by analyzing the principal motion components.

In a step 82, reflection coefficients are computed for each ensemble of the quadrature-demodulated data. Using the reflection coefficients, linear prediction coefficients are determined in a step 84. In a step 86, the power spectrum is estimated from the linear prediction coefficients and the peaks in the power spectrum are detected. Again, decision step 64 determines if the peaks thus identified are for tissue vibration by determining if they are double-sided and returning a zero if not, and a one, if so. Also, step 66 provides for estimating the vibration amplitude and frequency at each of these peaks, and the results from decision step 64 are multiplied by the estimated amplitude and frequency in multiplier 68. Median filter 70 is then applied to the results, and the filtered image data are displayed as a vibration image, in step 72.

Vibration Imaging Based on Phase Decomposition

A third algorithm for detection and imaging of vibrations can be based on the phase ultrasound signal. As shown in Eq. (7), vibrations will produce an oscillatory signature in the phase, which will typically not be present in the case of clutter motion. Although flow signals may have oscillatory phase, the echoes from vibrating tissue are expected to be more coherent than those from flow. Thus, their phase may be modeled by a smaller number of dominant components. Accordingly, a vibration detection algorithm can also be based on decomposition of the phase of the ultrasound signal into its dominant components and testing for oscillatory phase. Alternatively, instead of using quadrature-demodulated ultrasound data, the phase can be estimated from RF ultrasound data by estimating the time delays between a pair of RF ultrasound data.

Any linear time-varying motion is first suppressed by down mixing the ensemble of 2D ultrasound data with the mean clutter velocity, estimated using the conventional autocorrelation method. The phase of the ensemble of 2D ultrasound data is then computed, and the mean phase is subtracted to suppress the effect of the stationary echo. The residual phase is then decomposed into its dominant components using a method similar to principal component analysis. The first step of the decomposition involves the estimation of the correlation matrix of the residual phase using the modified covariance method (Marple, 1987). An approximate eigen decomposition can then be performed using iterative QR factorization of the correlation matrix. The approximate eigen values, $\lambda_i$, may be estimated by the diagonal elements of the upper triangular matrix $R_k$ after the $k^{th}$ iteration. The eigenvectors are arranged in order of decreasing eigen values. The eigen values are a measure of the signal energy contributed by the corresponding eigenvector. Thus, the fraction of the total signal energy contained in the p dominant components can be estimated using $$E_p = \frac{\sum_{i=1}^{p} \lambda_i^2}{\sum_{i=1}^{N+1} \lambda_i^2}.$$

Therefore, noise and blood flow can be suppressed by only employing values of $E_p$ that exceed a threshold criterion, $E_p > E_{threshold}$. To further separate tissue vibrations from clutter motion, the fact that tissue vibrations have a higher frequency compared to clutter motion is applied. Vibrations can then be separated from clutter using a frequency threshold criterion $f_{vib} > F_{threshold}$, where $F_{threshold}$ is chosen so that at least one half of one period of the vibration is contained in an ensemble. The vibration frequency and amplitude may be estimated using Eq. (10). The steps of this algorithm are described in more detail below, in connection with FIG. 3C. While developed to image vibrations associated with internal bleeding, this exemplary algorithm has also been shown to be effective in imaging vibrations associated with stenosed blood vessels, as is discussed in detail.

A flow chart 90a illustrates the logical steps of the third algorithm. Again, staffing with quadrature ensemble data 52, step 53 suppresses low frequency clutter due to cardiac pulsation, pulsatile blood vessel wall motion, and respiration. In one embodiment, this step may include down mixing with the mean clutter velocity estimated using the autocorrelation method. In another embodiment, the low frequency motion may be suppressed by filtering. In yet another embodiment, the motion of the surrounding tissue may be used to form an estimate of the low frequency tissue motion by analyzing the principal motion components.

A step 94 provides for computing an unwrapped phase of the quadrature ensemble or color flow data, and then subtracting the mean clutter velocity from the unwrapped phase, resulting in a residual phase. As explained above, instead of determining the phase from quadrature-demodulated data, the phase can be determined from RF ultrasound data by estimating time delays between a pair of RF ultrasound data. Using the residual phase, a step 96 estimates a correlation matrix, which is then used to carry out a QR factorization in a step 98a, yielding an eigen value estimate 100a, an eigenvector estimate 102a, and a vibration amplitude and frequency estimate 104a, which are determined using Eq. (10), as noted above. Using the eigen value estimate, a decision step 106a determines if the total energy contained in the p dominant component is greater than a predefined threshold, T. If so, decision step 106a returns a zero if not, and a one if so. Similarly, a decision step 108a determines if the estimate eigenvector has a frequency that is greater than a predefined threshold, F. If so, decision step 108a returns a one, and if not, a zero. The results of decision steps 106a and 108a, and the estimated vibration amplitude and frequency of the dominant components are then multiplied together by a multiplier 110, so that if either of the decision blocks has returned a zero, the result is null, but if neither has returned a zero, the estimated vibration amplitude and frequency from step 104a are returned. Again, median filter 70a is applied to the estimated amplitude and frequency, providing filtered results that are displayed as the vibration image, indicating a site of stenosis, in a step 72a.

Using the Algorithms Described Above to Image and Analyze a Stenosis

Figure 4:
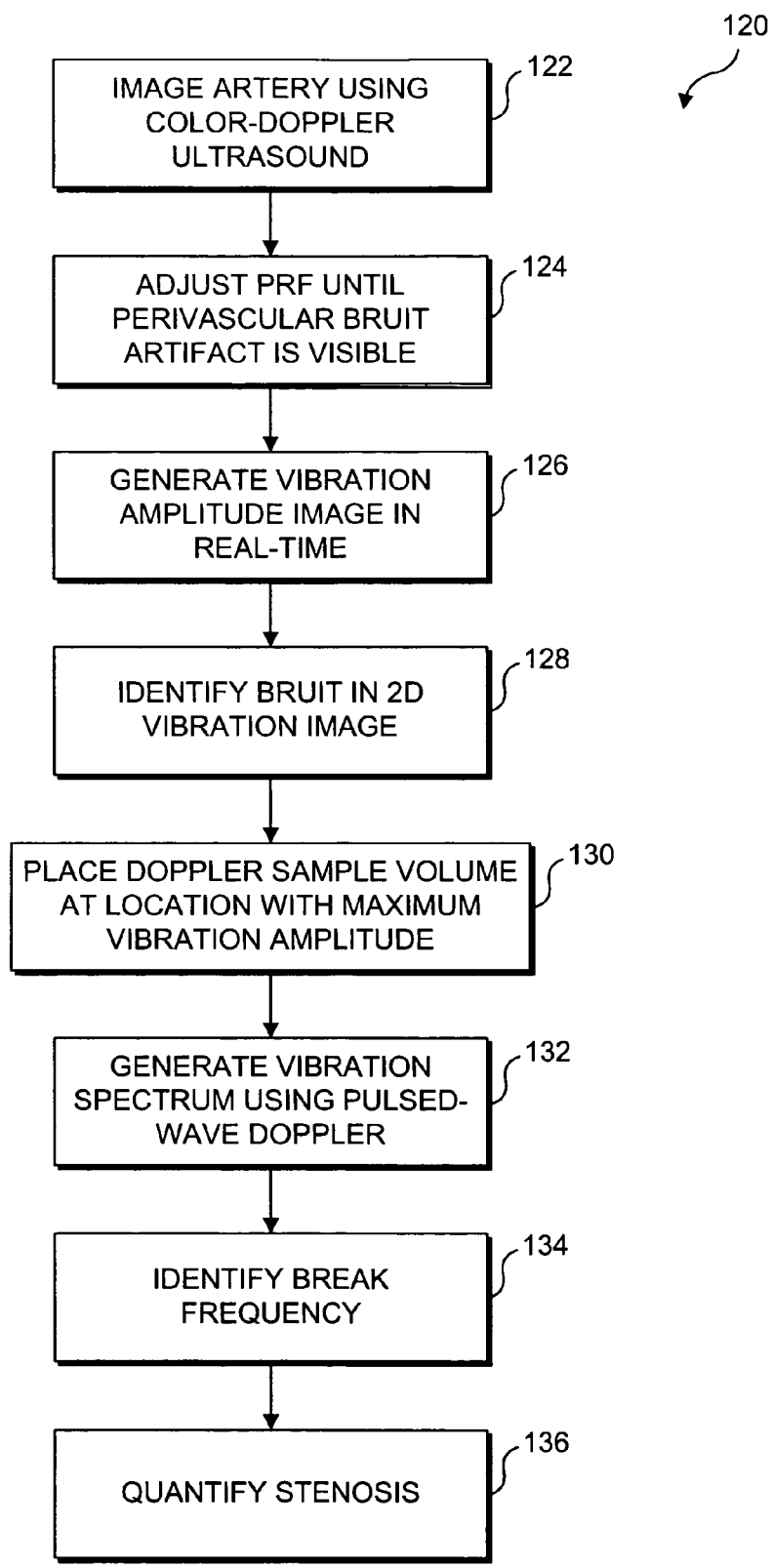
FIG. 4 is a flow chart showing the logical steps of a method for localizing and grading arterial stenoses using a vibrating tissue image generated using ultrasound.

FIG. 4 illustrates a flow chart 120 that shows the logical steps involved in using ultrasound to localize and quantify arterial stenoses. The procedure begins with a step 122, wherein a blood vessel is imaged using color-Doppler ultrasound. In a step 124, the pulse repetition frequency (PRF) is adjusted until a perivascular artifact of a bruit is visible. In a step 126, a vibration amplitude image is generated in real time, generally as described above. In a step 128, the location of the bruit in the 2D vibration image is identified. In a step 130, a Doppler sample volume is placed at the bruit proximate the maximum vibration amplitude. In a step 132, a vibration spectrum is generated from the pulsed-wave Doppler data (again, using the techniques described above). In a step 134 the "break" frequency of the vibration spectrum is noted, while in a step 136 the stenosis is quantified.

Detectable Vibration Amplitudes and Frequencies

In experiments using a physical phantom model, tissue vibrations with a peak amplitude of about 1 μm have been accurately detected. The minimum detectable vibration amplitude depends upon the noise level and dynamic range of the phase of the received ultrasound echo. In modern ultrasound machines, the phase can have a dynamic range of 96 dB or more (for 16-bit quadrature-demodulated data) and the signal typically exceeds the electronic and thermal noise level by 80 dB or more. Therefore, from Eq. (4), vibrations as small as 50 nm may theoretically be detected using a 5 MHz ultrasound transducer. Practically, the attenuation of the ultrasound signal will reduce the dynamic range and limit the minimum detectable amplitude in deep tissue to ~0.5 μm.

The detectable vibration frequencies depend upon the choice of PRF, i.e., on $F_{PRF}$. A PRF that is too low compared to the vibration frequency would lead to aliasing, while selecting a PRF that is too high will fail to detect low-frequency vibrations. A vibration can be detected only if at least half of one vibration cycle is captured within the temporal window corresponding to an ensemble. Thus, all vibrations with frequency between $$\frac{F_{PRF}}{2*E} \text{ and } \frac{F_{PRF}}{2}$$

can be detected theoretically without aliasing for an ensemble size E. Since vibrations can be broadband, a high-frequency vibration interrogated at a low PRF value can be mistaken for noise using this algorithm. Thus, for better sensitivity, it is desirable to select a PRF and an ensemble size so that only a few periods of the vibration are included in the ensemble. Accordingly, the maximum detectable frequency is $$\frac{kF_{PRF}}{E}$$

when k periods of the vibration are included in an ensemble. A simulation and phantom experiments that were carried out indicate that reliable detection may be performed using only one half to six vibration periods during the interrogation period. For example, with a PRF of 1 kHz and an ensemble size of 16 periods/pulses, vibrations with frequency between 31.3 Hz and 375 Hz may be reliably detected.

Quantification of Residual Lumen Diameter

Since the tissue vibrations are produced by the blood flow eddies, the frequency of the tissue vibrations is the same as the frequency of the eddies. The frequency spectrum of the vibrations depends upon the effective diameter of the turbulent jet, thus, the bruit spectrum is related to the severity of the stenosis. The bruit spectrum exhibits a peak frequency beyond which the energy falls off rapidly with increasing frequency. The Strouhal number (S) relates the break frequency of turbulent fluctuations ($f_{vib}$) to the length scale of the turbulence (the residual lumen diameter at the stenosis (D) and the mean downstream blood velocity in the unobstructed vessel (U)) according to:

$$S = \frac{f_{vib} \times D}{U} \qquad (13a)$$

It has been empirically observed in carotid artery stenoses that at the break frequency the product of the carotid artery flow velocity and the Strouhal number remains relatively constant at about 500 mm/s in most individuals. Therefore, a simple relationship exists between the break frequency and the residual lumen diameter:

$$d \sim \frac{500}{f_b} \qquad (13b)$$

In arteries other than the carotid artery, the flow velocity can be estimated using pulsed-wave Doppler. The break frequency can be then used to quantify the residual lumen diameter at the stenosis, assuming the Strouhal number remains constant at a value of 1.

Furthermore, the ability to directly measure the amplitude of the vibrations enables a stenosis to be graded. The energy in the eddies (E) and thus, the amplitude of the tissue vibrations ($\alpha_{vib}$), is directly proportional to the flow rate, as follows:

$$E \propto \alpha_{vib}^2 \propto U^2 \qquad (14)$$

Heretofore, other techniques of analyzing bruits (such as auscultation, phonoangiography and phonocardiography) have not been able to directly measure the amplitude of wall vibrations associated with stenoses. The ability to directly measure the amplitude of the vibrations enables the quantification of other parameters associated with stenosis and corresponding vibrations, such as acoustic power, pressure drop across the stenosis (e.g., in the coronary arteries), and flow power dissipation. Empirical data collected from stenosed blood vessels using such techniques can be analyzed to identify stenosis profiles indicative of hemodynamically significant stenoses. It should also be recognized that 3-D ultrasound imaging would facilitate providing an accurate localization of a stenosis. For example, such imaging will facilitate determining with which of the three major coronary arteries a stenosis is associated.

Sources of Artifacts

In color-flow data acquisition, interrogation along each scan line is performed for only a brief period of time. Vibrations are transient, with typical durations of 10 ms-100 ms. Thus, there is a possibility that some vibrations may not be interrogated. Since the vibrations typically have a relatively large spatial extent and repeat every cardiac cycle, it is unlikely that the vibrations will be missed entirely; however, the spatial extent of the vibrations visible in the image may be only a part of the true spatial extent. By appropriately choosing the PRF and the region of interest, such discrepancies may be minimized.

Other artifacts may be falsely detected as vibrations. Transducer motion may introduce additional frequency peaks in the clutter spectrum and may cause false detections; however, using a trained sonographer to perform the scanning may minimize these false detections. Vibrations in the tensed skeletal muscle of the sonographer, and any ambient vibrations may be detected in the vibration image. In addition, the high-resolution spectral estimation methods may produce spurious peaks that can be falsely detected as vibrations. Such artifacts can be easily distinguished from pathological vibrations, which are expected to be correlated with the anatomy and periodic with every cardiac cycle. These artifacts can be also avoided if additional temporal samples are available. Any vibrations displayed in the vibration image should therefore be confirmed with the vibration spectrum by placing a Doppler sample volume at the location of the peak intensity.

Comparison of the Algorithms Derived from Modeling

The ability of the proposed algorithms to detect vibrations was evaluated using a simulation model. Simulations show that subspace-based algorithms such as MUSIC and ESPRIT have high sensitivity (96%) and specificity (98%) for detecting narrowband vibrations in the presence of clutter as well as blood flow and are robust even when broadband vibrations are present. For narrowband vibrations, an algorithm based on an autoregressive model has a slightly improved specificity (99%), a comparable sensitivity, and is robust to broadband vibrations. The phase decomposition-based algorithm has a slightly lower sensitivity (93%) and specificity (98%), but is more robust to broadband vibrations.

The computational requirements of the proposed algorithms are shown below in Table 2. The subspace-based algorithms (MUSIC/ESPRIT) have a computational requirement that is highly dependent on the choice of model order. In these algorithms, eigen decomposition is the most computationally-intensive task. The autoregression-based algorithm is less computationally intensive, and the computational requirement is less dependent on the model order. In this case, the computation of the FFT for spectral estimation is the most computationally-intensive task. The phase decomposition method is the least computationally intensive, since it involves operations on real signals only. Thus, the phase-decomposition algorithm is most suitable for real-time implementation.

TABLE 1

| Field II Simulation Parameters | |
| --- | --- |
| Center frequency | 5 MHz |
| PRF | 500 Horizontal |
| Transducer excitation | 5-period sinusoid |
| Transducer impulse response | Hanning-weighted 2-period sinusoid |
| f number | 2 |
| Number of elements | 192 |
| Transducer height | 15 mm |
| Element pitch | 0.4 mm |
| Element kerf | 0.03 mm |
| Transmit aperture | 25.6 mm |
| Receive aperture | 25.6 mm |
| Transmit focus | 40 mm |
| Receive focus | 30 mm to 100 mm in steps of 10 mm |
| Elevation focus | 20 mm |
| Mathematical element size | 0.37 mm × 1.5 mm |
| Sampling frequency | 105 MHz |
| Sound velocity | 1540 m/s |
| Number of scan lines | 32 |
| Number of ensembles | 10 |

TABLE 2

Computational requirement (million operations/sec) for real-time imaging at 10 frames/s with 32 scan lines, 256 samples/scan line, and ensemble 10

| | Model Order | | |
| --- | --- | --- | --- |
| Algorithm | p = 2 | p = 3 | p = 4 |
| MUSIC | — | 3631 | 7653 |
| ESPRIT | — | 2218 | 6455 |
| AR | — | 1606 | 1630 |
| Phase-decomposition | 181 | 489 | 1107 |
| Color flow | | 89 | |

2D Fourier Transform Processing for Improved Tissue Motion Spectrum

FIG. 5A graphically illustrates both a 2D Fourier (2D FFT) spectrum and a conventional Doppler spectrum of simulated received ultrasound echoes when scatterers responsible for the echoes are moving with constant velocity of 20 mm/s, with the Doppler spectrum being disposed to the left of the vertical axis, and the 2D FFT spectrum being disposed on the right of the vertical axis. The motion of the scatterers represented here is axially along a direction of an ultrasound beam. Note the spectrum of the received pulse lies on a line that passes through the origin with slope:

$$\frac{f_{tiss}}{f_{RF}} = \frac{2v_{tiss}}{c} = 2.59 \times 10^{-5} \quad (15)$$

The peak in the Doppler spectrum (on the left of the vertical axis) corresponds to the Doppler shift of $$\frac{2f_0 v_{tiss}}{c} = 129 \text{ Hz},$$

as indicated by a line 21.

FIG. 5B graphically illustrates both a 2D Fourier (2D FFT) spectrum and a conventional Doppler spectrum of simulated received ultrasound echoes when scatterers responsible for the echoes are moving with constant velocity of 20 mm/s and also vibrating with a frequency 300 Hz and an amplitude of 5 µm, with the Doppler spectrum being disposed to the left of the vertical axis, and the 2D FFT spectrum being disposed on the right of the vertical axis. From Eq. (8), the presence of a vibration causes a Bessel modulation of the received signal, which generates multiple copies of the spectrum illustrated in FIG. 5A, on lines parallel to a line through the origin, and offset with respect to each other by $f_{vib}$. The conventional Doppler spectrum (i.e., on the left of the vertical axis in FIG. 5B) shows the corresponding peaks that are respectively at frequency of 129+300=429 Hz (as indicated by line 23) and 129−300=−171 Hz (as indicated by arrow 25).

Several insights can be obtained from this 2D spectral formulation of the simulated received echoes. A first observation is that the spectral spread of the Doppler spectrum depends upon the Doppler shift. This point can be further appreciated from the 2D FFT in the case of a high scatterer velocity of 200 mm/s, as graphically illustrated in FIG. 6A, which includes both a 2D FFT spectrum and a conventional Doppler spectrum of received ultrasound echoes (where the center frequency of the transmitted ultrasound signal is 5 MHz) when scatterers responsible for the echoes are moving with constant velocity of 200 mm/s and also vibrating with a frequency 300 Hz, at an amplitude of 5 µm. In this case, the Doppler spectrum is disposed to the left of the vertical axis, and the 2D FFT spectrum is disposed on the right of the vertical axis. For this example, although the parallel harmonic bands are visible in the 2D FFT spectrum, the large spread in the Doppler spectrum almost completely obscures the vibration pattern. FIG. 6B depicts the same situation when a lower ultrasound center frequency of 2 MHz is used for interrogation (i.e., for both a 2D FFT spectrum and a conventional Doppler spectrum of received ultrasound echoes) and when scatterers responsible for the echoes are moving with constant velocity of 200 mm/s, and also vibrating with a frequency 300 Hz, at an amplitude of 5 µm. The Doppler spectrum is disposed to the left of the vertical axis, and the 2D FFT spectrum is disposed on the right of the vertical axis. Note that since the Doppler shift of the 2 MHz ultrasound frequency of FIG. 6B is lower, the spread in the Doppler spectrum in FIG. 6B is reduced as compared to the spread in the Doppler spectrum of FIG. 6A, and the symmetric vibration signature is partially visible. Therefore, for analyzing vibrations in rapidly moving tissue, such as the cardiac wall, a lower frequency should be chosen for the transmit pulse of the interrogating ultrasound wave.

Another insight relates to recognizing that tissue acceleration causes a broadening of the 2D FFT spectrum. In cardiac tissue, acceleration can range from 0-10 $M/s^2$. FIG. 7A graphically illustrates both a 2D Fourier (2D FFT) spectrum and a conventional Doppler spectrum of simulated received ultrasound echoes from a group of scatterers accelerating from 10 mm/s to 30 mm/s within the interrogation window (i.e., with an acceleration of 5 $M/s^2$), with the Doppler spectrum being disposed to the left of the vertical axis, and the 2D FFT spectrum being disposed on the right of the vertical axis. The conventional Doppler spectrum (i.e., the spectrum to the left of the vertical axis), shows a significant spectral broadening, even with a 2-MHz transmit pulse. Further, FIG. 7B graphically illustrates both a 2D FFT spectrum and a conventional Doppler spectrum of simulated received ultrasound echoes from a group of scatterers accelerating from 10 mm/s to 30 mm/s within the interrogation window (i.e., with an acceleration of 5 $m/s^2$), when the scatterers are also vibrating with a frequency 300 Hz and an amplitude of 5 µm, with the Doppler spectrum being disposed to the left of the vertical axis, and the 2D FFT spectrum being disposed on the right of the vertical axis. FIG. 7B indicates that when a vibration is present in accelerating tissue, the high acceleration can significantly obscure the vibration spectrum. Thus, it is important to preprocess the received ultrasound data to suppress the effect of tissue acceleration.

The phase of the received ultrasound signal as described in Eq. (5) is influenced primarily by the axial component of the displacement. If the tissue were perfectly homogeneous, the phase would remain unchanged for any motion orthogonal to the axial direction. However, due to the non homogeneous nature of many tissues, there is a change in the phase as well as the amplitude of the received signal, even for the lateral and elevation components of motion. Thus, off-axis motion components do affect the received signal. The presence of transverse velocity components will result in a broadening of the spectrum, which is proportional to the magnitude of the transverse velocity component. Transverse vibration components will cause a similar broadening of the spectrum. In particular, this broadening implies that even if the vibration occurs in a direction perpendicular to the beam axis, the harmonic Bessel bands indicative of vibrations will still be present in the Doppler spectrum. FIG. 8A graphically illustrates both a 2D FFT spectrum and a conventional Doppler spectrum of simulated received ultrasound echoes when scatterers responsible for the echoes are moving with a constant velocity of 20 mm/s, the scatterer motion being perpendicular to the axis of the ultrasound beam, with the Doppler spectrum being disposed to the left of the vertical axis, and the 2D FFT spectrum being disposed on the right of the vertical axis. Note that the Doppler spectrum shows no Doppler shift, but exhibits a broadening that is proportional to the scatterer velocity. FIG. 8B graphically illustrates both a 2D FFT spectrum and a conventional Doppler spectrum of simulated received ultrasound echoes when scatterers responsible for the echoes are moving with a constant velocity of 20 mm/s, the scatterer motion being perpendicular to the axis of the ultrasound beam, where the scatterers are also vibrating with a frequency of 300 Hz, at an amplitude of 5 µm. In this Figure, the Doppler spectrum is disposed to the left of the vertical axis, and the 2D FFT spectrum is disposed on the right of the vertical axis. Note that the harmonic bands characteristic of vibrations can clearly be seen at a frequency of 297 Hz, as indicated by an arrow 27. Therefore, not only is it possible to detect vibrations perpendicular to the beam axis, it is also possible to accurately estimate the vibration frequency. This important characteristic of vibrations offers a significant advantage over conventional duplex ultrasound, where an accurate velocity estimate is highly dependent upon the orientation of the ultrasound beam with respect to the velocity of the moving blood.

As shown in FIGS. 5A-7B, the conventional Doppler spectrum can have a large spectral variance depending upon the Doppler shift and tissue acceleration. Another artifact in conventional Doppler processing is a granular speckle pattern that is produced due to random phase shifts produced by constructive and destructive interference of scattering from multiple scatterers in the sample volume. Speckle artifacts and large variance can mask the underlying harmonic spectral signatures that are associated with vibrations. Such effects are more pronounced when the tissue motion and acceleration are large, such as in the case of cardiac wall motion, which is an important limitation of conventional Doppler processing with respect to analyzing vibrations in the cardiac wall.

Wideband Doppler estimation techniques can reduce the inherent spectral broadening introduced by conventional Doppler spectral processing. As indicated in FIGS. 7A and 7B, the spectral variance is primarily due to the bandwidth of the transmitted signal. Wideband estimation techniques utilize the bandwidth of the transmitted signal to estimate the Doppler shift and thus can reduce the spectral broadening. Such wideband estimates can also reduce the speckle noise, since the contributions from the sample volume are analyzed separately. Several wideband estimation techniques have been proposed, such as Wideband Maximum Likelihood Estimator (WMLE) (Ferrara and Algazi, "*A new wideband spread target maximum likelihood estimator for blood velocity estimation*," IEEE Trans Ultrason Ferroelect Freq Contr. 1991; 38:1-16), the Wideband Cross-correlation Estimator (WCCE) (Bonnefous and Pesque, "*Time domain formulation of pulse-Doppler ultrasound and blood velocity estimation by* cross correlation," Ultrason Imaging, 1986; 8:73-85) and the 2D FFT estimator (Wilson, "Description of broad-band pulsed Doppler ultrasound processing using the two-dimensional Fourier transform," Ultrason Imaging, 1991; 13:301-15). The 2D Fourier transform is of particular interest, since vibrations have a unique signature in the 2D spectrum.

For estimating blood velocity, the Radon transform has been proposed to estimate the slope of the line in the 2D Fourier transform domain (Munik and Jensen. "A new approach for the estimation of axial velocity using ultrasound," Ultrasonics, 2000; 37:661-5). The velocity spread can be obtained by looking at the ρ=0 axis in the Radon transform (ρ-θ domain). In the current approach, this method is adapted for identifying vibrations in the tissue surrounding stenosed blood vessels. Based on FIGS. 5A-5B, the Radon transform domain can be interpreted as a mapping between the normalized Doppler shift $$\frac{f_{tiss}}{f_{RF}},$$

and the frequency shift $f_{vib}$.

FIG. 9A graphically illustrates a Radon transform of the 2D FFT spectrum of FIG. 5A. A peak is seen at the normalized Doppler shift of $2.59 \times 10^{-5}$, at a zero frequency shift. FIG. 9B graphically illustrates a Radon transform of the 2D FFT spectrum of FIG. 5B. Multiple copies of the peak at $2.59 \times 10^{-5}$ can now be seen at different frequency shifts. The corresponding Doppler spectra can be extracted from the Radon transform by plotting the intensities corresponding to all the frequency shifts at the peak Doppler shift. FIGS. 9C and 9D graphically illustrate the corresponding Doppler spectra computed from the Radon transforms of FIGS. 9A and 9B. Compared to the Doppler spectra in FIGS. 5A and 5B, the spectral spread is significantly reduced. The vibration peaks occur at the frequency of ±278 Hz (a 7.3% error compared to the actual value of 300 Hz), as indicated by arrows 29 in FIG. 9D. The difference between the tissue motion peak (indicated by an arrow 31) and the first vibration peak (arrows 29) is 4.9 dB, which corresponds to an estimated vibration amplitude of 7.9 μm (a 58% error compared to the actual value of 5 μm).

An alternative blood velocity estimator can be derived from the 2D FFT spectrum by combining appropriately scaled Doppler spectra corresponding to the whole range of frequencies in the transmitted bandwidth (Loupas and Gill, "Multifrequency Doppler: Improving the quality of spectral estimation by making full use of the information present in the backscattered RF echoes," IEEE Trans Ultrason Ferroelect Freq Contr., 1994; 42:672-88). The estimated velocity spectra from this method is given by $$P_{MF}(f_{DOP}) = \frac{\int_{f_0-BW/2}^{f_0+BW/2} |Y(f_{RF}, f_{DOP})|^2 df_{RF}}{\int_{f_0-BW/2}^{f_0+BW/2} |Y_0(f_{RF} - f_0)|^2 df_{RF}} \quad (16)$$

where $f_0$ is the center frequency, BW is the bandwidth of the transmitted pulse, $f_{RF}$ and $f_{DOP}$ are the spatial and temporal frequency in the 2D FFT domain, respectively, and $Y(f_{RF}, f_{DOP})$ and $Y_0(f_{RF})$ are the Fourier transforms defined in Eq. (7). This estimate is referred to as the "multifrequency estimate." The multifrequency estimate improves the velocity resolution, since the large statistical fluctuations introduced by the integration over a sample volume are avoided. In the present disclosure, these techniques have been adapted for identifying vibrations in the tissue surrounding a stenosed blood vessel. The multifrequency estimates computed from FIGS. 5A and 5B using 1-MHz bandwidths are respectively illustrated in FIGS. 10A and 10B. The tissue motion peak is at 125 Hz, as indicated by an arrow 33 (in FIGS. 10A and 10B), which corresponds well with the expected Doppler shift of 129 Hz. The first vibration peaks are at −172 Hz and 422 Hz, respectively (as indicated by arrows 35 in FIG. 10B), resulting in an estimated vibration frequency of 297 Hz, according to Eq. (13) (a 1% error compared to the actual value of 300 Hz). The difference between the low-frequency peak and the first vibration peak is 6.5 dB, which corresponds to an estimated vibration amplitude of 5.48 μm (a 9.6% error compared to the actual value of 5 μm).

As shown above, the multifrequency estimate provides a more accurate estimate of the vibration amplitude and frequency as compared to the Radon transform. The Radon transform estimate automatically corrects for the Doppler shift due to mean tissue motion, whereas this Doppler shift is preserved in the multifrequency estimate. The spectral spread of the multifrequency estimate is similar to that of the Radon transform estimate. However, the additional computational burden of computing the Radon transform makes the estimate based on the Radon transform less desirable than the multifrequency estimate.

Validation of Ultrasound Vibration Imaging of Stenoses Using a Simulation Model

To evaluate the proposed stenosis vibration detection algorithms, a simulation model of vibrations in a blood vessel wall was developed. FIG. 11A schematically illustrates the simulation model (i.e., a 3D model of scatterer distributions) used in the validation. The ultrasound simulator Field II (Jensen 1996) was used to compute the pulse echo spatial impulse response, $h_{pe}(\cdot)$, and the transducer temporal response, $x_0(\cdot)$. The scattering amplitudes, %, and mean positions, $r \rightarrow_s$, were randomly assigned from a Gaussian distribution with the scattering strength from the vessel wall 40 dB higher than that from blood. The instantaneous scatterer positions, $v(r \rightarrow, t)$, were estimated using the phase of the Doppler ultrasound signal from the vessel wall of a normal human femoral artery, as is graphically illustrated in FIG. 11B. The motion was defined as being in a direction perpendicular to the vessel wall with a peak displacement of 0.08 mm. Vibrations were generated in one region of the vessel wall, with motion in a direction perpendicular to the vessel wall, with the peak amplitude of 5 μm and a frequency of 100 Hz. The clutter motion with vibrations is graphically illustrated in a box 180 of FIG. 11B. The vibration, $d_r^{vib}(t)$ was modeled as a Gaussian-weighted sinusoid with additive white Gaussian noise at different signal-to-noise ratios (SNR), as follows:

$$d_r^{vib}(t) = a_0 \sin(2\pi f_{vib} t) e^{A_5} \left( \frac{1 + \beta_{SNR} n(t)}{1 + \beta_{SNR}} \right), \quad (17a)$$

$$A_5 = \frac{(t - t_{position})^2}{2 t_{duration}^2} \quad (17b)$$

where $t_{position}$ and $t_{duration}$ are the position and duration of the vibration in the cardiac cycle, $\beta_{SNR}$ is the SNR of the white Gaussian noise $n(t)$. The addition of Gaussian noise simulates broadband vibrations expected to be produced by blood flow eddies and turbulent flow. The vibration frequency was 100 Hz and $\beta_{SNR}$ was varied from 0 to 2.

Signals from blood were considered to be part of the noise spectrum in both the primary algorithms. To further validate that signals from flow would not be falsely detected as vibrations, blood flow was also simulated in the validation model of FIG. 11A. The motion of scatterers corresponding to blood was generated using the model of flow in a human femoral artery proposed by Jensen (1996). The blood flow introduced into the model is parabolic with a peak velocity of 50 cm/s. The time-varying velocity profile of the simulated blood flow is graphically illustrated in FIG. 11C.

The Field II simulation parameters have been noted above in Table 1. The simulated radiofrequency (RF) lines obtained were demodulated to obtain the in-phase (I) and quadrature (Q) data, and these were decimated to obtain the raw color-flow data. The vibration detection performance was evaluated with different threshold values to measure the sensitivity and specificity. For the phase-decomposition algorithm, the threshold value, $E_{thresh}$, indicates the % of energy in the dominant components for a signal to be considered as vibrations. For the root-MUSIC-based algorithm (i.e., the algorithm based on estimating complex exponentials in noise), the threshold value, $F_{thresh}$, indicates the maximum difference in frequency of a matching pair of complex exponentials. Simulations were performed with different threshold values and different model orders, and receiver-operating characteristic (ROC) curves were generated to evaluate the detector performance. The ROC curves can then be used as a guideline for choosing the appropriate threshold setting and model orders. For the phase-decomposition algorithm, the pth order model had a 2(p+1)×2(p+1) correlation matrix, with 2≦p<E/2 for an ensemble size of E. Two dominant components were considered for vibration detection. For the root-MUSIC algorithm, the model order p was chosen so that 3≦p<E/2 to enable detection of a matching pair of exponentials, and the estimated correlation matrix size was 2p×2p (Stoica and Moses 1997).

FIG. 12A is a vibration amplitude image overlaid on a B-mode image using a black-green colormap. The colormap is calibrated according to the values of the estimated amplitude. To quantitatively evaluate the proposed algorithms, two masks (graphically illustrated in FIG. 12B) were generated, V corresponding to regions where vibrations were simulated, and NV corresponding to regions where no vibration is present. Because the scatterers have a time-varying motion, the masks are appropriately generated spatially to ensure that no vibrating scatterers are present in region NV. The percentage of pixels correctly detected as vibrations in region V are counted as true-positives, and the percentage of pixels detected as vibrations in region NV are counted as false-positives.

The sensitivity, specificity and ROC curves for the two primary algorithms discussed above (the phase decomposition algorithm and the algorithm based on estimating complex exponentials in noise) using different model orders are graphically illustrated in FIGS. 13A-13F. FIG. 13A indicates that, for the phase-decomposition algorithm shown in FIG. 3A, the sensitivity decreases with the increasing threshold value for all model orders, because more true vibrations are rejected with larger threshold values. Lower model orders have higher sensitivity, because the correlation matrix is smaller; thus, a better estimate can be obtained using the limited number of temporal samples.

FIG. 13B shows that the specificity is quite similar for all the model orders and increases with increasing threshold value, because a larger threshold leads to better noise rejection. Upon closer investigation, it was determined that the majority of false detections occur when the blood flow velocity is low and the clutter-to-blood signal ratio is high. In such cases, the I-Q Doppler signals from blood can be almost indistinguishable from those of a small-amplitude tissue vibration. The ROC curves for different model orders are graphically illustrated in FIG. 13C, which indicates that a sensitivity of 96% and a specificity of 98% can be achieved with a second-order model. To choose an appropriate threshold value, an operating point is selected in the ROC curve. The corresponding threshold value can then be found from FIG. 13A or 13B.

FIG. 13D shows that, for the root-MUSIC-based algorithm shown in FIG. 3A, the sensitivity increases with the increasing frequency threshold value for all model orders, as more true vibrations can be detected if the frequency threshold is increased.

FIG. 13E shows that the specificity decreases with increasing threshold values, because more false detections occur with increased frequency threshold. The fourth-order model has slightly better sensitivity and specificity due to better modeling of the clutter space.

The ROC curves for the root-MUSIC-based algorithm are graphically illustrated in FIG. 13F. For the third-order algorithm, a sensitivity of 97% and a specificity of 98% are achievable, whereas, for the fourth-order algorithm, the sensitivity can be increased to 98%, with a specificity of 99%.

Figure 3C:
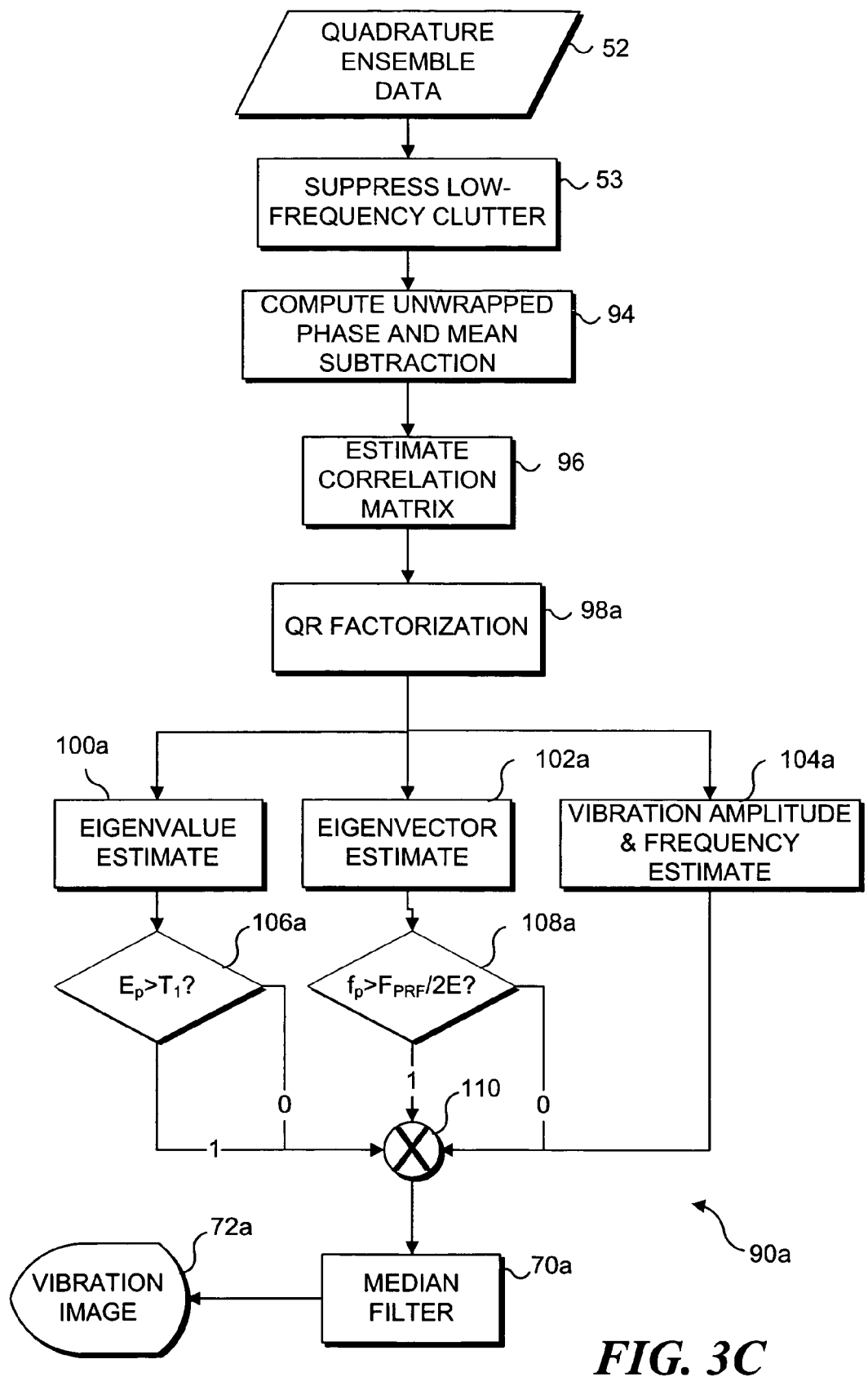
FIG. 3C is a flow chart showing the logical steps of yet another exemplary alternative algorithm that uses phase decomposition for creating a vibrating tissue image in which a stenosis is evident.

The variation in the sensitivity with increasing vibration band width is graphically illustrated in FIG. 14, which indicates that both the phase-decomposition algorithm of FIG. 3C (indicated by a line 200) and the root-MUSIC algorithm of FIG. 3A (indicated by a line 202) can achieve similar sensitivity when the vibration is narrowband ($\beta_{SNR}$=0). As the vibration bandwidth is increased, the sensitivity decreases for the root-MUSIC algorithm (line 202) because it is based on modeling the vibrations as complex exponentials with narrow bandwidth. On the other hand, the phase-decomposition algorithm (line 200) is more robust to the vibration bandwidth because it makes no a priori assumptions about the vibration bandwidth characteristics.

Tissue Vibration Imaging System

For tissue vibration imaging to be clinically useful, real-time visualization of vibrations is quite desirable. Programmable ultrasound signal and image-processing systems using high-performance multimedia processors to support all the conventional processing modes, such as B, M, color flow, and Doppler are available in software. The main strength of a programmable system is the ease of development of new modes and applications without the need for new hardware or making hardware modifications to conventional ultrasound machines. Such programmable ultrasound machines allow access to and processing of internal raw color-flow and pulsed-wave (PW) Doppler quadrature data, and facilitate implementing the phase-decomposition algorithm discussed above for tissue vibration imaging in real time.

The phase-decomposition algorithm has already been empirically tested in a software-programmable ultrasound system for online visualization of vibrations during 2D ultrasound scans. Currently, tissue vibration imaging can be achieved at 9.1 frames/s for 32 scan lines with an ensemble size of 10 and 256 samples per scan line. The computational power of ultrasound machines has increased significantly in recent years, benefiting from advances in processor technology, and this trend is expected to continue in the future. Many modern processors targeted for multimedia applications have specialized instructions that can perform complex multiplications and additions with the same computational overhead as real multiplications and additions. Using such processors, the computational burden to support the algorithms disclosed herein can be reduced by a factor of three or four. Thus, the additional computational burden of the tissue-vibration imaging algorithms disclosed herein can be reasonably supported in modern ultrasound machines.

Experimental Validation

FIG. 15 schematically illustrates a test system including a physical phantom (i.e., a vibrating plate) used for validating the vibration-imaging algorithms discussed above. A piezoelectric plate 182 is incorporated into a test vessel including walls 183 and a plastic base 181. The piezoelectric plate is logically coupled with a function generator 194. The test vessel is filled with water 184. An ultrasound probe 186 (logically coupled to an ultrasound scanner 192), and a fiber optic micrometer 188 (logically coupled to an oscilloscope 190) are disposed in the water bath (i.e., in the test vessel filled with water) proximate the piezoelectric plate, which was vibrated at frequencies between 100 Hz and 800 Hz using a sinusoidal signal from a function generator 194. The amplitude of the vibrating plate was calibrated using fiber optic micrometer 188 for different drive voltages corresponding to peak plate displacements of 1 to 7 μm. Piezoelectric plate 182 was then imaged using a programmable ultrasound system with a 5-MHz linear transducer and an ensemble size of 10 at different PRFs. The position of the plate was also measured using the fiber optic micrometer, enabling a comparison to be made with the data obtained using ultrasound.

FIG. 16A is a vibration amplitude image of the plate phantom (i.e., FIG. 18), while FIG. 16B is a vibration frequency image of the plate phantom, indicating that vibrations have been correctly detected at the location of the piezoelectric plate. Because the edges of the plate are attached to the base, the maximum vibration amplitude is expected at the center of the plate, with zero displacement at the edges, which indeed corresponds to what is shown in FIG. 16A. The estimated vibration frequency at the center of the plate is between 450 and 500 Hz. The MUSIC pseudo-spectrum is shown in FIG. 16C, which indicates that the zero-frequency peak corresponds to stationary echo. A prominent double-sided peak is observed at ±500 Hz, corresponding to the vibration frequency of the plate.

FIG. 17A graphically illustrates the ultrasonically estimated vibration amplitude (y-axis) versus the independently measured values using the fiber optic micrometer of FIG. 15 (x-axis) for different drive voltages used to displace the piezoelectric plate. The amplitude and frequency were estimated using the estimators defined in Eqs. (8) and (9). The fiber optic amplitude measurements were made at the center of the plate. FIG. 17B graphically illustrates the ultrasonically estimated frequency (y-axis) versus the function generator frequency (x-axis). A solid line 204 with a slope of unity is shown in both plots. The difference between the estimated and measured values is plotted against the corresponding measured value in FIG. 17C for amplitude and in FIG. 17D for frequency. As can be seen from the Figures, the maximum difference between the detected and measured values is less than 1 μm for amplitude and less than 50 Hz for frequency for both estimators. Some of the differences in amplitude can be attributed to variability in the location on the plate at which the fiber optic measurements were made.

To validate the ability to visualize wall vibrations caused by stenoses and to estimate the vibration spectrum, studies were performed using a pulsatile flow phantom. Experiments were performed on we vivo lamb arteries. FIG. 18 schematically illustrates the experimental setup, which includes a computer-based controller 140 logically coupled with an oscilloscope 142 and a fiber optic micrometer 148, a Doppler capable ultrasound-imaging machine 144 and an imaging probe 146. Fiber optic micrometer 148 and imaging probe 146 are positioned proximate to an in vivo artery sample 150 disposed in a water bath 152. Pulsatile flow mimicking human arterial flow is created through the artery sample using a pulsatile pump 154. The output of pulsatile pump 154 (a Pulsatron™ pump, available from Pulsafeeder Inc, Punta Gorda, Fla.) is connected to the in vivo artery sample through a damping column 156. Adjusting the height of fluid in the damping column controls the overall flow impedance, such that the Doppler flow profile in the artery can be made to appear visually similar to that of human arterial flow, as shown in FIG. 19. Data were collected from patients with stenosed bypass vein grafts, who had audible bruits.

The time-varying wall displacement is measured using ultrasound as well as the fiber-optic micrometer. The output of the micrometer is digitized using the oscilloscope, and the data are acquired using the computer-based controller. The raw ultrasound data are acquired digitally from inside the ultrasound machine. The power spectra of the wall displacement determined using both methods can then be compared. Stenoses are simulated by partially ligating one part of the artery to reduce the effective lumen diameter. Power spectra measurements are then repeated using both ultrasound and fiber-optic methods.

FIGS. 20A and 20B are vibration amplitude images from two different ex vivo arteries with simulated stenoses. In FIG. 20A, a 30% stenosis is simulated in a 3.4 mm diameter artery. The wall vibrations occur downstream, at a distance of approximately four artery diameters. In FIG. 20B, a 42% stenosis is simulated in a 3.1 mm diameter artery, and the wall vibrations occur closer, approximately three diameters downstream. FIGS. 20A and 20B indicate that using the technique described above, it is possible to distinctly image the location of the artery wall vibrations (and hence, the location of the stenosis). In each image, the stenosis sites are indicated by solid arrows 141, while dash arrows 143 indicate the direction of flow. The region of interest in each image is indicated by a box 145.

FIG. 21 graphically illustrates the mean vibration spectra determined using ultrasound, indicated by an arrow 147, and the fiber-optic micrometer (see FIG. 18, discussed above), indicated by an arrow 149, during peak flow acceleration. The vertical bars indicate the standard deviations. Both spectra have a similar shape, and a break frequency can be observed beyond which the energy drops off rapidly. This result indicates that it is possible to assess the wall vibration spectrum using ultrasound.

In Vivo Vibrations in Human Bypass Vein Grafts

To study the characteristics of pathologic tissue vibrations in vivo, data were collected from a patient with a stenosed bypass vein graft in the femoral artery. A programmable ultrasound machine was used for real-time imaging and data collection, a 5-MHz linear probe was used for imaging and data collection with a PRF of 500 Hz and an ensemble size of 10 pulses in color-flow mode and a PRF of 4-8 kHz in PW Doppler mode.

The vibration-imaging algorithm discussed above in connection with FIG. 3A (preferably employing the ESPRIT method) was implemented on a programmable ultrasound machine, the Hitachi HiVision 5500™, which is manufactured by Hitachi Medical Systems America, Twinsburg, Ohio.

All of the signal and image processing on this machine is performed by software, thus providing the flexibility to easily incorporate new algorithms. This system, programmed to use the algorithms disclosed above, enables vibrations to be visualized in real time, facilitating the evaluation of the technique described above during an in vivo procedure.

The vein grafts were first visualized using color-Doppler ultrasound. FIG. 22A is a Color-Doppler image from a stenosed vein graft in a human subject. The PRF was adjusted until the perivascular artifact of the bruit was visible. A vibration amplitude image was then created in real time. FIG. 22B is a vibration amplitude image of the stenosed vein graft of FIG. 9A. Once the bruit was visible in the 2D vibration image, a Doppler sample volume was placed at the location with the maximum vibration amplitude. The vibration spectrum was then generated from the pulsed-wave Doppler data using the technique described above (see FIG. 3A). The "break" frequency in the vibration spectrum was noted.

FIG. 23A is a color power image of a stenosed vein graft, FIG. 23B is a vibration amplitude image of the same stenosed vein graft and FIG. 23C is a vibration frequency image of the same stenosed vein graft. An arrow 206 indicates the location of the stenosis. A perivascular artifact is visible in the color power image, as indicated by an arrow 208, while the vibration amplitude image clearly shows the origin of the bruit downstream of the stenosis, as indicated by arrows 210. The vibration amplitude is highest close to the vessel wall and decreases farther away from the vessel wall.

To evaluate the vessel wall displacement in more detail, a range gate was placed at the location of the peak vibration amplitude and the displacement was estimated from the phase of the Doppler signal (generally as described above in connection with FIG. 5). The instantaneous position of the vessel wall and the corresponding spectrum are shown as a function of time in FIGS. 24A and 24B. FIG. 24A graphically illustrates instantaneous vessel wall position estimated using the phase of pulsed-wave Doppler data from a stenosed femoral vein graft, with vibrations being indicated in boxes 212. FIG. 24B is a motion periodogram of the signal from FIG. 24A. The displacement spectrum in FIG. 24B shows significant energy up to 200 Hz, and repeats with each cardiac cycle.

A cross section of the spectrum in FIG. 24B at a time of 1.25 seconds is graphically illustrated in FIG. 24C. A peak is observed at the break frequency of about 90 Hz, as indicated by an arrow 214), beyond which the energy decays with increasing frequency. FIG. 24D graphically illustrates the pseudo-spectrum estimated from only 10 ensembles of color-flow data at the same location using the MUSIC algorithm, generally as described in connection with FIG. 3A. A prominent spectral peak is observed at the break frequency, as indicated by an arrow 216. It should be noted that the MUSIC pseudo-spectrum does not reflect the full spectral characteristics, but may be used to estimate the spectral peaks. This case study shows that in vivo tissue vibrations caused by blood flow eddies can be detected using only a short temporal record, demonstrating the feasibility of real-time vibration imaging.

FIG. 25A graphically illustrates the wall displacement spectrum from a normal femoral artery computed using the estimated displacement from pulsed-wave Doppler data. The spectral energy rapidly decays within a few tens of Hz, and the spectral energy beyond 100 Hz is comparable to the noise level. FIG. 25B graphically illustrates the spectrum from a stenosed bypass vein graft. The spectral energy decays more gradually, and a significant energy is present, even at several hundred Hz. An arrow 160 indicates the break frequency, beyond which the energy decays with increasing frequency.

FIG. 25C graphically illustrates the spectrum from a second stenosis in the same patient. A peak in the spectrum can be observed at the break frequency, as indicated by an arrow 162. The overall shape of the spectrum is similar to that in FIG. 25B.

FIG. 25D graphically illustrates the spectrum from a vein-graft stenosis in a different patient. Again, a prominent spectral peak can be observed at the break frequency, as indicated by an arrow 164.

For a real-time quantitative assessment of vibration spectra, a scrolling display technique can be implemented, where the horizontal axis represents time, the vertical axis represents frequency on a logarithmic scale, and the pixel intensity represents the vibration intensity. FIGS. 26A-26D graphically illustrate such a time-varying wall vibration spectrum. In a normal femoral artery, represented by FIG. 26A, the spectral energy beyond 45 Hz is comparable to the noise level. In case of stenoses, significant spectral energy is present in the higher frequencies, as graphically illustrated in FIGS. 26B-26D. In all three stenoses (i.e., as shown in FIGS. 26B-26D), the vibration occurs just after the peak systolic wall motion. The break frequency can be determined visually from this time-varying vibration spectral display, as shown by arrows 166, 168, and 170. Automatic detection of these break frequencies can also be performed in real time.

In Vivo Vibrations in Human Coronary Arteries

FIG. 27A is a Doppler spectrum computed using the 2D FFT method described above from a range placed on the myocardial wall of a patient with angiographically confirmed coronary artery disease in the left anterior descending (LAD) artery and the right coronary artery (RCA). The range gate was placed in the vicinity of the RCA. The four phases of myocardial wall motion corresponding to isovolumetric contraction (IVC), ventricular ejection (VE), isovolumetric relaxation (IVR), and ventricular filling (VF) are indicated. A clear harmonic spectrum indicative of high-frequency narrowband vibrations can be observed during the latter part of the ventricular ejection phase. The vibrations have continuously decreasing frequency and appear as oblique bands, and repeat in two consecutive cardiac cycles. The symmetric double-sided peaks are indicative of vibrations observed in the late ventricular ejection phase.

FIG. 27B graphically illustrates a detailed time course of the wall velocity during ventricular ejection, estimated using the autocorrelation method discussed in detail above. The velocity shows oscillatory components indicative of vibrations, as indicated in a boxed enclosed region. The duration of the oscillation is approximately 85 ms, and the oscillation appears to have harmonic components.

FIG. 28A is an angiographic image of a right coronary artery of the patient imaged in FIGS. 27A and 27B, acquired in the left anterior oblique projection with caudal angulation. A diffuse 20% stenosis in the proximal RCA, a tubular 20% stenosis in the mid RCA, and a 40% stenosis in the distal RCA can be identified.

FIG. 28B is a vibration amplitude image overlaid on an apical two-chamber view in diastole from the patient of FIGS. 27A, 27B and 28A. Vibrations in the posterior left-ventricular wall can be seen near the mid and distal portions of the RCA. The vibrations appear to be localized in two regions, which could correspond to the two different lesions in the distal RCA.

FIG. 29A is an angiographic image of the patient imaged in FIGS. 27A, 27B, 28A and 28B, acquired in the right anterior oblique projection with cranial angulation. The proximal LAD is moderately calcified. There is a 50% tubular lesion in the mid-LAD.

FIG. 29B is a vibration amplitude image overlaid on the apical two-chamber view of the patient of FIG. 29A. Myocardial vibrations can be observed in the mid-LAD section.

Differentiating Tissue Vibrations Arising from a Stenosis from Other Sources

Vibrations are produced due to pressure differences across an orifice. Stenoses represent a relatively common physiological features including orifices where such pressure differences exist. However, other physiological features, such as punctured blood vessels, also include orifices with pressure differences which can generate vibrations. The following provides a description of how the vibration imaging techniques disclosed herein can distinguish stenoses from other sources of tissue vibrations.

In a stenosis, the pressure difference is typically more significant during systole, whereas in a bleeding vessel the pressure difference could be significant in diastole as well. Thus, analyzing the vibrations with respect to the time at which they occur in the cardiac cycle will provide data that can be used to distinguish vibrations associated with a stenosis from vibrations associated with bleeding.

Referring to FIG. 1, tissue vibration processor 28 can be configured to determine the timing of the vibrations in the cardiac cycle using electrocardiograph signals. In another embodiment, the tissue vibration processor can be configured to determine the timing of the vibrations during the cardiac cycle using the periodicity of tissue motion due to cardiac pulsation.

SUMMARY

Empirical evidence demonstrates the feasibility of real-time ultrasound imaging of low-intensity local vibrations in the vessel wall and surrounding tissue associated with stenosed blood vessels. Several algorithms based on parametric signal decomposition and spectral estimation have been developed for imaging small-amplitude tissue vibrations using as few as 10 temporal samples. Simulations show that these algorithms have high sensitivity (96 to 98%) and specificity (98 to 99%) for detecting vibrations in the presence of clutter as well as blood flow, and are robust even when broadband vibrations are present. The vibration amplitude and frequency can be estimated accurately, and real-time tissue vibration imaging has been implemented on an ultrasound machine with a software-programmable subsystem. Vibrations were observed in stenosed bypass vein grafts and from coronary arteries in human subjects.

Tissue vibration imaging can provide additional diagnostic information that is currently not available to the clinician using conventional tools. An ultrasound device with tissue vibration imaging capability can become a useful screening and diagnostic tool for the assessment of stenoses and other vascular abnormalities traditionally associated with bruits that are otherwise hard to diagnose using conventional duplex ultrasound. The ultrasonic vibration imaging techniques disclosed herein are attractive because of their potential to visualize small-amplitude vibrations at their origin. The vibration spectra can be used to compute the break frequency, which is directly related to the residual lumen diameter at the stenosis. An important application of tissue vibration imaging will likely be the noninvasive diagnosis of coronary artery stenoses. Conventional duplex ultrasound is limited by the difficulty in visualizing coronary arteries and the poor scattering strength from coronary blood flow. Patients with coronary artery stenosis have diastolic murmurs with frequencies between 300 Hz and 800 Hz. Thus, clinically significant coronary artery stenoses are expected to create vibrations with amplitude and frequency dependent on coronary flow rate and minimum residual lumen diameter. Transthoracic assessement of the heart wall vibrations produced by coronary artery disease can become an inexpensive and effective method for diagnosing clinically significant coronary artery stenoses.

Although the present invention has been described in connection with the preferred form of practicing it and modifications thereto, those of ordinary skill in the art will understand that many other modifications can be made to the present invention within the scope of the claims that follow. Accordingly, it is not intended that the scope of the invention in any way be limited by the above description, but instead be determined entirely by reference to the claims that follow.

The invention in which an exclusive right is claimed is defined by the following:

1. A method for detecting a stenosis using ultrasound data, comprising the steps of:
    (a) generating ultrasound data reflected from an internal site using an ultrasound machine including an ultrasound transducer;
    (b) processing the ultrasound data using a vibration processor to identify tissue vibrations at the internal site, producing a tissue vibration signal from which any contribution to the tissue vibration from a source other than the stenosis at the internal site has been reduced, said tissue vibration signal providing an indication of the stenosis, wherein the step of producing the tissue vibration signal is implemented using the following steps:
        (i) estimating a mean clutter velocity from an ensemble of the ultrasound data, using autocorrelation;
        (ii) down mixing the ultrasound data with the mean clutter velocity, producing a down mixed signal;
        (iii) computing a phase of the down mixed signal and a mean phase of the down mixed signal;
        (iv) subtracting the mean phase from the phase of the down mixed signal, producing a residual phase;
        (v) decomposing the residual phase into its dominant components; and
        (vi) applying energy and frequency thresholds to the dominant components, to suppress any contribution to the tissue vibration due to noise and blood flow, yielding an estimate of vibration amplitude and vibration frequency of tissue; and
    (c) outputting an indication of the tissue vibration signal to a user in a format perceptible to the user, wherein the indication conveys to the user that a stenosis is present at the internal site.

2. The method of claim 1, wherein the step of outputting an indication of the tissue vibration data to a user comprises the step of displaying an ultrasound image of the internal site, wherein the tissue vibration data is incorporated into the ultrasound image, enabling the user to determine a position of the vibrations caused by the stenosis relative to the internal treatment site.

3. The method of claim 1, wherein the step of outputting an indication of the tissue vibration data to a user comprises the step of providing at least one of a visual indication of the stenosis to the user, an audible indication of the stenosis to the user and a palpable indication of the stenosis to the user.

4. The method of claim 1, wherein the step of generating the ultrasound data is performed at a first location, and the step of outputting an indication of the tissue vibration data to the user is performed at a second location, the second location being remote from the first location.

5. The method of claim 1, wherein the step of decomposing the residual phase comprises the steps of:
 (a) estimating a correlation matrix from the residual phase; and
 (b) performing an eigen decomposition of the correlation matrix to determine the dominant components.

6. The method of claim 1, wherein the step of decomposing the residual phase comprises the steps of:
 (a) estimating a correlation matrix from the residual phase; and
 (b) performing a partial eigen decomposition of the correlation matrix using iterative QR factorization to determine the dominant components.

* * * * *

UNITED STATES PATENT AND TRADEMARK OFFICE
CERTIFICATE OF CORRECTION

| | | |
|---|---|---|
| PATENT NO. | : 7,736,314 B2 | |
| APPLICATION NO. | : 11/218292 | |
| DATED | : June 15, 2010 | |
| INVENTOR(S) | : Beach et al. | |

It is certified that error appears in the above-identified patent and that said Letters Patent is hereby corrected as shown below:

Column 10, line 55     "modem" should read --modern--

Column 30, line 1     "we" should read --ex--

Column 30, lines 17-18     after "19" delete "Data were collected from patients with stenosed bypass vein grafts, who had audible bruits."

Column 31, line 7     before "The vein" insert --Data were collected from patients with stenosed bypass vein grafts, who had audible bruits.--

Column 16, line 60     "$\|Y(\tau,f)\| = \dfrac{\sigma T^2}{\left|1 + \sum_{j=1}^{P} a_k(\tau)e^{-j2\pi kf}\right|^2}$" should read $$\|Y(\tau,f)\| = \dfrac{\sigma^2}{\left|1 + \sum_{k=1}^{p} a_k(\tau)e^{-j2\pi kf}\right|^2}$$

--

Column 17, line 5     "$A(\tau,f) = \left|1 + \sum_{j=1}^{P} a_k(\tau)e^{-j2\pi kf}\right|$." should read $$A(\tau,f) = \left|1 + \sum_{k=1}^{p} a_k(\tau)e^{-j2\pi kf}\right|$$

--.--

Signed and Sealed this
Fourteenth Day of June, 2011

David J. Kappos
*Director of the United States Patent and Trademark Office*